US006280936B1

(12) United States Patent
Burgin et al.

(10) Patent No.: US 6,280,936 B1
(45) Date of Patent: Aug. 28, 2001

(54) METHOD FOR SCREENING NUCLEIC ACID CATALYSTS

(75) Inventors: Alex Burgin, Chula Vista, CA (US); Leonid Beigelman, Longmont; Laurent Bellon, Boulder, both of CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 09/094,381

(22) Filed: Jun. 9, 1998

Related U.S. Application Data

(60) Provisional application No. 60/049,002, filed on Jun. 9, 1997.

(51) Int. Cl.[7] .............................. C12Q 1/68; C07H 21/02; C07H 21/04
(52) U.S. Cl. ........................ 435/6; 536/24.5; 536/23.1; 536/24.3; 435/6; 435/252.3; 435/320.1
(58) Field of Search .................................. 536/24.5, 24.3, 536/23.1; 435/320.1, 252.3, 6

(56) References Cited

U.S. PATENT DOCUMENTS

| | | | |
|---|---|---|---|
| 5,334,711 | 8/1994 | Sproat et al. | 536/24.5 |
| 5,595,873 | 1/1997 | Joyce | 435/6 |
| 5,610,052 | 3/1997 | Thompson et al. | 435/366 |
| 5,616,459 | 4/1997 | Kramer et al. | 435/5 |
| 5,631,146 | 5/1997 | Szostak et al. | 435/91.1 |
| 5,770,715 | * 6/1998 | Sugiyama et al. | 536/23.1 |

FOREIGN PATENT DOCUMENTS

| | | |
|---|---|---|
| 44 24 762 C1 | 7/1995 | (DE) . |
| 89/02439 | 3/1989 | (WO) . |
| 91/03162 | 3/1991 | (WO) . |
| 92/07065 | 4/1992 | (WO) . |
| 93/15187 | 8/1993 | (WO) . |
| 93/23569 | 11/1993 | (WO) . |
| 94/02595 | 2/1994 | (WO) . |
| 95/06731 | 3/1995 | (WO) . |
| 95/11910 | 5/1995 | (WO) . |
| 95/13380 | 5/1995 | (WO) . |
| 95/23225 | 8/1995 | (WO) . |
| 96/01314 | 1/1996 | (WO) . |
| 96/18736 | 6/1996 | (WO) . |
| 98/32880 | 7/1998 | (WO) . |

OTHER PUBLICATIONS

Cotten, "The in vivo application of ribozymes," *Trends in Biotechnology* 8(7):174–178 (1990).

Jarvis et al., "Inhibition of vascular smooth muscle cell proliferation by hammerhead ribozymes targeting c–myb," *Journal of Cellular Biochemistry* 19A:221 (1995) Abstract Only XP 002024063.

Abramovitz et al., "Catalytic Role of 2'–Hydroxyl Groups Within a Group II Intron Active Site," *Science* 271:1410–1413 (1996).

Banerjee et al., "The Time Dependence of Chemical Modification Reveals Slow Steps in the Folding of a Group I Ribozyme," *Biochemistry* 34:6504–6512 (1995).

Bartel and Szostak, "Isolation of New Ribozymes From a Large Pool of Random Sequences," *Science* 261:1411–1418 (1993).

Beaudry and Joyce, "Directed Evolution of an RNA Enzyme," *Science* 257:635–641 (1992).

Beigelman et al., "Chemical Modification of Hammerhead Ribozynes," *Journal of Biological Chemistry*, 270(43):25702–25708 (1995).

Berzal–Herranz et al., "Essential nucleotide sequences and secondary structure elements of the hairpin ribozyme," *EMBO J.* 12:2567–2574 (1993).

Berzal–Herranz et al., "In vitro selection of active hairpin ribozymes by sequential RNA–catalyzed clevage and ligation reactions," *Genes & Development* 6:129–134 (1992).

Bevilacqua et al., "A Mechanistic Framework for the Second Step of Splicing Catalyzed by the Tetrahymena Ribozyme," *Biochemistry* 35:648–568 (1996).

Breaker and Joyce, "Inventing and improving ribozyme function: rational design versus iterative selection methods," *TIBTECH* 12:268–275 (1994).

Breaker et al., "DNA Enzymes," *Nature Biotechnology* 15:427–431 (1997).

Breaker, "Are engineered proteins getting competition from RNA?" *Current Opinion in Biotechnology* 7:442–448 (1996).

Burgin et al., "Chemically Modified Hammerhead Ribozymes with Improved Catalytic Rates," *Biochemistry* 35:14090–14097 (1996).

Campbell and Cech, "Identification of ribozymes within ribozyme library that efficiently cleaves a long substrate RNA," *RNA* 1:598–608 (1995).

Cech, "Ribozymes and Their Medical Implications," *JAMA* 260(20):3030–3034 (1988).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20(17):4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269(41):25856–25864 (1994).

Chowrira et al., "Novel guanosine requirement for catalysis by the hairpin ribozyme," *Nature* 354:320–322 (1991).

(List continued on next page.)

*Primary Examiner*—Jeffrey Fredman
(74) *Attorney, Agent, or Firm*—McDonnell Boehnen Hulbert & Berghoff

(57) ABSTRACT

Nucleic acid catalysts, method of screening for variants of nucleic acid catalysts, synthesis of ribozyme libraries and discovery of gene sequences are described.

24 Claims, 23 Drawing Sheets

OTHER PUBLICATIONS

Christoffersen and Marr, "Ribozymes as Human Therapeutic Agents," *J. Med. Chem.* 38(12):2023–2037 (1995).

Cload and Schepartz, "Polyether Tethered Oligonucleotide Probes," *J. Am. Chem. Soc.* 113:6324–6326 (1991).

Couture and Stinchcomb, "Anti–gene Therapy: the Use of Ribozymes to Inhibit Gene Function," *TIG*, 12(12):510 (1996).

Couture et al., "Mutational analysis of conserved nucleotides in a self–splicing group I intron," *J. Mol. Biol.* 215:345–358 (1990).

Daniels et al., "Two Competing Pathways for Self–splicing by Group II Introns: A Quantitative Analysis of in Vitro Reaction Rates and Products," *J. Mol. Biol.* 256:31–49 (1996).

Dropulic et al., "Functional Characterization of a U5 Ribozyme: Intracellular Suppression of Human Immunodeficiency Virus Type I Expression," *Journal of Virology* 66(3):1432–1441 (1992).

Durand et al., "Circular Dichroism Studies of an Oligodeoxyribonucleotide Containing a Hairpin Loop Made of Hexaethylene Glycol Chain: Conformation and Stability," *Nucleic Acids Research* 18:6353–6359 (1990).

Elroy–Stein et al., "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Ferentz and Verdine, "Disulfied Cross–Linked Oligonucleotides," *J. Am. Chem. Soc.* 113:4000–4002 (1991).

Forster and Altman, "External Guide Sequences for an RNA Enzyme," *Science* 249:783–786 (1990).

Forster et al., "Self–cleavage of Plus and Minus RNAs of a Virusoid and a Structural Model for the Active Sites," *Cell* 49:211–220 (1987).

Gao et al., "Cytoplasmic Expression of a Reporter Gene by Co–Delivery of T7 RNA Polymerase and T7 Promoter Sequence with Cationic Liposomes," *Nucleic Acids Research* 21(12):2867–2872 (1993).

Gold et al., "Diversity of oligonucleotide functions," *Annu. Rev. Biochem.* 64:763–797 (1995).

Grasby et al., "Purine Functional Groups in Essential Residues of Hairpin Ribozyme Required for Catalytic Cleavage of RNA," *Biochemistry* 34:4068–4076 (1995).

Griffin, Jr., et al., "Group II Intron Ribozymes that Cleave DNA and RNA Linkages with Similar Efficiency, and Lack Contacts with Substrate 2'–Hydroxyl Groups," *Chemistry & Biology* 2(11):761–770 (1995).

Guo et al., "Eficent Trans–Cleavage of a Stem–Loop RNA Substrate by a Ribozyme Derived from Neurospora VS RNA," *EMBO J.* 14(2):368–376 (1995).

Hampel et al., "'Hairpin' Catalytic RNA Model: Evidence for Helices and Sequence Requirement for Substrate RNA," *Nucleic Acids Research* 18(2):299–304 (1990).

Harris et al., "Identification of phosphates involved in catalysis by the ribozyme RNase P RNA," *RNA* 1:210–218 (1995).

Haseloff et al., "Simple RNA Enzymes with New and Highly Specific Endoribonuclease Activities," *Nature* 334:585–591 (1988).

Hegg et al., "Kinetics and thermodynamics of intermolecular catalysis by hairpin ribozymes," *Biochemistry* 34:15813–15828 (1995).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159–10171 (1990).

Herschlag and Cech, "Catalysis of RNA Cleavage by the *Tetrahymena thermophila* Ribozyme. 2. Kinetic Description of the Reaction of an RNA Substrate That Forms a Mismatch at the Active Site," *Biochemistry* 29:10172–10180 (1990).

Ishizaka et al., "Isolation of Active Ribozymes from an RNA Pool of Random Sequences Using an Anchored Substrate RNA," *Biochemical and Biophysical Research Communication* 214(2):403–409 (1995).

Izant et al., "Constitutive and Conditional Suppression of Exogenous and Endogenous Genes by Anti–Sense RNA," *Science* 229:345–352 (1985).

Jarvis et al., "Inhibition of Vascular Smooth Muscle Cell proliferation by Ribozymes that Cleave c–myb mRNA," *RNA* 2:419–428 (1996).

Jäschke et al., "Automated Incorporation of Polyethylene Glycol into Synthetic Oligonucleotides," *Tetrahedron Letters* 34:301–304 (1993) (Jasachke).

Jeffries et al., "A Catalytic 13–mer Ribozyme," *Nucleic Acids Research* 17(4):1371–1377 (1989).

Joseph and Burke, "Optimization of an Anti–HIV Hairpin Ribozyme by in Vitro Selection," *J. Biol. Chem.* 268:24515–24518 (1993).

Joseph et al., "Substrate selection rules for hairpin ribozyme determined by in vitro selection, mutation, and analysis of mismatched substrates," *Genes & Development* 7:130–138 (1993).

Joyce et al., "Amplification, mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–ras Ribozyme," *Antisense Research & Development* 2:3–15 (1992).

Knitt et al., "ph Dependencies of the Tetrahymena Ribozyme Reveal an Unconvential Origin of an Apparent $pK_a$," *Biochemistry* 35:1560–1570 (1996).

Kumar and Ellington, "Artificial evolution and natural ribozymes," *FASEB J.* 1183–1195 (1995).

Li et al., "Thermodynamic and Activation Parameters for Binding of a Pyrene–Labeled Substrate by the Tetrahymena Ribozyme: Docking is Not Diffusion–Controlled and is Driven by a Favorable Entropy Change," *Biochemistry* 34:14394–14399 (1995).

Lieber and Strauss, Selection of Efficient Cleavage Sites in Target RNAs by Using a Ribozyme Expression Library, *Mol. Cellular Biol.* 15:540–551 (1995).

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA," *Nucleic Acids Research* 22(12):2183–2196 (1994).

Lisacek et al., "Automatic Identification of Group I Intron Cores in Genomic DNA Sequences," *J. Mol. Biol.* 235:1206–1217 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Long and Uhlenbeck, "Kinetic characterization of intramolecular and intermolecular hammerhead RNAs with stem II deletions," *Proc. Natl. Acad. Sci. U.S.A.* 90:8000–8004 (1993).

Ma et al., "Design and Synthesis of RNA Miniduplexes via a Synthetic Linker Approach," *Biochemistry* 32:1751–1758 (1993).

Ma et al., "Design and Synthesis of RNA Miniduplexes via a Synthetic Linker Approach. 2. Generation of Covalently Closed, Double–Stranded Cyclic HIV–1 TAR RNA Analogs with High Tat–Binding Affinity," *Nucleic Acids Research* 21:2585–2589 (1993).

McCurdy et al., "Deoxyoligonucleotides with Inverted Polarity: Synthesis and Use in Triple–Helix Formation" *Nucleosides & Nucleotides* 10:287–290 (1991).

McGarry et al., "Inhibition of Heat Shock Protein Synthesis by Heat–Inducible Antisense RNA," *Proc. Natl. Acad. Sci. USA* 83:399–403 (1986).

Michel et al., "Structure and activities of group II introns," *Annu. Rev. Biochem.* 64:435–461 (1995).

Michel and Westhof, "Slippery substrates," *Nat. Struct. Biol.* 1:5–7 (1994).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan et al., "Synthesis of Small RNAs Using T7 RNA Polymerase," *Methods Enzymol.* 180:51–62 (1989).

Mohr et al., "A tyrosyl–tRNA synthetase can function similarly to an RNA structure in the Tetrahymena ribozyme," *Nature* 370:147–150 (1994).

Nakamaye et al., "AUA–cleaving hammerhead ribozymes: Attempted selection for improved cleavage," *Biochemistry* 33:1271–1277 (1994).

Nathans and Smith, "Restriction Endonucleases in the Analysis and Restructuring of DNA Molecules," *Ann. Rev. Biochem.* 44:273–293 (1975).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

Orgel, "Selection in vitro," *Proc. R. Soc. London B.* 205:435–442 (1979).

Pan et al., "Probing of tertiary interactions in RNA: 2'–Hydroxyl–base contacts between the Rnase P and pre–tRNA," *Proc. Natl. Acad. Sci. USA* 92:12510–12514 (1995).

Perreault et al., "Mixed Deoxyribo– and Ribo–Oligonucleotides with Catalytic Activity," *Nature* 344:565–567 (1990).

Perrota et al., "Core sequences and a cleavage site wobble pair required for HDV antigenomic ribozyme self–cleavage," *Nucleic Acids Research* 24:1314–1321 (1996).

Perrotta and Been, "A pseudoknot–like structure required for efficeint self–cleavage of hepatitis delta virus RNA," *Nature* 350:434–436 (1991).

Perrotta et al., "Cleavage of Oligoribonucleotides by a Ribozyme Derived from the Hepatitis Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Puttaraju et al., "A Circular Trans–Acting Hepatitis Delta Virus Ribozyme," *Nucleic Acids Research* 21(18):4253–4258 (1993).

Pyle et al., "Building a kinetic framework for group II intron ribozyme activity: Quantitation of interdomain binding and reaction rate," *Biochemistry* 33:2716–2725 (1994).

Richardson and Schepartz, "Tethered Oligonucleotide Probes. A Strategy for the Recognition of Structured RNA," *J. Am. Chem. Soc.* 113:5109–5111 (1991).

Robertson et al., "Purification and Properties of a Specific *Escherichia coli* Riobnuclease which Cleaves a Tyrosine Transfer Ribonucleic Acid Precursor," *J. Biol. Chem.* 247:5243–5251 (1972).

Ruffner et al., "Sequence Requirements of the Hammerhead RNA Self–Cleavage Reaction," *Biochemistry* 29:10695–10702 (1990).

Sarver et al., "Ribozymes as Potential Anti–HIV–1 Therapeutic Agents" *Science* 247:1222–1225 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical Synthesis of Biologically Active Oligoribonucleotides using cyanoethyl Protected Ribonuclease Phosphoramidites," *Nucl Acids Res.* 18(18):5433–5441 (1990).

Schmidt et al., "Base and sugar requirements for RNA cleavage of essential nucleoside residues in internal loop B of the hairpin ribozyme: implications for secondary structure," *Nucleic Acids Research* 24:573–581 (1996).

Strobel et al., "Exocyclic Amine of the Conserved G•U Pair at the Cleavage Site of the Tetrahymena Ribozyme Contributes to 5'–Splice Site Selection and Transition State Stabilization," *Biochemistry* 35:1201–1211 (1996).

Strobel et al., "Minor Groove Recognition of the Conserved G•U Pair at the Tetrahymena Ribozyme Reaction Site," *Science* 267:675–679 (1995).

Sullenger and Cech, "Ribozyme–mediated repair of defective mRNA by targeted trans–splicing," *Nature* 371:619–622 (1994).

Sullenger et al., "Tethering Ribozymes to a Retroviral Packaging Signal for Destruction of Viral RNA," *Science* 262:1566–1569 (1993).

Szostak et al., "In vitro selection of functional RNA sequences," *RNA World*, p. 511 (1993).

Szostak, "In Vitro Genetics," *TIBS* 17:89–93 (1993).

Szostak, Redesigning the Molecules of Life: Conference Papers of the International Symposium on Biorganic Chemistry ed. Benner Springer–Verlag (1988).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19(19):5125–5130 (1991).

Thompson et al., "Improved Accumulation and Activity of Ribozymes Expressed from a tRNA–based RNA Polymerase III Promoter," *Nucleic Acids Research* 23(12):2259–2268 (1995).

Uhlenbeck, "A Small Catalytic Oligoribonucleotide," *Nucleic Acids Research* 23(12):2259–2268 (1995).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of and *Escherichia coli* Formylmethionine tRNA," *J. Am. Chem. Soc.* 109(25):7845–7854 (1987).

Usman et al., "Chemical Modification of Hammerhead Ribozymes: Activity and Nuclease Resistance," *Nucleic Acids Symposium Series* 31:163–164 (1994).

Usman et al., "Exploiting the Chemical Synthesis of RNA," *TIBS* 17:334–339 (1992).

Vaish et al., "Isolation of hammerhead ribozymes with altered core sequences by in vitro selection," Biochemistry 36:6495–6501 (1997).

Ventura et al., "Activation of HIV–Specific Ribozyme Activity by Self–Cleavage," *Nucleic Acids Research* 21(14):3249–3255 (1993).

Weerashinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65(10):5531–5534 (1991).

Wincott et al., "Synthesis, Deprotection, Analysis and Purification of RNA and Ribozymes," *Nucleic Acids Research* 23(14):2677–2684 (1995).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Yuan et al., "Targeted cleavage of mRNA by human RNase P," *Proc. Natl. Acad. Sci. USA* 89:8006–8010 (1992).

Zarrinkar and Williamson, "The P9.1–P9.2 peripheral extension helps guide folding of the Tetrahymena ribozyme," *Nucleic Acids Research* 24:854–858 (1996).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10(9):4529–4537 (1990).

Zimmerly et al., "A Group II Intron RNA is a Catalytic Component of a DNA Endonuclease Involved in Intron Mobility," *Cell* 83:529–538 (1995).

\* cited by examiner

Figure 1: Hammerhead Ribozyme

Figure 2. Hammerhead Ribozyme Substrate Motifs

Figure 3: Hairpin Ribozyme

Hepatitis Delta Virus (HDV) Ribozyme

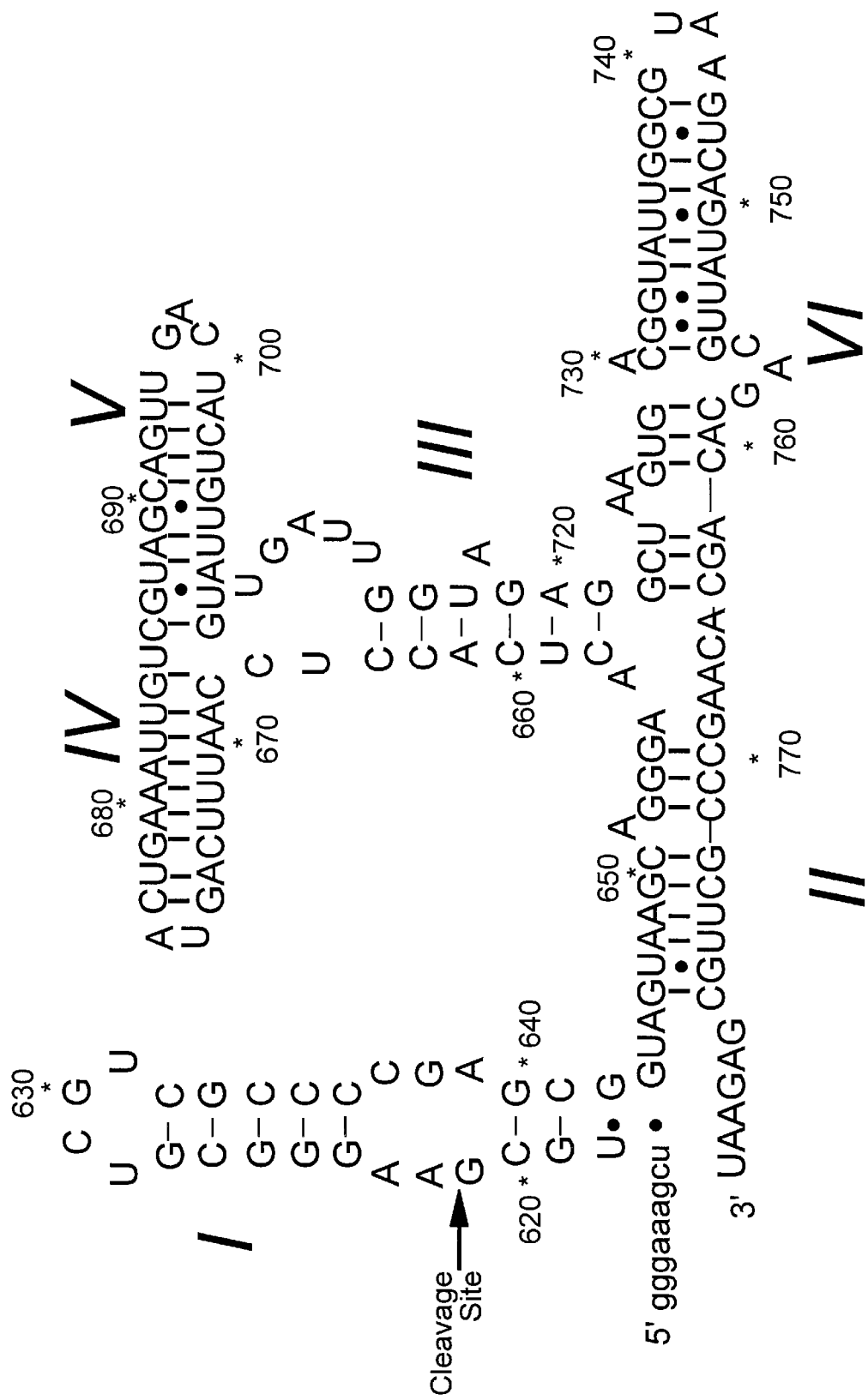
Figure 5. Neurospora vs Ribozyme

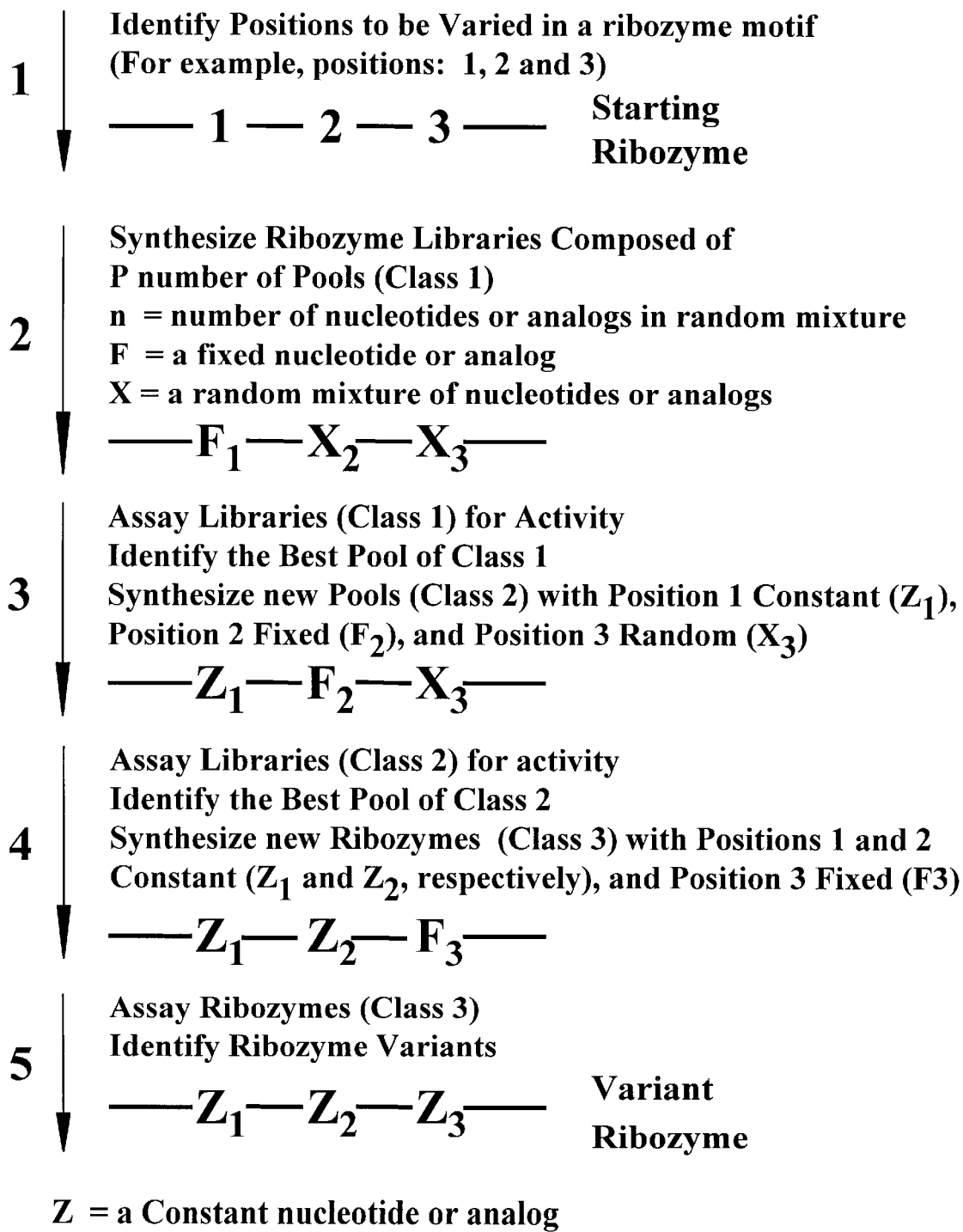
Figure 6: A Combinatorial Approach to the Screening of Ribozyme Variants

Figure 7: Starting Ribozyme Motif for Variation (Hammerhead Motif/HH Motif)
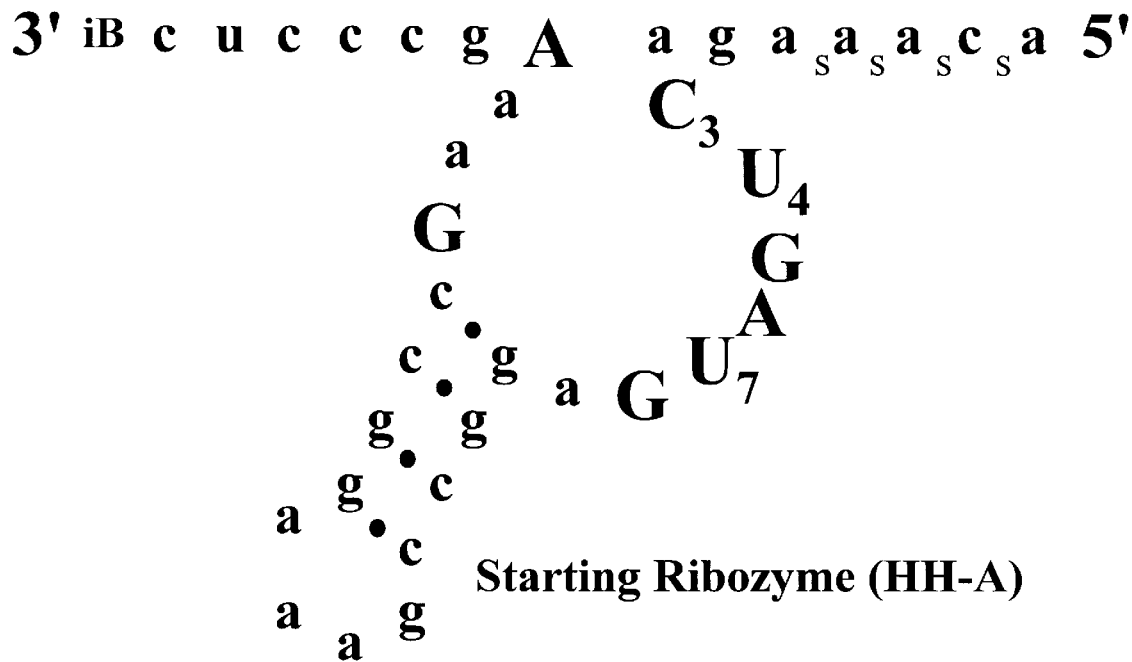
Starting Ribozyme (HH-A)
Positions 3, 4 and 7 are being varied in one example
3'─────────── $U_7$ ──── $U_4$ $C_3$ ─── 5'
3' ───────────── $U_{24}$ ──── $U_{27}$ $C_{28}$ ─── 5'

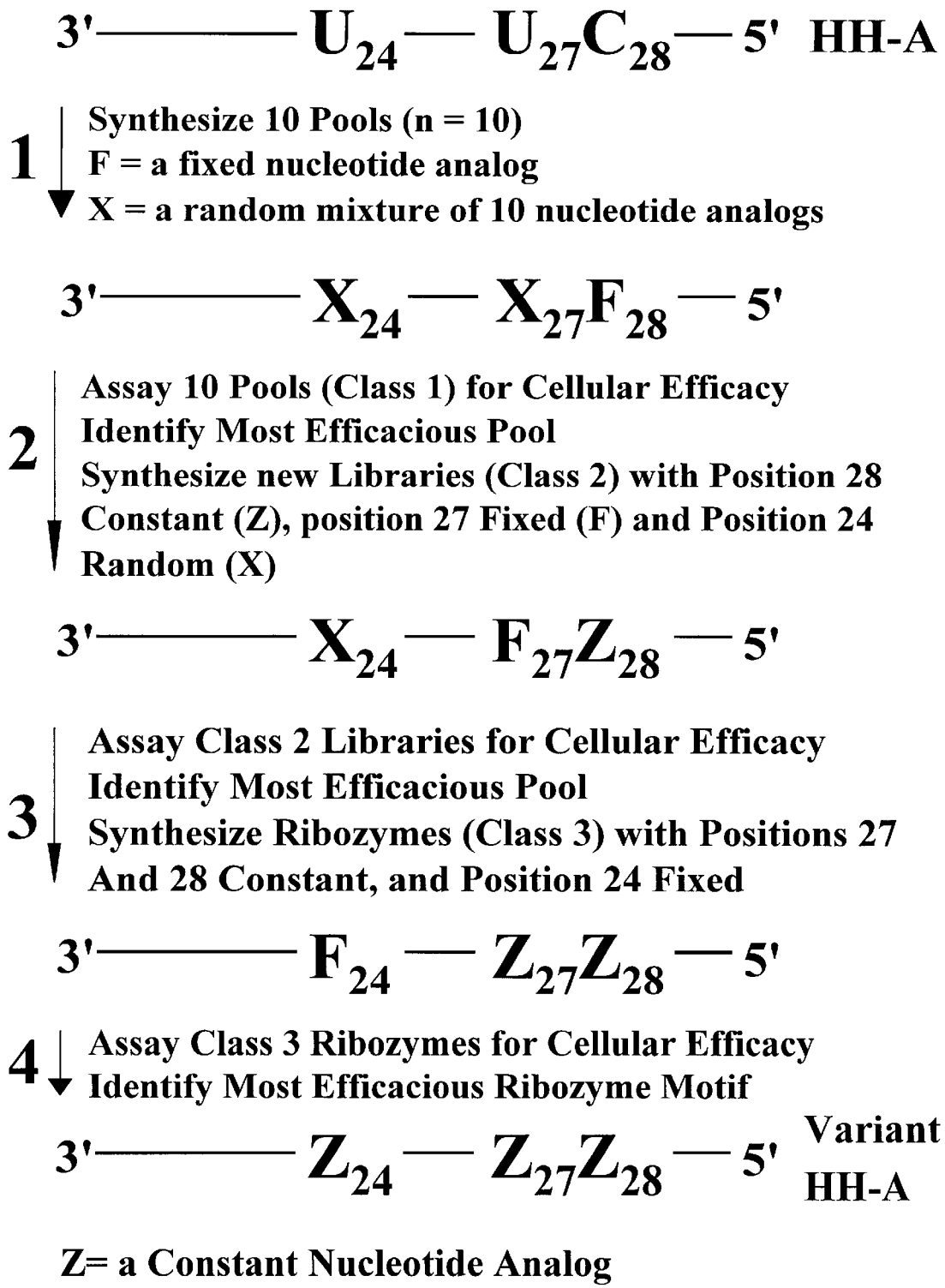
Figure 8 : Screening for Variants of HH-A Ribozyme

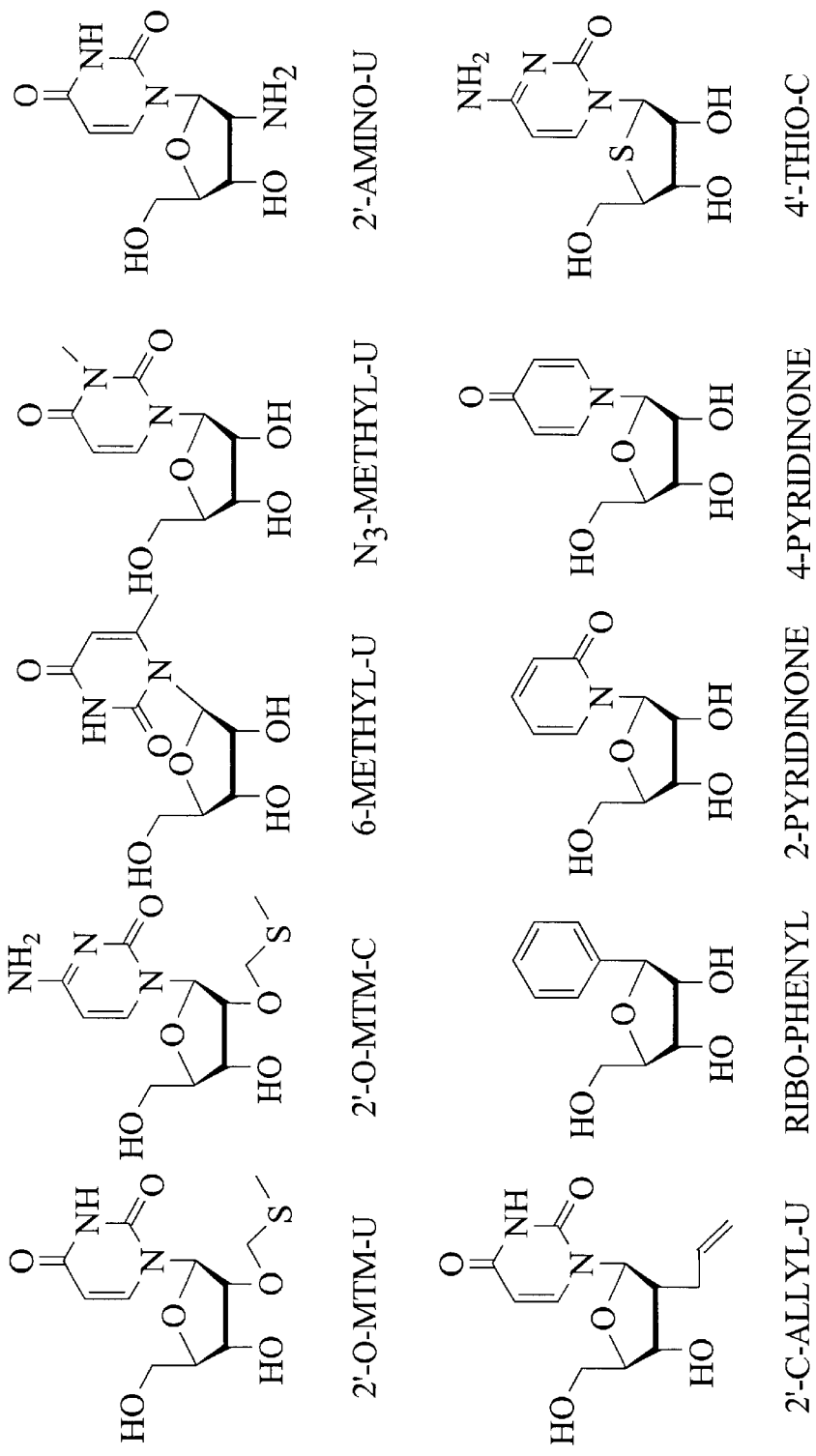
Figure 9: Examples of Nucleotide Analogs (n) Used in Library (Class 1 Pool) Construction

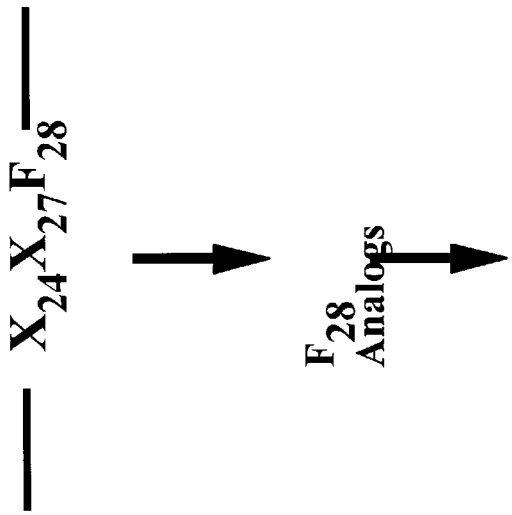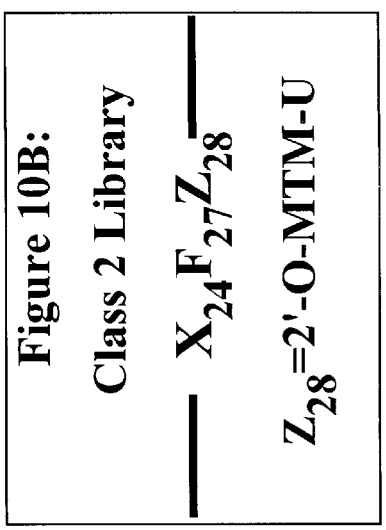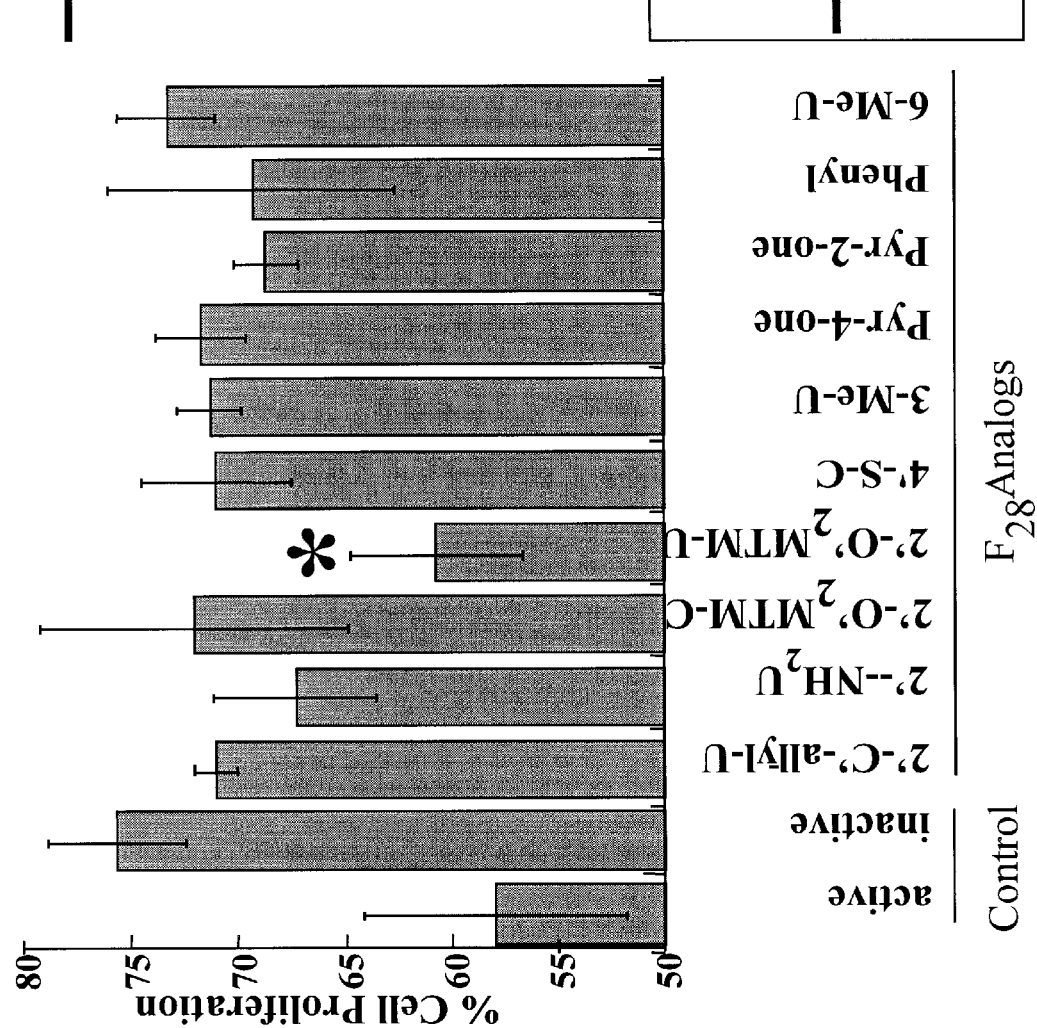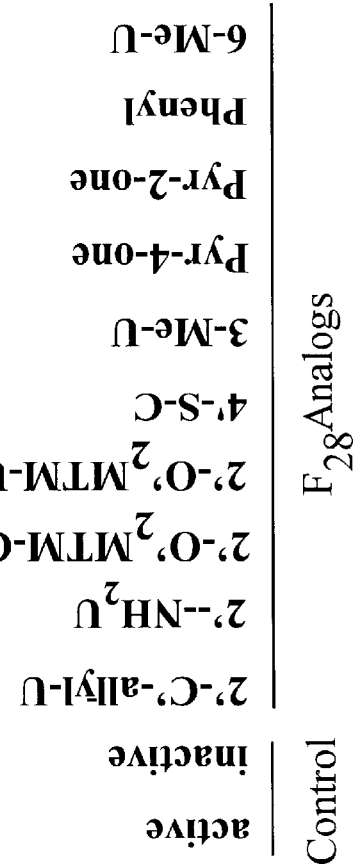

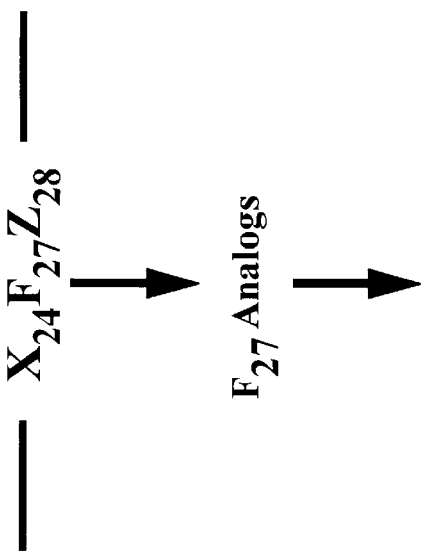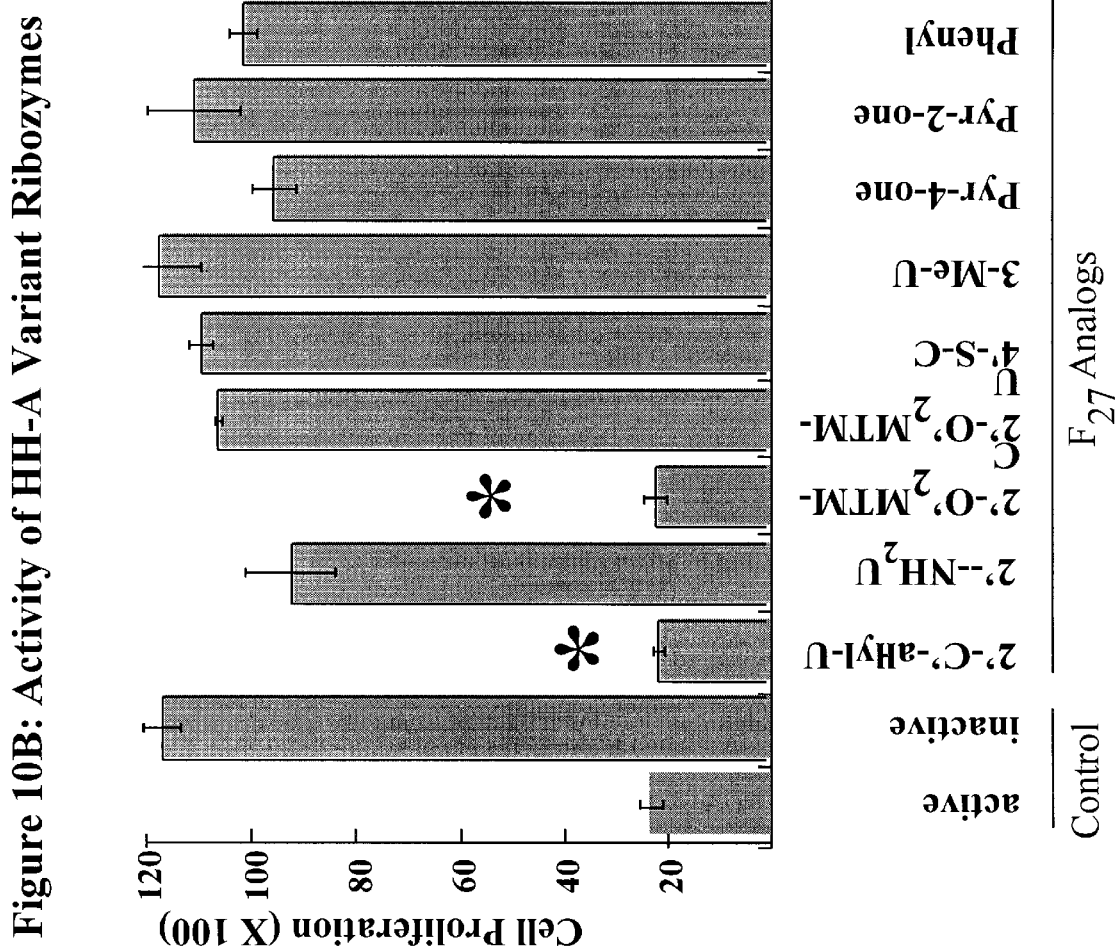

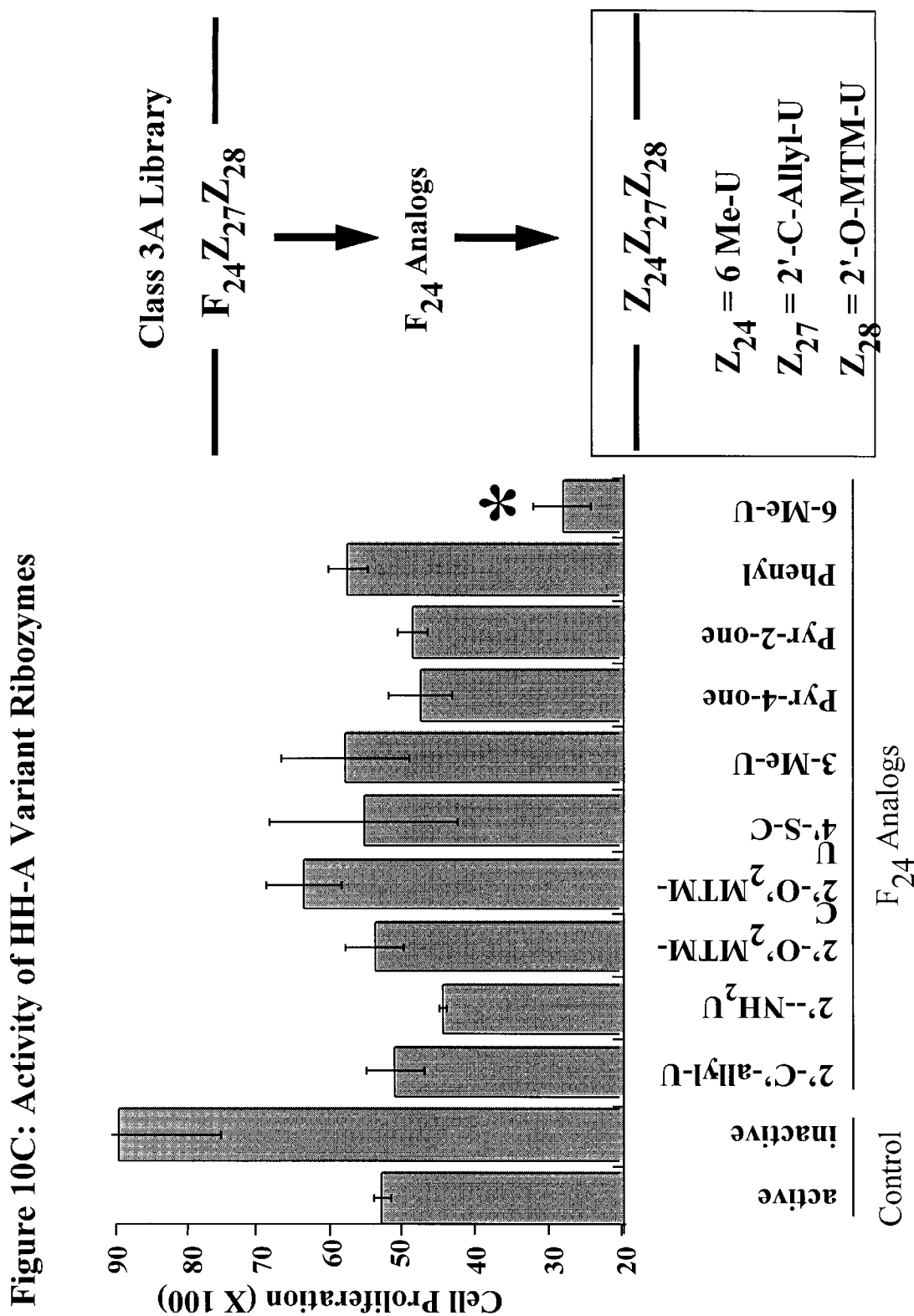
Figure 10C: Activity of HH-A Variant Ribozymes

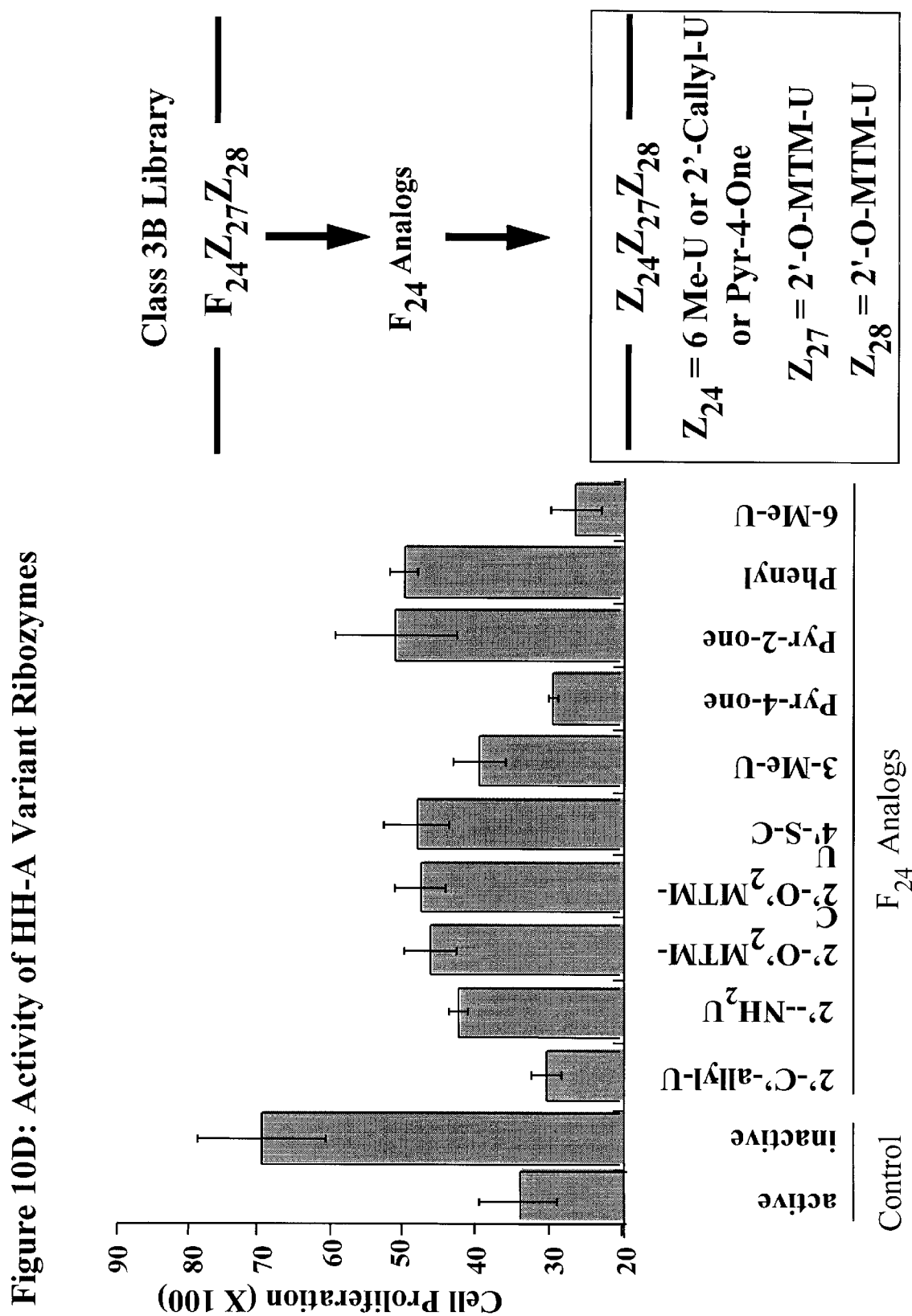
Figure 10D: Activity of HH-A Variant Ribozymes

Figure 11A: HH-A Variants

HH-A1

```
                      a g a a a c a
                           s s s s
iB c u c c c g A   a Z3      Z4  G
                 a           G   A
                 G         c•g Z7
                 c•g g a G
                g•c
              a   g
             a      a
```

Z3 = 2'-O-MTM-U
Z4 = 2'-C-Allyl-U
Z7 = 6-Methyl-U

HH-A2

```
                      a g a a a c a
                           s s s s
iB c u c c c g A   a Z3      Z4  G
                 a           G   A
                 G         c•g Z7
                 c•g g a G
                g•c
              a   g
             a      a
```

Z3 = 2'-O-MTM-U
Z4 = 2'-O-MTM-C
Z7 = 6-Methyl-U

HH-A3

```
                      a g a a a c a
                           s s s s
iB c u c c c g A   a Z3      Z4  G
                 a           G   A
                 G         c•g Z7
                 c•g g a G
                g•c
              a   g
             a      a
```

Z3 = 2'-O-MTM-U
Z4 = 2'-O-MTM-C
Z7 = 2'-C-Allyl-U

HH-A4

```
                      a g a a a c a
                           s s s s
iB c u c c c g A   a Z3      Z4  G
                 a           G   A
                 G         c•g Z7
                 c•g g a G
                g•c
              a   g
             a      a
```

Z3 = 2'-O-MTM-U
Z4 = 2'-O-MTM-C
Z7 = Pyridin-4-One

Figure 11B: Novel Ribozyme Variants 1 and 2

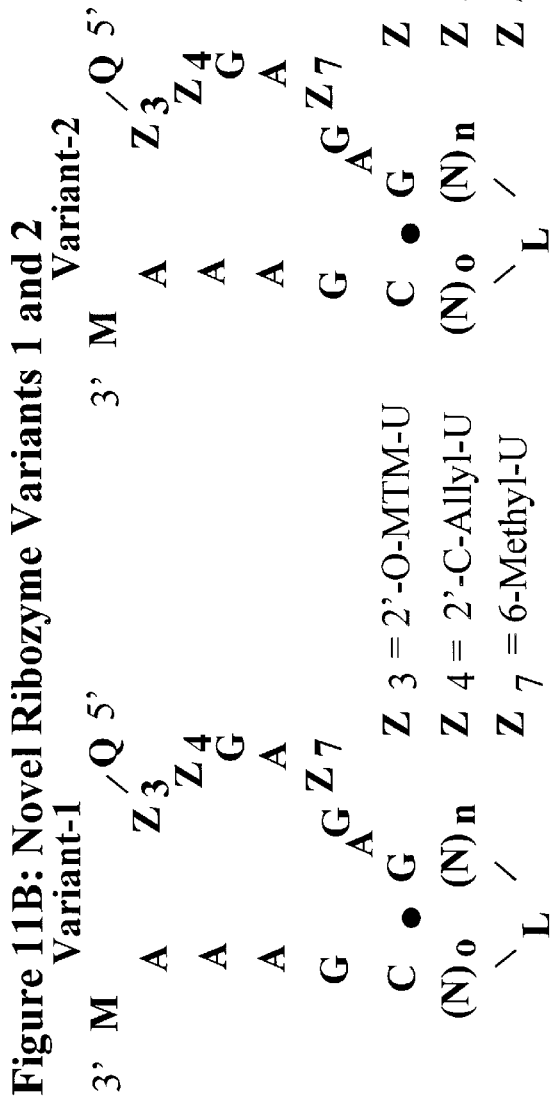

N = independently a nucleotide or a non-nucleotide linker, which may be same or different; M and Q are independently oligonucleotides of length sufficient to stably interact (e.g., by forming hydrogen bonds with complementary nucleotides in the target) with a target nucleic acid molecule (the target can be an RNA, DNA or RNA/DNA mixed polymers);

o and n are integers greater than or equal to 1 and preferably less than about 100, where in if (N)o and (N)n are nucleotides, (N)o and (N)n are optionally able to interact by hydrogen bond interaction;

L is a linker which may be present or absent (i.e., the molecule is assembled from two separate molecules), but when present, is a nucleotide and/or a non-nucleotide linker, which may be a single-stranded and/or double-stranded region; and represents a chemical linkage(e.g. a phosphate ester linkage, amide linkage or others known in the art).

A, C, U and G represent adenosine, cytidine, uridine and guanosine nucleotides, respectively, which may be modified or unmodified.

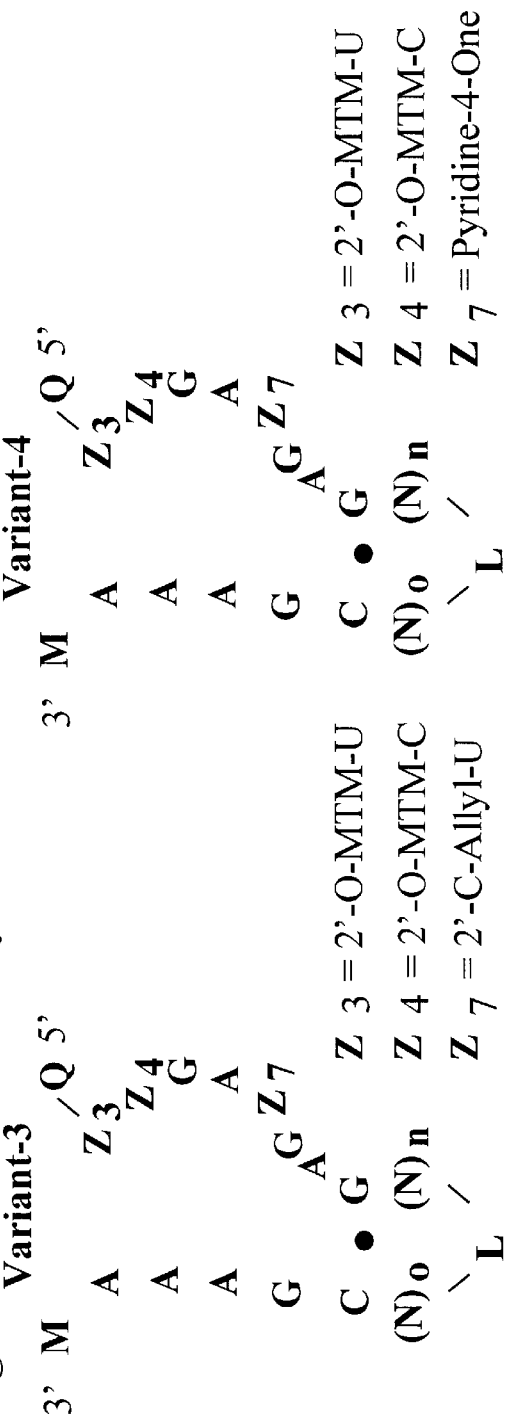

Figure 11C: Novel Ribozyme Variants 3 and 4

N = independently a nucleotide or a non-nucleotide linker, which may be same or different;
M and Q are independently oligonucleotides of length sufficient to stably interact (*e.g.*, by forming hydrogen bonds with complementary nucleotides in the target) with a target nucleic acid molecule (the target can be an RNA, DNA or RNA/DNA mixed polymers);
o and n are integers greater than or equal to 1 and preferably less than about 100, where in if (N)o and (N)n are nucleotides,
(N)o and (N)n are optionally able to interact by hydrogen bond interaction;
L is a linker which may be present or absent (*i.e.*, the molecule is assembled from two separate molecules), but when present, is a nucleotide and/or a non-nucleotide linker, which may be a single-stranded and/or double-stranded region; and represents a chemical linkage(*e.g.* a phosphate ester linkage, amide linkage or others known in the art).
A, C, U and G represent adenosine, cytidine, uridine and guanosine nucleotides, respectively, which may be modified or unmodified.

Figure 12: Formula for a novel Ribozyme Motif

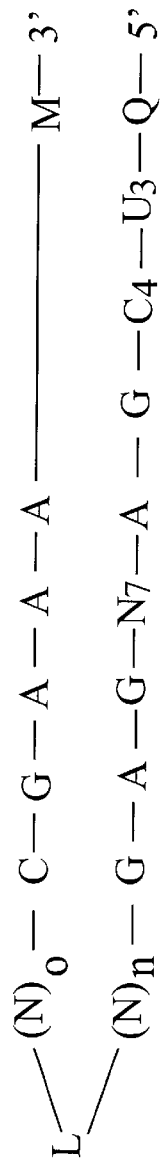

$$L \diagup\!\!\!\diagdown \begin{matrix} (N)_o - C - G - A - A \phantom{XXXXXXXX} M-3' \\ (N)_n - G - A - G - N_7 - A - G - C_4 - U_3 - Q-5' \end{matrix}$$

N = independently a nucleotide or a non-nucleotide linker, which may be same or different;

M and Q are independently oligonucleotides of length sufficient to stably interact (e.g., by forming hydrogen bonds with complementary nucleotides in the target) with a target nucleic acid molecule (the target can be an RNA, DNA or RNA/DNA mixed polymers);

o and n are integers greater than or equal to 1 and preferably less than about 100, where in if (N)o and (N)n are nucleotides, (N)o and (N)n are optionally able to interact by hydrogen bond interaction;

L is a linker which may be present or absent (i.e., the molecule is assembled from two separate molecules), but when present, is a nucleotide and/or a non-nucleotide linker, which may be a single-stranded and/or double-stranded region; and represents a chemical linkage(e.g. a phosphate ester linkage, amide linkage or others known in the art).

A, C, U and G represent adenosine, cytidine, uridine and guanosine nucleotides, respectively, which may be modified or unmodified.

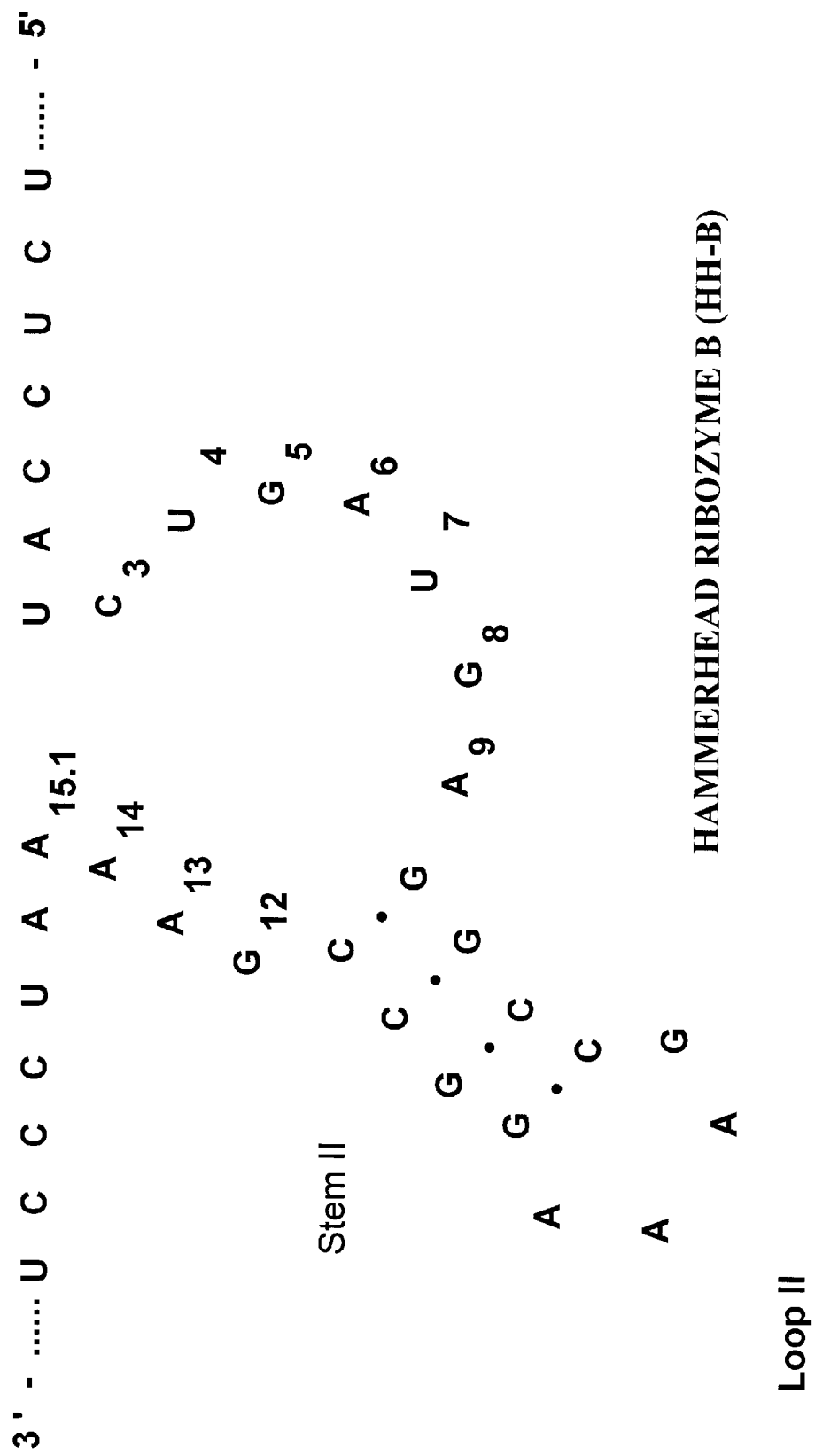
Figure 13: Starting Ribozyme motif for Loop Variation

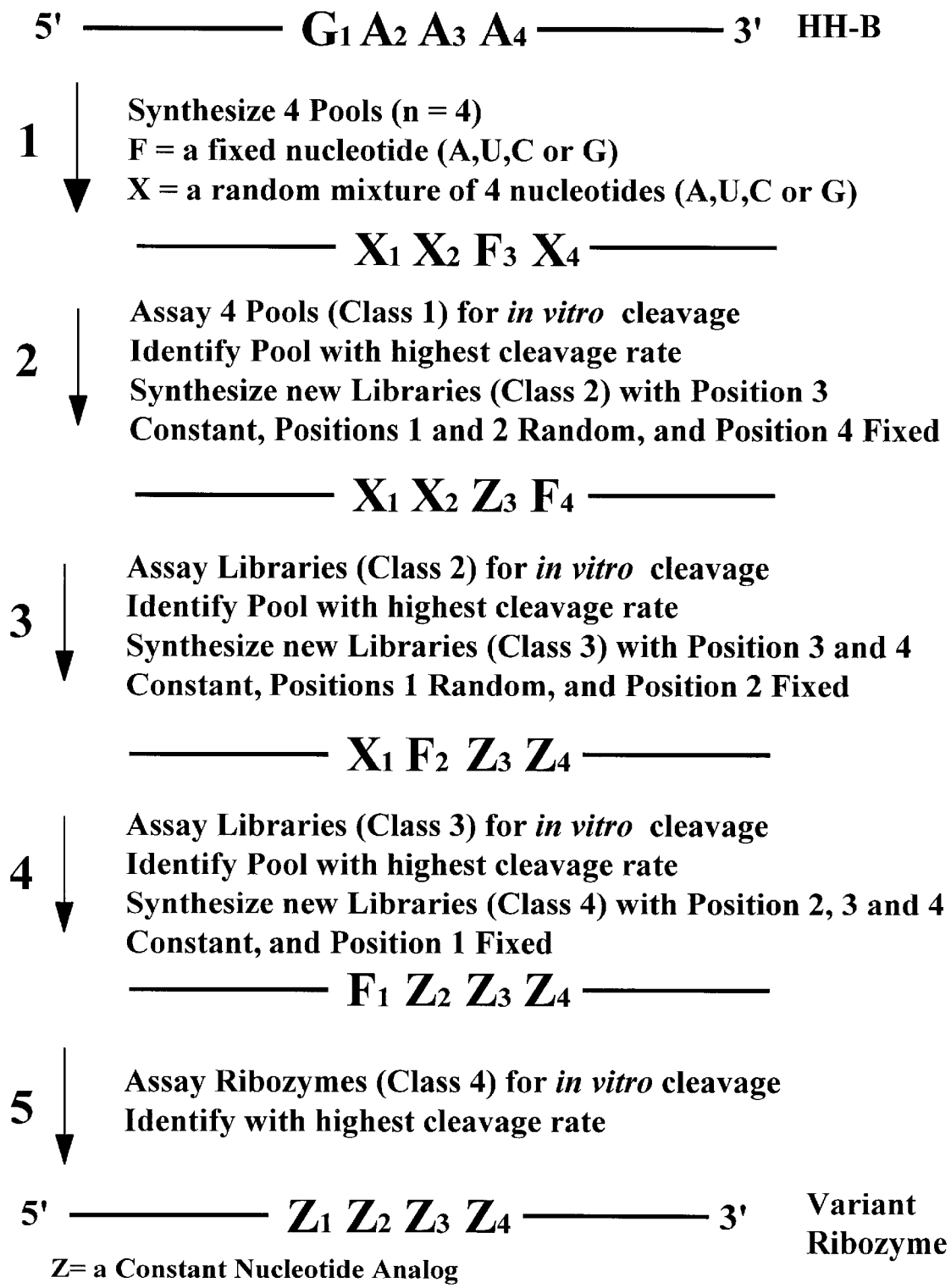

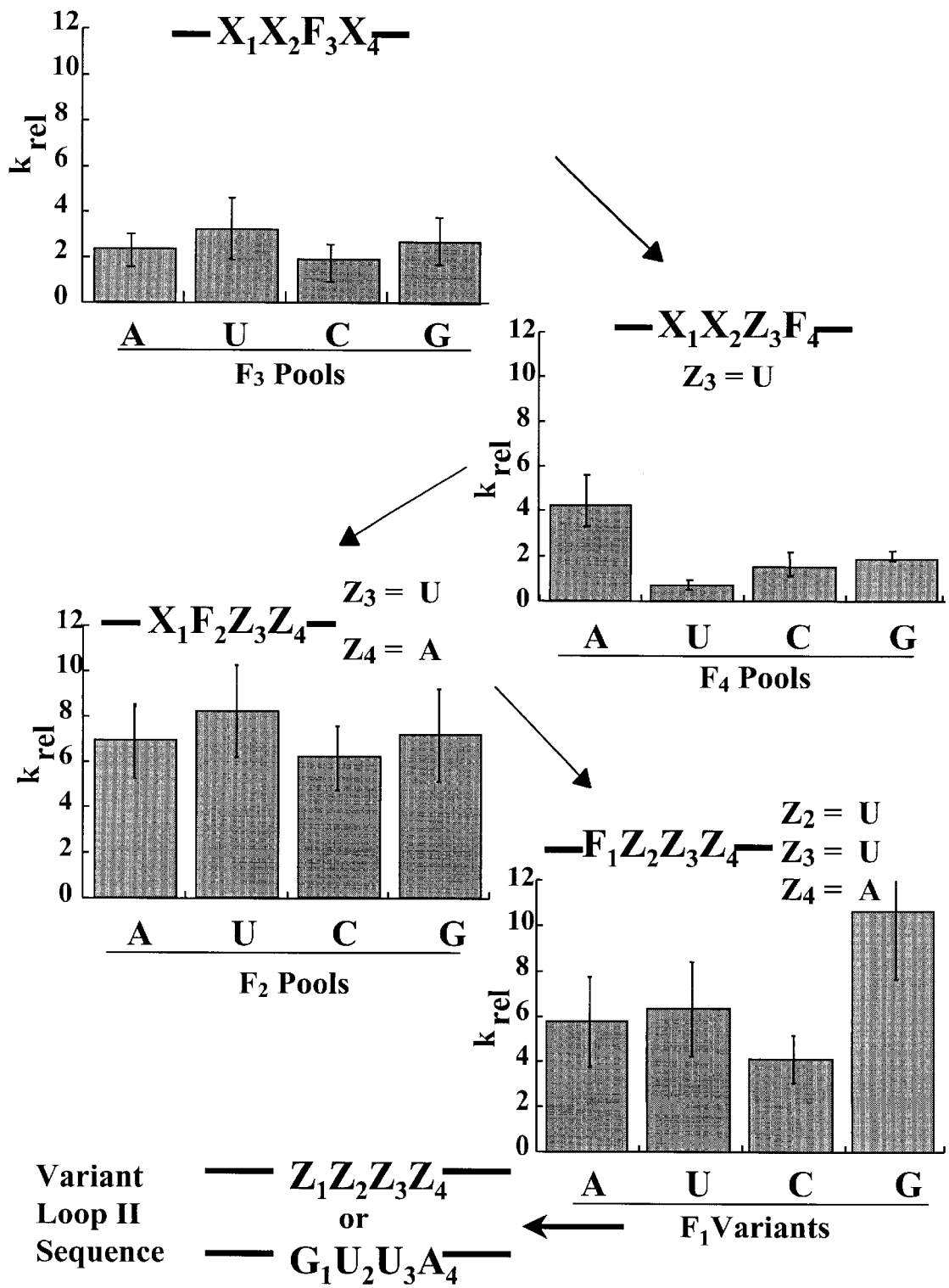
Figure 15: Activity of HH-B Variant Ribozymes

Figure 16: RNA Cleavage by Loop II Variant HH-B Ribozyme
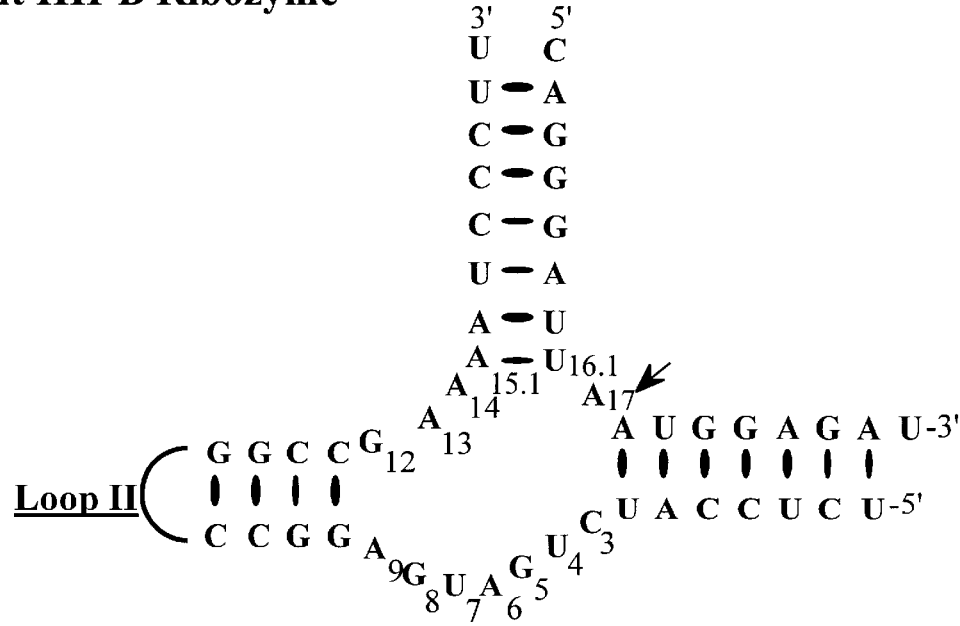
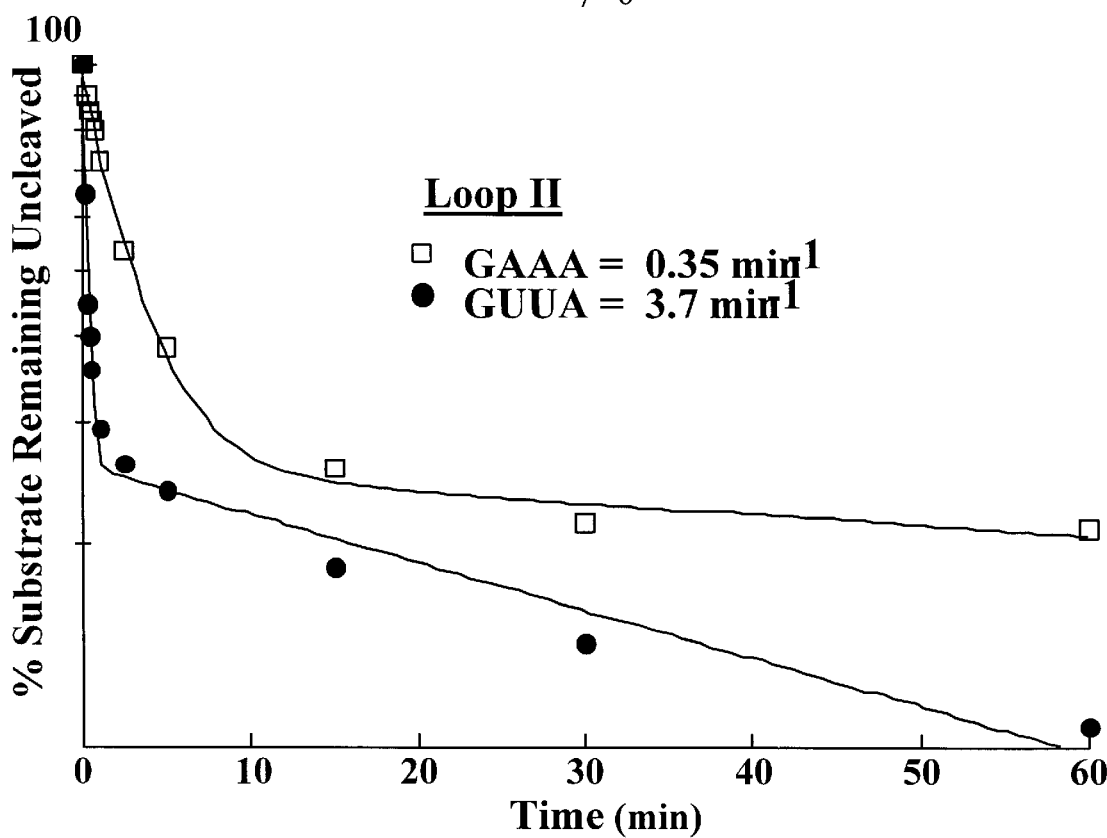

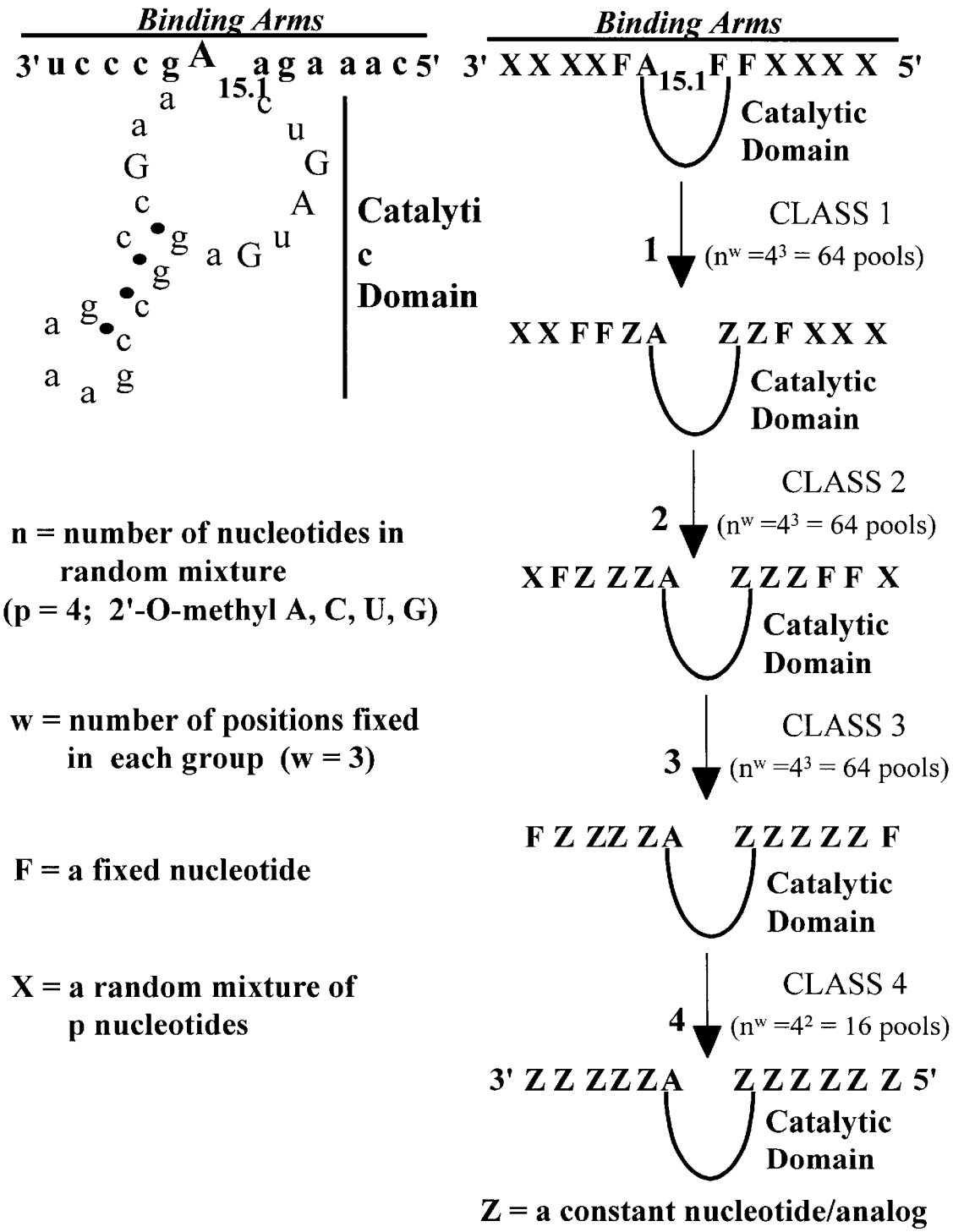
Figure 17: Screening for Ribozyme Binding Arm Sequence Variants-Target Discovery Hammerhead Ribozyme Model System

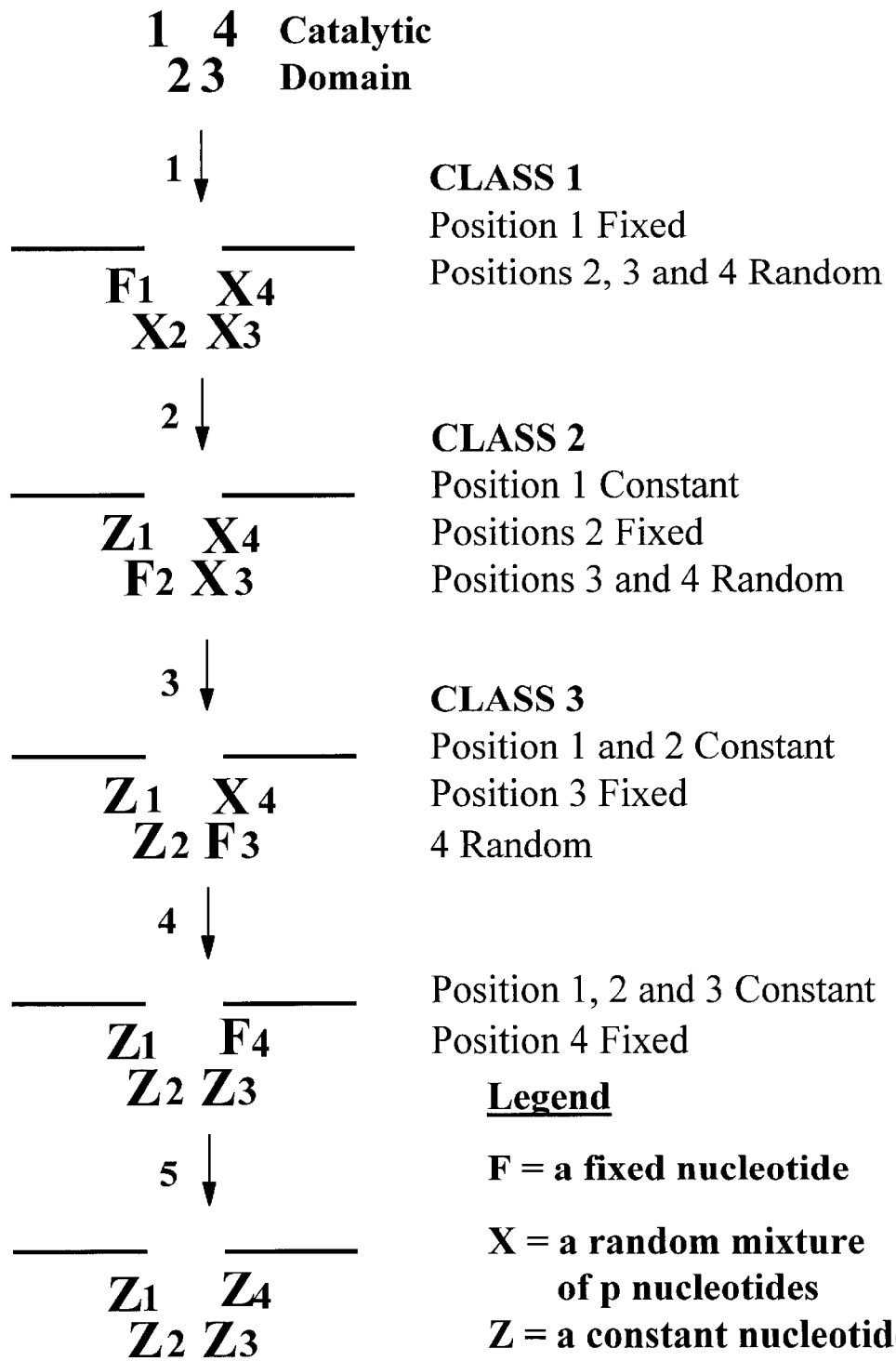
Figure 18: Screening for Ribozyme Catalytic Domains

METHOD FOR SCREENING NUCLEIC ACID CATALYSTS

This application claims the benefit of Alex Burgin, et al. U.S. Provisional Application No. 60/049,002, entitled "Method for Screening Nucleic Acid Catalysts", filed Jun. 9, 1997, incorporated herein by reference in its entirely, including any drawings and figures.

BACKGROUND OF THE INVENTION

This invention relates to nucleic acid molecules with catalytic activity and derivatives thereof.

The following is a brief description of catalytic acid molecules. This summary is not meant to be complete but is provided only for understanding of the invention that follows. This summary is not an admission that all of the work described below is prior art to the claimed invention.

Catalytic nucleic acid molecules (ribozymes) are nuclei acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech 260 JAMA 3030, 1988; and Jefferies et al., 17 Nucleic Acids Research 1371, 1989). Any nucleotide base-comprising molecule having the ability to repeatedly act on one or more types of molecules, including but not limited to enzymatic nucleic acid molecules. By way of example but not limitation, such molecules, peptides, or other polymers, and those that are able to cause the polymerization of such nucleic acids and other polymers. Specifically, such molecules include ribozymes, DNAzymes, external guide sequences and the like. It is expected that such molecules will also include modified nucleotides compared to standard nucleotides found in DNA and RNA.

Because of their sequence-specificity, trans-leaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

There are at least seven basic varieties of naturally-occurring enzymatic RNAs. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

In addition, several in vitro selection (evolution) strategies (Orgel, 1979, *Proc. R. Soc.* London, B 205, 435) have been used to evolve new nucleic acid catalysts capable of catalyzing a variety of reactions, such as cleavage and ligation of phosphodiester linkages and amide linkages, (Joyce, 1989, *Gene,* 82, 83–87; Beaudry at al., 1992, *Science* 257, 635–641; Joyce, 1992, *Scientific American* 267, 90–97; Breaker et al., 1994, TIBTECH 12, 268; Bartel et al.,1993, *Science* 261:1411–1418; Szostak, 1993, TIBS 17, 89–93; Kumar et al, 1995, *FASEB J.,* 9, 1183; Breaker, 1996, *Curr. Op. Biotech.,* 7, 442; Breaker, 1997, *Nature Biotech.* 15, 427).

There are several reports that describe the use of a variety of in vitro and in vivo selection strategies to study structure and function of catalytic nucleic acid molecules (Campbell et al., 1995, RNA 1, 598; Joyce 1989, *Gene,* 82,83; Lieber at al., 1995, *Mol Cell Biol.* 15, 540; Lieber et al., International PCT Publication No. WO 96/01314; Szostak 1988, in *Redesigning the Molecules of Life,* Ed. S. A. Benner, pp 87, Springer-Verlag, Germany; Kramer et al., U.S. Pat. No. 5,616,459; Joyce, U.S. Pat. No. 5,595,873; Szostak et al., U.S. Pat. No. 5,631,146).

The enzymatic nature of a ribozyme is advantageous over other technologies, since the effective concentration of ribozyme necessary to effect a therapeutic treatment is generally lower than that of an antisense oligonucleotide. This advantage reflects the ability of the ribozyme to act enzymatically. Thus, a single ribozyme (enzymatic nucleic acid) molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

The development of ribozymes that are optimal for catalytic activity would contribute significantly to any strategy that employs RNA-cleaving ribozymes for the purpose of regulating gene expression. The hammerhead ribozyme functions with a catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) can be 10- to 100-fold slower. In contrast, the RNase P holoenzyme can catalyze pre-tRNA cleavage with a $k_{cat}$ of ~30 min$^{-1}$ under optimal assay conditions. An artificial 'RNA ligase' ribozyme (Bartel et al., supra) has been shown to catalyze the corresponding self-modification reaction with a rate of ~100 min$^{-1}$. In addition, it is known that certain modified hammerhead ribozymes that have substrate binding arms made of DNA catalyze RNA cleavage with multiple turn-over rates that approach 100 min$^{-1}$. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain self-cleaving ribozymes may not be optimized to give maximal catalytic activity, or that entirely new RNA motifs could be made that display significantly faster rates for RNA phosphoester cleavage.

An extensive array of site-directed mutagenesis studies have been conducted with ribozymes such as the hammerhead, hairpin, hepatitis delta virus, group I, group II and others, to probe relationships between nucleotide sequence, chemical composition and catalytic activity. These systematic studies have made clear that most nucleotides in the conserved core of these ribozymes cannot be mutated without significant loss of catalytic activity. In contrast, a combinatorial strategy that simultaneously screens a large pool of mutagenized ribozymes for RNAs that retain catalytic activity could be used more efficiently to define immutable sequences and to identify new ribozyme variants.

Although in vitro selection experiments have been reported with the hammerhead ribozyme (Nakamaye & Eckstein, 1994, *Biochemistry* 33, 1271; Long & Uhlenbeck, 1994, *Proc. Natl. Acad. Sci.,* 91, 6977; Ishizaka et al., 1995, BBRC 214, 403; Vaish et al., 1997, *Biochemistry,* 36, 6495) and Hairpin ribozyme (Berzal et al., 1993, *EMBO, J.,* 12, 2567) none of these efforts have successfully screened for all possible combinations of sequence and chemical variants that encompass the entire catalytic core.

The references cited above are distinct from the presently claimed invention since they do not disclose and/or contemplate the enzymatic nucleic acid molecules and the methods for screening ribozyme variants.

SUMMARY OF THE INVENTION

This invention relates to novel nucleic acid molecules with catalytic activity, which are particularly useful for cleavage of RNA or DNA. The nucleic acid catalysts of the instant invention are distinct from other nucleic acid catalysts known in the art. This invention also relates to a method of screening variants of nucleic acid catalysts using standard nucleotides or modified nucleotides. Applicant has determined an efficient method for screening libraries of catalytic nucleic acid molecules, particularly those with chemical modifications at one or more positions. The method described in this application involves systematic screening of a library or pool of ribozymes with various substitutions at one or more positions and selecting for ribozymes with desired function or characteristic or attribute.

Applicant describes herein, a general combinatorial approach for assaying ribozyme variants based on ribozyme activity and/or a specific "attribute" of a ribozyme, such as the cleavage rate, cellular efficacy, stability, delivery, localization and the like. Variations of this approach also offer the potential for designing novel catalytic oligonucleotides, identifying ribozyme accessible sites within a target, and for identifying new nucleic acid targets for ribozyme-mediated modulation of gene expression.

Other features and advantages of the invention will be apparent from the following description of the preferred embodiments thereof, and from the claims.

DESCRIPTION OF THE PREFERRED EMBODIMENTS

The drawings will first briefly be described.
Drawings

FIG. 1 is a diagrammatic representation of the hammerhead ribozyme domain known in the art. Stem II can be $\geq 2$ base-pair long. Each N is independently any base or non-nucleotide as used herein.

FIG. 2a is a diagrammatic representation of the hammerhead ribozyme domain known in the art. FIG. 2b is a diagrammatic representation of the hammerhead ribozyme as divided by Uhlenbeck (1987, *Nature,* 327, 596–600) into a substrate and enzyme portion; FIG. 2c is a similar diagram showing the hammerhead divided by Haseloff and Gerlach (1988, *Nature,* 334, 585–591) into two portions; and FIG. 2d is a similar diagram showing the hammerhead divided by Jeffries and Symons (1989, *Nucl. Acids. Res.,* 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H refers to bases A, U, or C. Y refers to pyrimidine bases. "" refers to a covalent bond.

FIG. 4 is a representation of the general structure of the hepatitis delta virus ribozyme domain known in the art. In each instance, each N and N' independently is any normal or modified base and each dash represents a potential base-pairing interaction. These nucleotides may be modified at the sugar, base or phosphate.

FIG. 5 is a representation of the general structure of the self-cleaving VS RNA ribozyme domain.

FIG. 6 is a schematic representation of a combinatorial approach to the screening of ribozyme variants.

Figure 1:
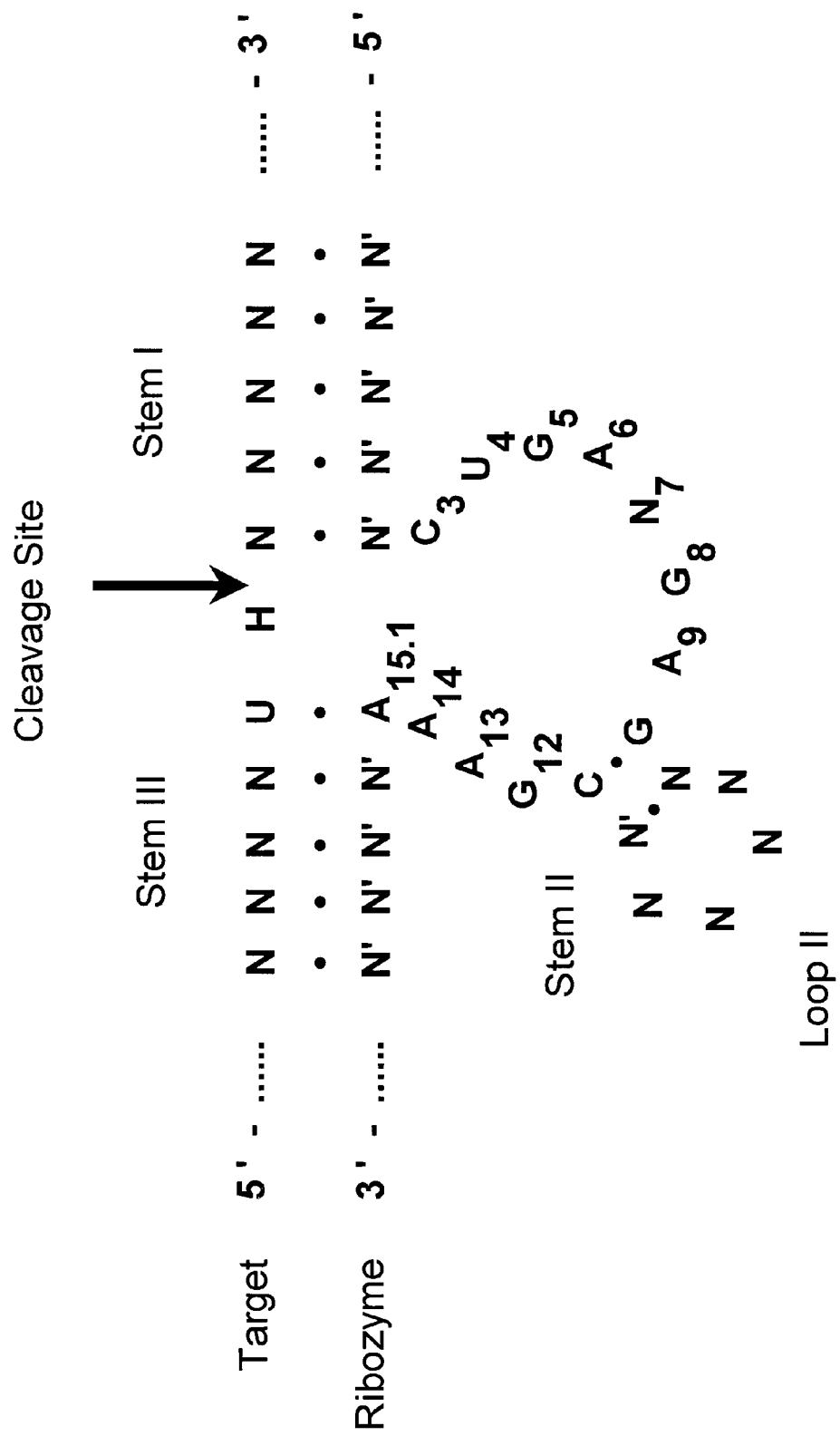
Figure 2:
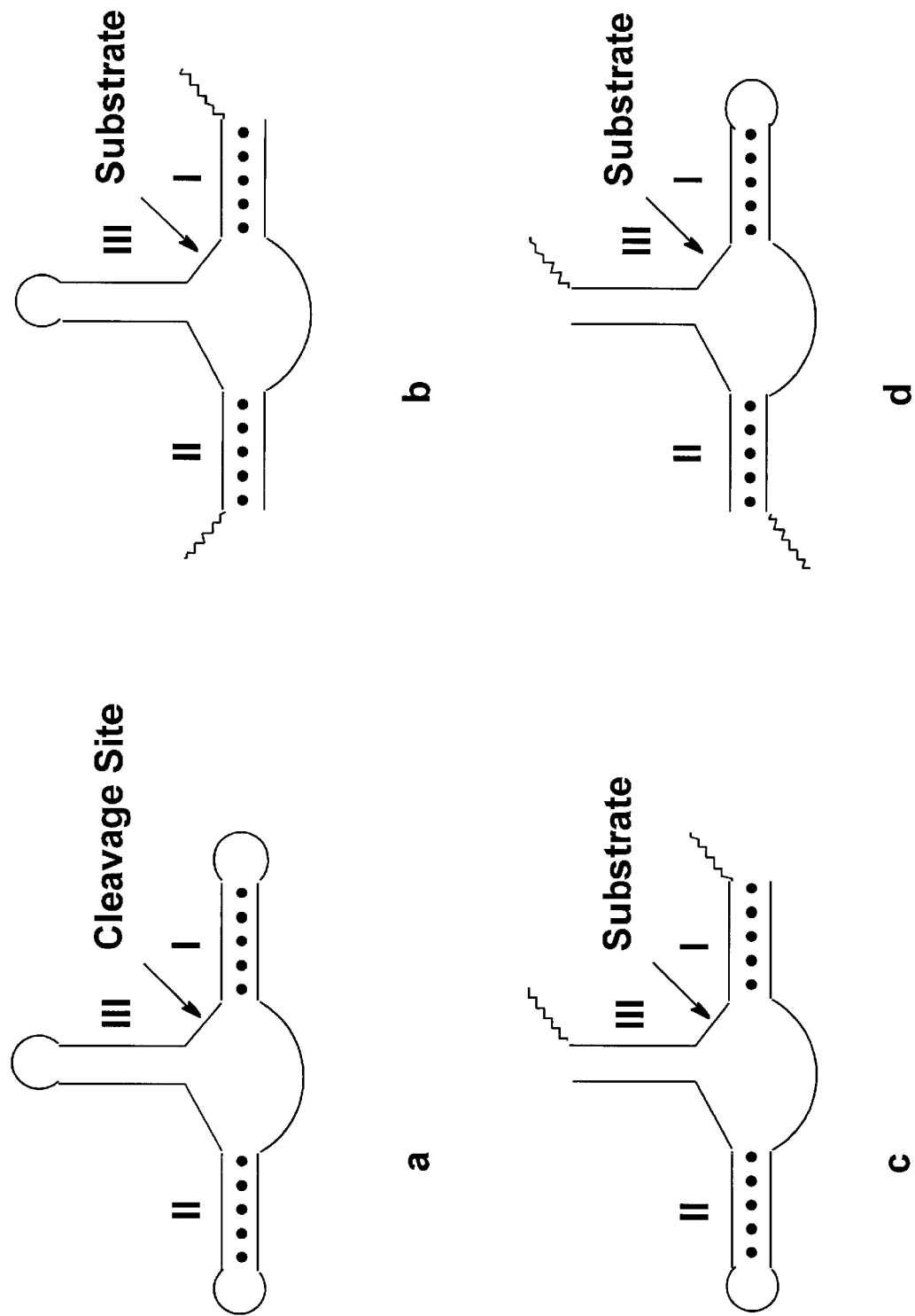
Figure 3:
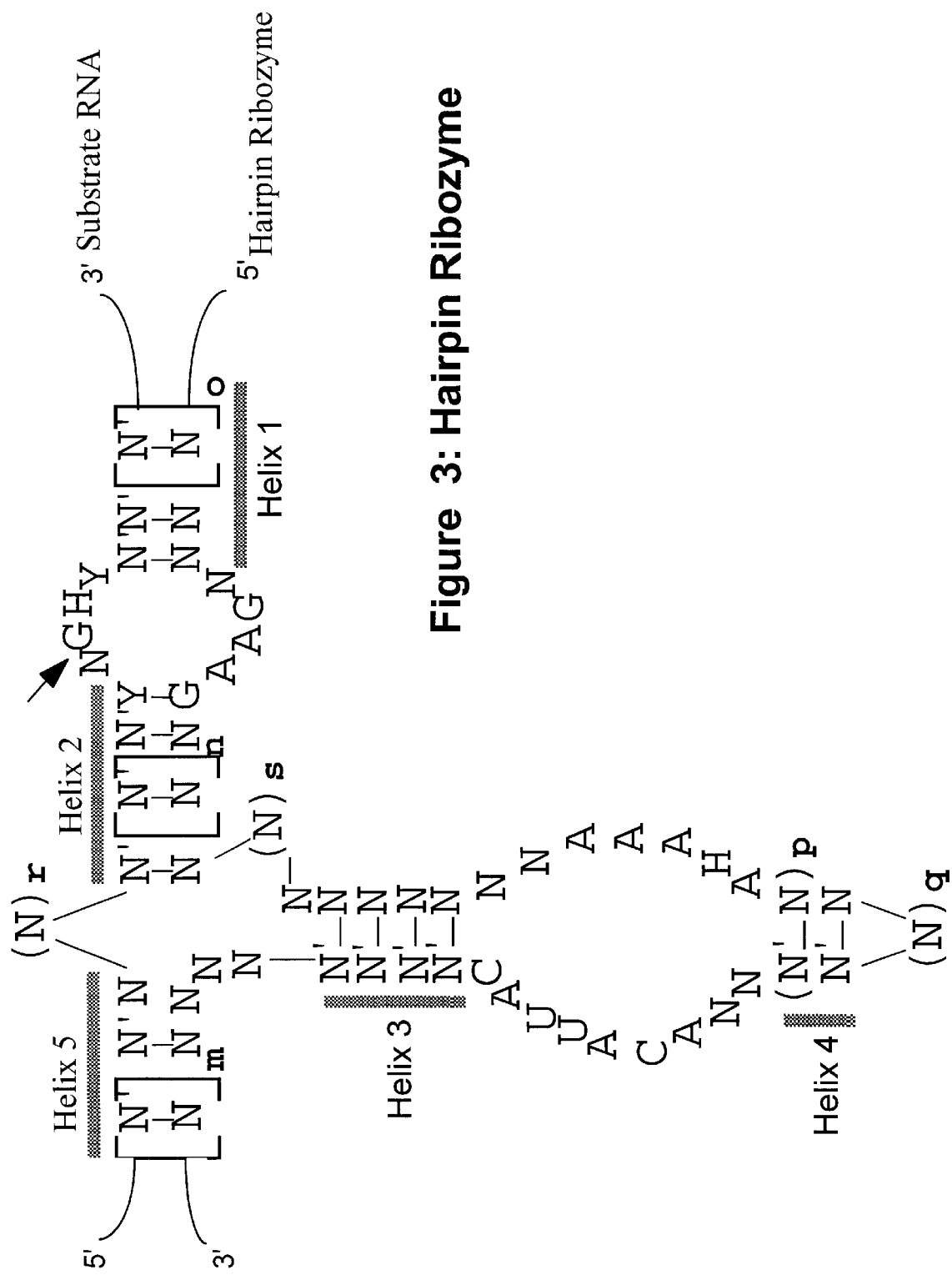
Figure 4:
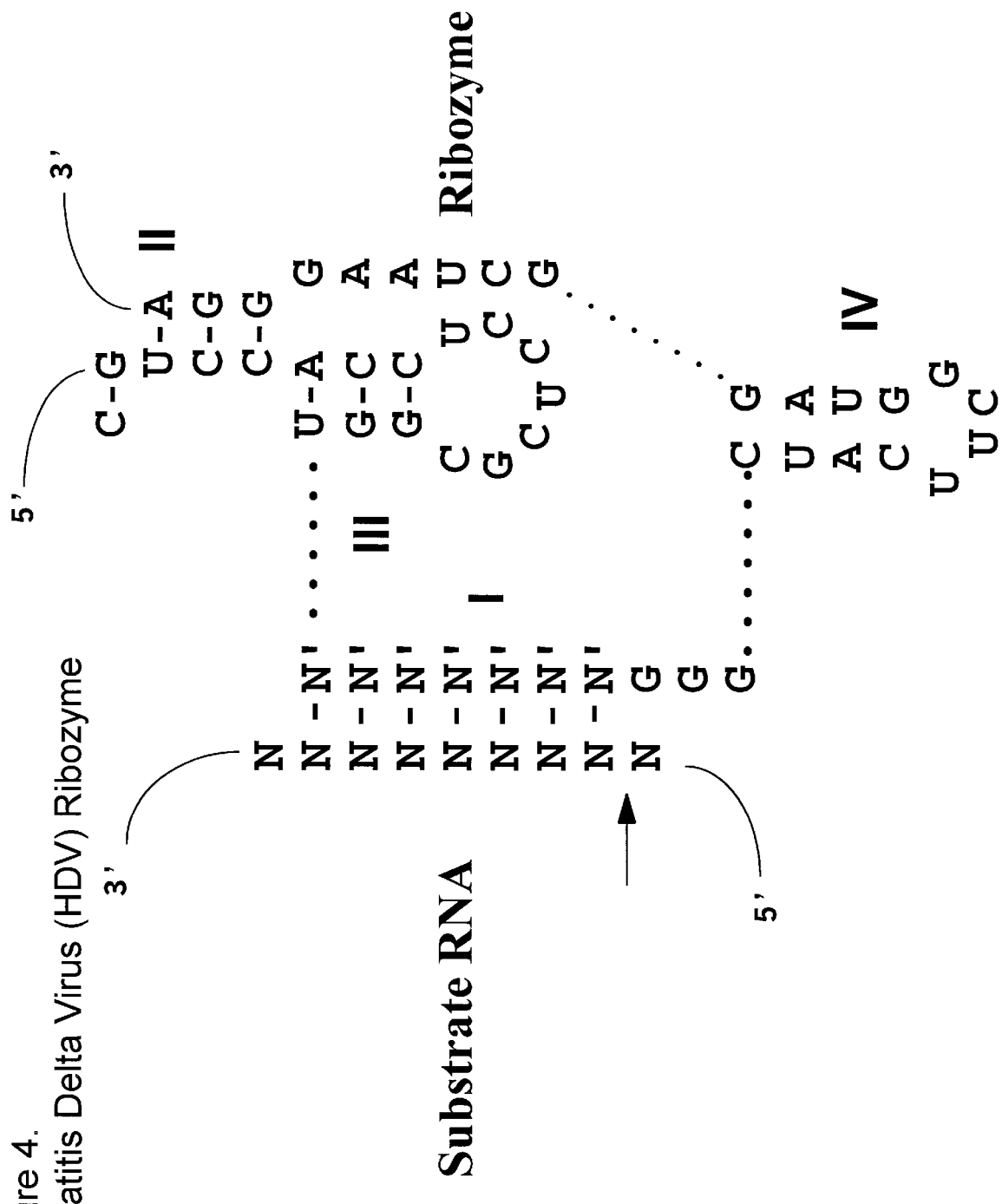

FIG. 7 shows the sequence of a Starting Ribozyme to be used in the screening approach described in FIG. 6. The Starting Ribozyme is a hammerhead (HH) ribozyme designed to cleave target RNA A (HH-A). Position 7 in HH-A is also referred to in this application as position 24 to indicate that U24 is the 24th nucleotide incorporated into the HH-A ribozyme during chemical synthesis. Similarly, positions 4 and 3 are also referred to as positions 27 and 28, respectively. s indicates phosphorothioate substitution. Lower case alphabets in the HH-A sequence indicate 2'-O-methyl nucleotides; uppercase alphabets in the sequence of HH-A at positions 5, 6, 8, 12 and 15.1 indicate ribonucleotides. Positions 3, 4 and 7 are shown as uppercase, large alphabets to indicate the positions selected for screening using the method shown in FIG. 6. ● indicates base-paired interaction. iB represents abasic inverted deoxy ribose moiety.

FIG. 8 shows a scheme for screening variants of HH-A ribozyme. Positions 24, 27 and 28 are selected for analysis in this scheme.

FIG. 9 shows non-limiting examples of some of the nucleotide analogs that can be used to construct ribozyme libraries. 2'-O-MTM-U represents 2'-O-methylthiomethyl uridine; 2'-O-MTM-C represents 2'-O-methylthiomethyl cytidine; 6-Me-U represents 6-methyl uridine (Beigelman et al., International PCT Publication No. WO 96/18736 which is incorporated by reference herein).

FIG. 10A–D show activity of HH-A variant ribozymes as determined in a cell-based assay. * indicates the substitution that provided the most desirable attribute in a ribozyme.

FIG. 11A shows the sequence and chemical composition of ribozymes that showed the most desirable attribute in a cell.

FIG. 11B–C show formulae for four different novel ribozyme motifs.

FIG. 12 shows the formula foe a novel ribozyme motif.

FIG. 13 shows the sequence of a Starting Ribozyme to be used in the screening approach described in FIG. 14. A HH ribozyme targeted against RNA B (HH-B) was chosen for analysis of the loop II sequence variants.

FIG. 14 shows a scheme for screening loop-II sequence variants of HH-B ribozyme.

FIG. 15 shows the relative catalytic rates ($k_{rel}$) for RNA cleavage reactions catalyzed by HH-B loop-II variant ribozymes.

FIG. 16 is a schematic representation of HH-B ribozyme-substrate complex and the activity of HH-B ribozyme with either the 5'-GAAA-3' or the 5'-GUUA-3' loop-II sequence.

FIG. 17 shows a scheme for using a combinatorial approach to identify potential ribozyme targets by varying the binding arms.

FIG. 18 shows a scheme for using a combinatorial approach to identify novel ribozymes by the varying putative catalytic domain sequence.

In one preferred embodiment, the method relies upon testing mixtures (libraries) of ribozymes with various nucleotides, nucleotide analogs, or other analog substitutions, rather than individual ribozymes, to rapidly identify the nucleotide, nucleotide analog, or other analog that is variable at one or more positions within a ribozyme. In the first step (step 1, FIG. 6), a desired number of positions (for example, 3 positions as shown in FIG. 6) are chosen for variation in a first ribozyme motif (Starting Ribozyme); there is no requirement on the number of positions that can be varied and these positions may or may not be phylogenetically conserved for the ribozyme. In addition, these position may reside within the catalytic core, binding arms, or accessory domains. The number of positions that are chosen to be varied defines the number of "Classes" of ribozyme libraries that will be synthesized. In the example illustrated in, FIG. 6, three positions (designated positions 1, 2 and 3) are varied, so three different Classes of ribozyme pool are synthesized. In the next step (step 2), ribozyme pools are synthesized containing a random mixture of different nucleotides, nucleotide analogs, or other analogs at all of the desired positions (designated "X") to be varied except one, which is the "fixed" position (designated "F"). The fixed position contains a specific nucleotide, nucleotide analog or other analog. There is no requirement for the number of nucleotides, or analogs be used. The number of nucleotides or analogs defines the number of pools (designated n) in each Class. For example if ten different nucleotides or analogs are chosen, ten different pools (n=10) will be synthesized for each Class; each of the pools will contain a specific modification at one fixed position (designated F) but will contain an equal mixture of all ten modifications at the other positions (designated X). In a subsequent step (step 3), the different pools of ribozymes are tested for desired activity, phenotype, characteristic or attribute. For example, the testing may be determining in vitro rates of target nucleic acid cleavage for each pool, testing ribozyme-substrate binding affinities, testing nuclease resistance, determining pharmacodynamic properties, or determining which pool is most efficacious in a cellular or animal model system. Following testing, a particular pool is identified as a desired variant (designated "Desired Variant-1") and the nucleotide or the analog present at the fixed position within the Desired Variant-1 is made constant (designated "Z") for all subsequent experiments; a single position within a ribozyme is therefore varied, i.e., the variable nucleotide or analog at a single position, when all other X positions are random, is identified within a ribozyme motif. Subsequently, new ribozyme pools (Classes 2, 3 etc.) are synthesized containing an equal mixture of all nucleotides or analogs at the remaining positions to be optimized except one fixed position and one or more constant positions. Again, a specific nucleotide or analog is "fixed" at a single position that is not randomized and the pools are assayed for a particular phenotype or attribute (step 4). This process is repeated until all desired positions have been varied and screened. For example if three positions are chosen for optimization, the synthesis and testing will need to be repeated three times (3 Classes). In the first two Classes, pools will be synthesized; in the final Class, specific ribozymes will be synthesized and tested. When the final position is analyzed (step 5), no random positions will remain and therefore only individual ribozymes are synthesized and tested. The resulting ribozyme or ribozymes (designated "second ribozyme motif") will have a defined chemical composition which will likely be distinct from the Starting Ribozyme motif (first ribozyme motif). This is a rapid method of screening for variability of one or more positions within a ribozyme motif.

In another preferred embodiment, the invention involves screening of chemical modifications at one or more positions within a hammerhead ribozyme motif. More specifically, the invention involves variability in the catalytic core sequence of a hammerhead ribozyme. Particularly, the invention describes screening for variability of positions 3, 4 and 7 within a hammerhead ribozyme. The invention also features screening for optimal loop II sequence in a hammerhead ribozyme.

In yet another preferred embodiment, the invention features a rapid method for screening accessible ribozyme cleavage sites within a target sequence. This method involves screening of all possible sequences in the binding arm of a ribozyme. The sequence of the binding arms determines the site of action of certain ribozymes. The combinatorial approach can be used to identify desirable and/or accessible sites within a target sequence by essentially testing all possible arm sequences. The difficulty with this approach is that ribozymes require a certain number of base pairs (for example, for hammerhead ribozymes the binding arm length is approximately 12–16 nucleotides) in order to bind functionally and sequence-specifically. This would require, for example 12–16 different groups of hammerhead ribozyme pools; 12–16 positions would have to be optimized which would require 12–16 different groups being synthesized and tested. Each pool would contain the four different nucleotides (A, C, U and G) or nucleotide analogs (p=4 for nucleotides). It would be very time consuming to test each group, identify the best pool, synthesize another group of ribozyme pools with one additional position constant, and then repeat the procedure until all 12–16 groups had been tested. However it is possible to decrease the number of Classes by testing multiple positions within a single Class. In this case, the number of pools within a Class equals the number of nucleotides or analogs in the random mixture (i.e. n) to the w power, where w equals the number of positions fixed in each Class. The number of Classes that need to be synthesized to optimize the final ribozyme equals the total number of positions to be optimized divided by the number of positions (w) tested within each Class. The number of pools in each Class=$n^w$. The number of Class= total number of positions /w.

In another preferred embodiment, the invention features a rapid method of screening for new catalytic nucleic acid motifs by keeping the binding arms constant and varying one or more positions in a putative catalytic domain. Applicant describes a method to vary positions within the catalytic domain, without changing positions within the binding arms, in order to identify new catalytic motifs. An example is illustrated in FIG. 18. It is unclear how many positions are required to obtain a functional catalytic domain in a nucleic acid molecule, however it is reasonable to presume that if a large number of functionally diverse nucleotide analogs can be used to construct the pools, a relatively small number of positions could constitute a functional catalytic domain. This may especially be true if analogs are chosen that one would expect to participate in catalysis (e.g. acid/base catalysts, metal binding, etc.). In the example illustrated, four positions (designated 1, 2, 3 and 4) are chosen. In the first step, ribozyme libraries (Class 1) are constructed: position 1 is fixed ($F_1$) and positions 2, 3 and 4 are random ($X_2$, $X_3$ and $X_4$, respectively). In step 2, the pools (the number of pools tested depends on the number of analogs used; n) are assayed for activity. This testing may be performed in vitro or in a cellular or animal model. Whatever assay that is used, the pool with the desired characteristic is identified and libraries (class 2) are again synthesized with position 1 now constant ($Z_1$) with the analog that was identified in class 1. In class 2, position 2 is fixed ($F_2$) and positions 3 and 4 are random ($X_3$ and $X_4$). This process is repeated until every position has been made constant and the chemical composition of the catalytic domain is determined. If the number of positions in the catalytic domain to be varied are large, then it is possible to decrease the number of Classes by testing multiple positions within a single Class. the number of pools within a Class equals the number of nucleotides or analogs in the random mixture (ie. n) to the w power, where w equals the number of positions fixed in each Class. The number of Classes that need to be synthesized to optimize the final ribozyme equals the total number of positions to be optimized divided by the number of positions (w) tested within each Class. The number of pools in each Class=$n^w$. The number of Classes=total number of positions /w.

In a preferred embodiment a method for identifying variants of a nucleic acid catalyst is described comprising the steps of: a) selecting at least three (3) positions, preferably 3–12, specifically 4–10, within said nucleic acid catalyst to be varied with a predetermined group of different nucleotides, these nucleotides are modified or unmodified (non-limiting examples of nucleotides that can used in this method are shown in FIG. 9); b) synthesizing a first class of different pools of said nucleic acid catalyst, wherein the number of pools synthesized is equal to the number of nucleotides in the predetermined group of different nucleotides (for example if 10 different nucleotides are selected to be in the group of predetermined nucleotides then 10 different pools of nucleic acid catalysts have to be synthesized), wherein at least one of the positions to be varied in each pool comprises a defined nucleotide (fixed position; F) selected from the predetermined group of different nucleotides and the remaining positions to be varied comprise a random mixture of nucleotides (X positions) selected from the predetermined group of different nucleotides;

c) testing the different pools of said nucleic acid catalyst under conditions suitable for said pools to show a desired attribute (including but not limited to improved cleavage rate, cellular and animal efficacy, nuclease stability, enhanced delivery, desirable localization) and identifying the pool with said desired attribute and wherein the position with the defined nucleotide (F) in the pool with the desired attribute is made constant (Z position) in subsequent steps; d) synthesizing a second class of different pools of nucleic acid catalyst, wherein at least one of the positions to be varied in each of the second class of different pools comprises a defined nucleotide (F) selected from the predetermined group of different nucleotides and the remaining positions to be varied comprise a random mixture (X) of nucleotides selected from the predetermined group of different nucleotides (this second class of pools therefore has F, X and Z positions); e) testing the second class of different pools of said nucleic acid catalyst under conditions suitable for showing desired attribute and identifying the pool with said desired attribute and wherein the position with the defined nucleotide in the pool with the desired attribute is made constant (Z) in subsequent steps; and f) this process is repeated until every position selected in said nucleic acid catalyst to be varied is made constant In yet another preferred embodiment, a method for identifying novel nucleic acid molecules in a biological system is described, comprising the steps of: a) synthesizing a pool of nucleic acid catalyst with a substrate binding domain and a catalytic domain, wherein said substrate binding domain comprises a random sequence; b) testing the pools of nucleic acid catalyst under conditions suitable for showing a desired effect (such as inhibition of cell proliferation, inhibition of angiogenesis, modulation of growth and/or differentiation, and others) and identifying the catalyst with said desired attribute; c) using an oligonucleotide, comprising the sequence of the substrate binding domain of the nucleic acid catalyst showing said desired effect, as a probe, screening said biological system for nucleic acid molecules complementary to said probe; and d) isolating and sequencing said complementary nucleic acid molecules. These nucleic acid molecules identified using a nucleic acid screening method described above may be new gene sequences, or known gene sequences. The advantage of this method is that nucleic acid sequences, such as genes, involved in a biological process, such as differentiation, cell growth, disease processes including cancer, tumor angiogenesis, arthritis, cardiovascular disease, inflammation, restenosis, vascular disease and the like, can be readily identified.

In a preferred embodiment, the invention features a nucleic acid molecule with catalytic activity having one of the formulae I-V:

Formula I

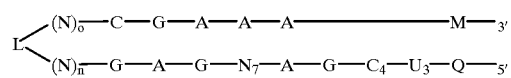

Formula II

Z3 = 2'- O—MTM—U
Z4 = 2'- C—Allyl—U
Z7 = 6- Methyl—U

Formula III

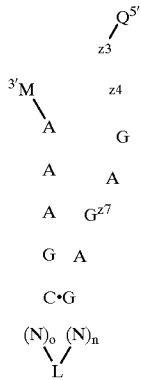

Z3 = 2'- O—MTM—U
Z4 = 2'- O—MTM—C
Z7 = 6- Methyl—U

Formula IV

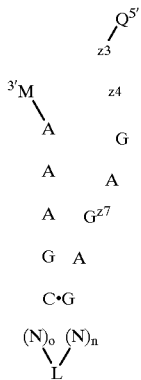

Z3 = 2'- O—MTM—U
Z4 = 2'- O—MTM—C
Z7 = 2'- C—Allyl—U

Formula V

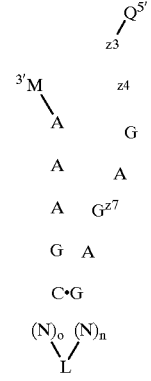

Z3 = 2'- O—MTM—U
Z4 = 2'- O—MTM—C
Z7 = Pyridin-4-One

In each of the above formulae, N represents independently a nucleotide in or a non-nucleotide linker, which may be same or different; M and Q are independently oligonucleotides of length sufficient to stably interact (e.g., by forming hydrogen bonds with complementary nucleotides in the target) with a target nucleic acid molecule (the target can be an RNA, DNA or RNA/DNA mixed polymers); preferably the length of Q is greater than or equal to 3 nucleotides and the length of M is preferably greater than or equal to 5 nucleotides; o and n are integers greater than or equal to 1 and preferably less than about 100, wherein if $(N)_o$ and $(N)_n$ are nucleotides, $(N)_o$ and $(N)_n$ are optionally able to interact by hydrogen bond interaction; L is a linker which may be present or absent (i.e., the molecule is assembled from two separate molecules), but when present, is a nucleotide and/or a non-nucleotide linker, which may be a single-stranded and/or double-stranded region; and represents a chemical linkage (e.g. a phosphate ester linkage, amide linkage or others known in the art). 2'-O-MTM-U and 2'-O-MTM-C refers to 2'-O-methylthiomethyl uridine and 2'-O-methylthiomethyl-cytidine, respectively. A, C, U and G represent adenosine, cytidine, uridine and guanosine nucleotides, respectively. The nucleotides in the formulae are unmodified or modified at the sugar, base, and/or phosphate portions as known in the art.

In yet another embodiment, the nucleotide linker (L) is a nucleic acid aptamer, such as an ATP aptamer, HIV Rev aptamer (RRE), HIV Tat aptamer (TAR) and others (for a review see Gold et al., 1995, *Annu. Rev. Biochem.*, 64, 763; and Szostak & Ellington, 1993, in The RNA World, ed. Gesteland and Atkins, pp 511, CSH Laboratory Press). A "nucleic acid aptamer" as used herein is meant to indicate nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, aminoacids, nucleic acid molecules, hormones, carbohydrates, receptors, cells, viruses, bacteria and others.

In yet another embodiment, the non-nucleotide linker (L) is as defined herein.

The term "nucleotide" is used as recognized in the art to include natural bases (standard), and modified bases well known in the art. Such bases are generally located at the 1' position of a sugar moiety. Nucleotide generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art and has recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry*, 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

In particular, the invention features modified ribozymes having a base substitution selected from pyridin-4-one, pyridin-2-one, phenyl, pseudouracil, 2, 4, 6-trimethoxy benzene, 3-methyluracil, dihydrouracil, naphthyl, 6-methyluracil and aminophenyl.

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modification of enzymatic nucleic acid molecules have been extensively described in the art (see Eckstein et al., International Publication PCT No. WO 92/07065; Perrault et al. *Nature* 1990, 344, 565–568; Pieken et al. *Science* 1991, 253, 314–317; Usman and Cedergren, Trends in *Biochem. Sci.* 1992, 17, 334–339; Usman et al. International Publication PCT No. WO 93/15187; Sproat, U.S. Pat. No. 5,334,711 and Beigelman et al., 1995 *J. Biol. Chem.* 270, 25702).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

In yet another embodiment, the non-nucleotide linker (L) is as defined herein. The term "non-nucleotide" as used herein include either abasic nucleotide, polyether, polyamine, polyamide, peptide, carbohydrate, lipid, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., Nucleosides & Nucleotides 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. Thus, in a preferred embodiment, the invention features an enzymatic nucleic acid molecule having one or more non-nucleotide moieties, and having enzymatic activity to cleave an RNA or DNA molecule. By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. The terms "abasic" or "abasic nucleotide" as used herein encompass sugar moieties lacking a base or having other chemical groups in place of base at the 1' position.

In preferred embodiments, the enzymatic nucleic acid includes one or more stretches of RNA, which provide the enzymatic activity of the molecule, linked to the non-nucleotide moiety. The necessary RNA components are known in the art, see, e.g., Usman, supra. By RNA is meant a molecule comprising at least one ribonucleotide residue.

As the term is used in this application, non-nucleotide-containing enzymatic nucleic acid means a nucleic acid molecule that contains at least one non-nucleotide component which replaces a portion of a ribozyme, e.g., but not limited to, a double-stranded stem, a single-stranded "catalytic core" sequence, a single-stranded loop or a single-stranded recognition sequence. These molecules are able to cleave (preferably, repeatedly cleave) separate RNA or DNA molecules in a nucleotide base sequence specific manner. Such molecules can also act to cleave intramolecularly if that is desired. Such enzymatic molecules can be targeted to virtually any RNA transcript.

By the phrase "nucleic acid catalyst" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region (e.g. M and Q in formulae I-V) to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity.

By "nucleic acid molecule" as used herein is meant a molecule comprising nucleotides. The nucleic acid can be composed of modified or unmodified nucleotides or non-nucleotides or various mixtures and combinations thereof.

By "complementarity" is meant a nucleic acid that can form hydrogen bond(s) with other RNA sequence by either traditional Watson-Crick or other non-traditional types (for example, Hoogsteen type) of base-paired interactions.

By "oligonucleotide" as used herein, is meant a molecule comprising two or more nucleotides.

The specific enzymatic nucleic acid molecules described in the instant application are not limiting in the invention and those skilled in the art will recognize that all that is important in an enzymatic nucleic acid molecule of this invention is that it has a specific substrate binding site (e.g., M and/or Q of Formulae 1-V above) which is complementary to one or more of the target nucleic acid regions, and that it have nucleotide sequences within or surrounding that substrate binding site which impart a nucleic acid cleaving activity to the molecule.

The invention provides a method for producing a class of enzymatic cleaving agents which exhibit a high degree of specificity for the nucleic acid sequence of a desired target. The enzymatic nucleic acid molecule is preferably targeted to a highly conserved sequence region of a target such that specific diagnosis and/or treatment of a disease or condition can be provided with a single enzymatic nucleic acid. Such enzymatic nucleic acid molecules can be delivered exogenously to specific cells as required. In the preferred hammerhead motif the small size (less than 60 nucleotides, preferably between 30–40 nucleotides in length) of the molecule allows the cost of treatment to be reduced.

Therapeutic ribozymes must remain stable within cells until translation of the target RNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes to enhance their nuclease stability.

By "enzymatic portion" is meant that part of the ribozyme essential for cleavage of an RNA substrate.

By "substrate binding arm" is meant that portion of a ribozyme which is complementary. to (i.e., able to base-pair with) a portion of its substrate. Generally, such complementarity is 100%, but can be less if desired. For example, as few as 10 bases out of 14 may be base-paired. Such arms are shown generally in FIG. 1A and as M and/or Q in Formulae I-V. That is, these arms contain sequences within a ribozyme which are intended to bring ribozyme and target RNA together through complementary base-pairing interactions.

In a preferred embodiment, the invention provides a method for producing a class of enzymatic cleaving agents which exhibit a high degree of specificity for the nucleic acid of a desired target. Such enzymatic nucleic acid molecules can be delivered exogenously to specific cells as required. Alternatively, the ribozymes can be expressed from DNA/RNA vectors that are delivered to specific cells.

The enzymatic nucleic acid molecules of the instant invention can also be expressed within cells from eukaryotic promoters (e.g., Izant and Weintraub, 1985 *Science* 229, 345; McGarry and Lindquist, 1986 *Proc. Natl. Acad. Sci. USA* 83, 399; Scanlon et al., 1991, *Proc. Natl. Acad. Sci. USA,* 88, 10591–5; Kashani-Sabet et al., 1992 *Antisense Res. Dev.,* 2, 3–15; Dropulic et al., 1992 *J. Virol,* 66, 1432–41; Weerasinghe et al., 1991 *J. Virol,* 65, 5531–4; Ojwang et al., 1992 *Proc. Natl. Acad. Sci. USA* 89, 10802–6; Chem et al., 1992 *Nucleic Acids Res.,* 20, 4581–9; Sarver et al., 1990 *Science* 247, 1222–1225; Thompson at al., 1995 *Nucleic Acids Res.* 23, 2259). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO 93/23569, and Sullivan et al., PCT WO94/02595; Ohkawa et al., 1992 *Nucleic Acids Symp. Ser.,* 27, 15–6; Taira et al., 1991, *Nucleic Acids Res.,* 19, 5125–30; Ventura et al., 1993 *Nucleic Acids Res.,* 21, 3249–55; Chowrira et al., 1994 *J. Biol. Chem.* 269, 25856; hereby incorporated in their totality by reference herein).

By "consists essentially of" is meant that the active ribozyme contains an enzymatic center or core equivalent to those in the examples, and binding arms able to bind target nucleic acid molecules such that cleavage at the target site occurs. Other sequences may be present which do not interfere with such cleavage.

Thus, in one aspect, the invention features ribozymes that inhibit gene expression and/or cell proliferation. These chemically or enzymatically synthesized nucleic acid molecules contain substrate binding domains that bind to accessible regions of specific target nucleic acid molecules. The nucleic acid molecules also contain domains that catalyze the cleavage of target. Upon binding, the enzymatic nucleic acid molecules cleave the target molecules, preventing for example, translation and protein accumulation. In the absence of the expression of the target gene, cell proliferation, for example, is inhibited.

In a preferred embodiment, the enzymatic nucleic acid molecules are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. Using the methods described herein, other enzymatic nucleic acid molecules that cleave target nucleic acid may be derived and used as described above. Specific examples of nucleic acid catalysts of the instant invention are provided below in the Tables and figures.

Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., supra which have been incorporated by reference herein.

In another aspect of the invention, enzymatic nucleic acid molecules that cleave target molecules are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review see Couture and Stinchcomb, 1996, TIG., 12, 510).

In a preferred embodiment, an expression vector comprising nucleic acid sequence encoding at least one of the nucleic acid catalyst of the instant invention is disclosed. The nucleic acid sequence encoding the nucleic acid catalyst of the instant invention is operable linked in a manner which allows expression of that nucleic acid molecule.

In one embodiment, the expression vector comprises: a transcription initiation region (e.g., eukaryotic pol I, II or III initiation region); b) a transcription termination region (e.g., eukaryotic pol I, II or III termination region); c) a gene encoding at least one of the nucleic acid catalyst of the instant invention; and wherein said gene is operably linked to said initiation region and said termination region, in a manner which allows expression and/or delivery of said nucleic acid molecule. The vector may optionally include an open reading frame (ORF) for a protein operably linked on the 5' side or the 3'-side of the gene encoding the nucleic acid catalyst of the invention; and/or an intron (intervening sequences).

By "patient" is meant an organism which is a donor or recipient of explanted cells or the cells themselves. "Patient" also refers to an organism to which enzymatic nucleic add molecules can be administered. Preferably, a patient is a mammal or mammalian cells. More preferably, a patient is a human or human cells.

By "vectors" is meant any nucleic acid- and/or viral-based technique used to deliver a desired nucleic acid.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA,* 87, 6743–7; Gao and Huang 1993 *Nucleic Acids Res.,* 21, 2867–72; Lieber et al., 1993 *Methods Enzymol.,* 217, 47–66; Zhou et al., 1990 *Mol. Cell. Biol.,* 10, 4529–37). Several investigators have demonstrated that ribozymes expressed from such promoters can function in mammalian cells (e.g. Kashani-Sabet et al., 1992 *Antisense Res. Dev.,* 2, 3–15; Ojwang et al., 1992 *Proc. Natl. Acad. Sci. USA,* 89, 10802–6; Chen et al., 1992 *Nucleic Acids Res.,* 20, 4581–9; Yu et al., 1993 *Proc. Natl. Acad. Sci. USA,* 90, 6340–4; L'Huillier et al., 1992 *EMBO J.* 11, 4411–8; Lisziewicz et al., 1993 *Proc. Natl. Acad. Sci. U.S.A.,* 90, 8000–4; Thompson et al., 1995 *Nucleic Acids Res.* 23, 2259; Sullenger & Cech, 1993, *Science,* 262, 1566). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In a preferred embodiment an expression vector comprising nucleic acid sequence encoding at least one of the catalytic nucleic acid molecule of the invention, in a manner which allows expression of that nucleic acid molecule.

The expression vector comprises in one embodiment; a) a transcription initiation region; b) a transcription termination region; c) a gene encoding at least one said nucleic acid molecule; and wherein said gene is operably linked to said initiation region and said termination region, in a manner which allows expression and/or delivery of said nucleic acid molecule. In another preferred embodiment the expression vector comprises: a) a transcription initiation region; b) a transcription termination region; c) an open reading frame; d) a gene encoding at least one said nucleic acid molecule, wherein said gene is operably linked to the 3'-end of said open reading frame; and wherein said gene is operably linked to said initiation region, said open reading frame and said termination region, in a manner which allows expression and/or delivery of said nucleic acid molecule. In yet another embodiment the expression vector comprises: a) a transcription initiation region; b) a transcription termination region; c) an intron; d) a gene encoding at least one said nucleic acid molecule; and wherein said gene is operably linked to said initiation region, said intron and said termination region, in a manner which allows expression and/or delivery of said nucleic acid molecule. In other embodiment, the expression vector comprises: a) a transcription initiation region; b) a transcription termination region; c) an intron; d) an open reading frame; e) a gene encoding at least one said nucleic acid molecule, wherein said gene is operably linked to the 3'-end of said open reading frame; and wherein said gene is operably linked to said initiation region, said intron, said open reading frame and said termination region, in a manner which allows expression and/or delivery of said nucleic acid molecule.

In a preferred embodiment, the invention features a method of synthesis of enzymatic nucleic acid molecules of instant invention which follows the procedure for normal chemical synthesis of RNA as described in Usman et al., 1987 *J. Am. Chem. Soc.,* 109, 7845; Scaringe et al., 1990 *Nucleic Acids Res.,* 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 $\mu$mol scale protocol with a 5 min coupling step for alkylsilyl protected nucleotides and 2.5 min coupling step for 2'-O-methylated nucleotides. Table II outlines the amounts, and the contact times, of the reagents used in the synthesis cycle. A 6.5-fold excess (163 $\mu$L of 0.1 M=16.3 $\mu$mol) of phosphoramidite and a 24-fold excess of S-ethyl tetrazole (238 $\mu$L of 0.25 M=59.5 $\mu$mol) relative to polymer-bound 5'-hydroxyl is used in each coupling cycle. Average coupling yields on the 394 Applied Biosystems, Inc. synthesizer, determined by colorimetric quantitation of the trityl fractions, is 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6- lutidine in THF (ABI); oxidation solution was 16.9 mM $I_2$, 49 mM pyridine, 9% water in THF (Millipore). B & J Synthesis Grade acetonitrile is used directly from the reagent bottle. S-Ethyl tetrazole solution (0.25 M in acetonitrile) is made up from the solid obtained from American International Chemical, Inc.

In a preferred embodiment, deprotection of the chemically synthesized nucleic acid catalysts of the invention is performed as follows. The polymer-bound oligoribonucleotide, trityl-off, is transferred from the synthesis column to a 4 mL glass screw top vial and suspended in a solution of methylamine (MA) at 65° C. for 10 min. After cooling to −20° C., the supernatant is removed from the polymer support. The support is washed three times with 1.0 mL of EtOH:MeCN:$H_2O$/3:1:1, vortexed and the supernatant is then added to the first supernatant. The combined supernatants, containing the oligoribonucleotide, are dried to a white powder.

The base-deprotected oligoribonucleotide is resuspended in anhydrous TEA·HF/NMP solution (250 μL of a solution of 1.5 mL N-methylpyrrolidinone, 750 μL TEA and 1.0 mL TEA·3HF to provide a 1.4M HF concentration) and heated to 65° C. for 1.5 h. The resulting, fully deprotected, oligomer is quenched with 50 mM TEAB (9 mL) prior to anion exchange desalting.

For anion exchange desalting of the deprotected oligomer, the TEAB solution is loaded on to a Qiagen 500® anion exchange cartridge (Qiagen Inc.) that is pre-washed with 50 mM TEAB (10 mL). After washing the loaded cartridge with 50 mM TEAB (10 mL), the RNA is eluted with 2 M TEAB (10 mL) and dried down to a white powder. The average stepwise coupling yields are generally >98% (Wincott et al., 1995 *Nucleic Acids Res.* 23, 2677–2684).

Ribozymes of the instant invention are also synthesized from DNA templates using bacteriophage 17 RNA polymerase (Milligan and Uhlenbeck, 1989, *Methods Enzymol.* 180, 51).

Ribozymes are purified by gel electrophoresis using general methods or are purified by high pressure liquid chromatography (HPLC; See Wincott et al., supra) the totality of which is hereby incorporated herein by reference) and are resuspended in water.

In another preferred embodiment, catalytic activity of the molecules described in the instant invention can be optimized as described by Draper et al., supra. The details will not be repeated here, but include altering the length of the ribozyme binding arms, or chemically synthesizing ribozymes with modifications (base, sugar andfor phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162; Sproat, U.S. Pat. No. 5,334, 711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. (All these publications are hereby incorporated by reference herein.).

By "enhanced enzymatic activity" is meant to include activity measured in cells and/or in vivo where the activity is a reflection of both catalytic activity and ribozyme stability. In this invention, the product of these properties is increased or not significantly (less that 10 fold) decreased in vivo compared to an all RNA ribozyme.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10 fold (Burgin et al., 1996, *Biochemistry*, 35, 14090). Such ribozymes herein are said to "maintain" the enzymatic activity on all RNA ribozyme.

In a most preferred embodiment the invention features a method of synthesizing ribozyme libraries of various sizes. This invention describes methods to chemically synthesize ribozyme libraries of various sizes from suitable nucleoside analogs.

Considerations for the selection of nucleotide building blocks and determination of coupling efficiency: In addition to structural considerations (hydrogen bond donors and acceptors, stacking properties, pucker orientation of sugars, hydrophobicity or hydrophilicity of some subgroups constitutive of the nucleotides) that may lead to the selection of a specific nucleotide to be included in the design of a ribozyme library, one of the important features that needs to be considered when selecting nucleotide building blocks is the chemical compatibility of such building blocks with ribozyme synthesis. A "nucleotide building block" is a nucleoside or nucleoside analog that possess a suitably protected phosphorus atom at the oxidation state V reacting readily, upon activation, to give a $P^V$-containing internucleoside linkage. A suitable nucleoside building block may also contain a phosphorus atom at the oxidation state III reacting readily, upon activation, to give a $P^{III}$-containing internucleoside linkage that can be oxidized to the desired $P^V$-containing internucleoside linkage. Applicant has found that the phosphoramidite chemistry ($P^{III}$) is a preferred coupling method for ribozyme library synthesis. There are several other considerations while designing and synthesizing certain ribozyme libraries, such as: a) the coupling efficiencies of the nucleotide building blocks considered for a ribozyme library should not fall below 90% to provide a majority of full-length ribozyme; b) the nucleotide building blocks should be chemically stable to the selected synthesis and deprotection conditions of the particular ribozyme library; c) the deprotection schemes for the nucleotide building blocks incorporated into a ribozyme library, should be relatively similar and be fully compatible with ribozyme deprotection protocols. In particular, nucleoside building blocks requiring extended deprotection or that cannot sustain harsh treatment should be avoided in the synthesis of a ribozyme library. Typically, the reactivity of the nucleotide building blocks should be optimum when diluted to 100 mM to 200 mM in non-protic and relatively polar solvent. Also the deprotection condition using 3:1 mixture of ethanol and concentrated aqueous ammonia at 65 degrees C. for 4 hours followed by a fluoride treatment as exemplified In Wincott at al. supra, is particularly useful for ribozyme synthesis and is a preferred deprotection pathway for such nucleotide building blocks.

In one preferred embodiment, a "nucleotide building block mixing" approach to generate ribozyme libraries is described. This method involves mixing various nucleotide building blocks together in proportions necessary to ensure equal representation of each of the nucleotide building blocks in the mixture. This mixture is incorporated into the ribozyme at position(s) selected for randomization.

The nucleotide building blocks selected for incorporation into a ribozyme library, are typically mixed together in appropriate concentrations, in reagents, such as anhydrous acetonitrile, to form a mixture with a desired phosphoramidite concentration. This approach for combinatorial synthesis of a ribozyme library with one or more random positions within the ribozyme (X as described above) is particularly useful since a standard DNA synthesizer can handle a building block mixture similar to a building block solution containing a single building block. Such a nucleotide building block mixture is coupled to a solid support or to a growing ribozyme sequence attached to a solid-support. To ensure that the ribozyme library synthesized achieves the desired complexity, the scale of the synthesis is increased substantially above that of the total complexity of the library. For example, a 2.5 μmole ribozyme synthesis provides ~3×10$^{17}$ ribozyme molecules corresponding to sub-nanomolar amounts of each member of a billion compounds ribozyme library.

Divinylbenzene highly cross-linked polystyrene solid-support constitutes the preferred stationary phase for ribozyme library synthesis. However, other solid-support systems utilized in DNA or RNA synthesis can also be used for ribozyme library synthesis. This includes silica-based solid-supports such as controlled-pore glass (CPG) or polymeric solid-supports such as all types of derivatized polystyrene resins, grafted polymers of chloromethylated polystyrene crosslinked with ethylene glycol, oligoethylene glycol.

Because of different coupling kinetics of the nucleotide building blocks present in a mixture, it is necessary to evaluate the relative incorporation of each of the members of the mixture and to adjust, if needed, the relative concentration of the building blocks in the mixture to get equimolar representation, compensating thereby the kinetic parameter. Typically a building block that presents a slow coupling kinetic will be over-represented in the mixture and vice versa for a building block that presents a fast coupling kinetic. When equimolar incorporation is sought, acceptable limits for unequal incorporation may generally be +/−10%.

Synthesis of a random ribozyme library can be performed either with the mixture of desired nucleotide building blocks, or with a combination of certain random positions (obtained by using one or more building block mixtures) and one or more fixed positions that can be introduced through the incorporation of a single nucleotide building block reagent. For instance, in the oligonucleotide model 5'-TT XXXX TTB-3' used in example 2 infra, the positions from 3'-end 1 is fixed as 2'-deoxy-inverted abasic ribose (B), positions 2, 3, 8 and 9 have been fixed as 2'-deoxy-thymidine (T) while the X positions 4–7 correspond to an approximately equimolar distribution of all the nucleotide building blocks that make up the X mixture.

In another preferred embodiment, a "mix and split" approach to generate ribozyme libraries is described. This method is particularly useful when the number of selected nucleotide building blocks to be included in the library is large and diverse (greater than 5 nucleotide building blocks) and/or when the coupling kinetics of the selected nucleotide building blocks do not allow competitive coupling even after relative concentration adjustments and optimization. This method involves a multi-step process wherein the solid support used for ribozyme library synthesis is "split" (divided) into equal portions, (the number of portions is equal to the number of different nucleotide building blocks (n) chosen for incorporation at one or more random positions within the ribozyme). For example, if there are 10 different nucleotide building blocks chosen for incorporation at one or more positions in the ribozyme library, then the solid support is divided into 10 different portions. Each portion is independently coupled to one of the selected nucleotide building blocks followed by mixing of all the portions of solid support. The ribozyme synthesis is then resumed as before the division of the building blocks. This enables the synthesis of a ribozyme library wherein one or more positions within the ribozyme is random. The number of "splitting" and "mixing" steps is dependent on the number of positions that are random within the ribozyme. For example if three positions are desired to be random then three different splitting and mixing steps are necessary to synthesize the ribozyme library.

Random ribozyme libraries are synthesized using a non-competitive coupling procedure where each of the selected nucleotide analogs "n" separately couple to an inverse "n" (1/n) number of aliquots of solid-support or of a growing ribozyme chain on the solid-support. A very convenient way to verify completeness of the coupling reaction is the use of a standard spectrophotometric DMT assay (Oligonucleotide Synthesis, A Practical Approach, ed. M. Gait, pp 48, IRC Press, Oxford, UK; incorporated by reference herein). These aliquots may be subsequently combined, mixed and split into one new aliquot. A similar approach to making oligonucleotide libraries has recently been described by Cook et al., (U.S. Pat. No. 5,587,471) and is incorporated by reference herein.

EXAMPLES

The following are non-limiting examples showing the synthesis, screening and testing of catalytic nucleic acids of the instant invention.

The development of nucleic acid catalysts that are optimal for catalytic activity would contribute significantly to any strategy that employs nucleic acid cleaving ribozymes for the purpose of regulating gene expression. The hammerhead ribozyme functions with a catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) may be 10- to 100-fold slower. In contrast, the RNase P holoenzyme is believed to catalyze pre-tRNA cleavage with a $k_{cat}$ of ~30 min$^{-1}$ under optimal assay conditions. An artificial 'RNA ligase' ribozyme has been shown to catalyze the corresponding self-modification reaction with a rate of ~100 min$^{-1}$ (Ekland et al., 1995, *Science*, 269, 364). Finally, replacement of a specific residue within the catalytic core of the hammerhead with certain nucleotide analogues gives modified ribozymes that show as much as a 10-fold improvement in catalytic rate (Burgin et al., 1996, supra). These findings demonstrate that ribozymes can promote chemical transformations with catalytic rates that are significantly greater than those displayed in vitro by most natural self-cleaving ribozymes. It is then possible that the structures of certain ribozymes may not be optimized to give maximal catalytic activity, or that entirely new nucleic acid catalysts could be made that display significantly faster rates of catalysis.

An extensive array of site-directed mutagenesis studies have been conducted with ribozymes, such as the hammerhead ribozyme, to probe relationships between nucleotide sequence and catalytic activity. These systematic studies have made clear that most nucleotides in the conserved core of a ribozyme (Forster & Symons, 1987, *Cell*, 49,211; Ruffner et al., 1990, *Biochemistry* 29, 10695; Couture et al., 1990, *J. Mol. Bio.* 215, 345; Berzal-Herranz et al., 1993 supra; Perrota et al., 1996, *Nucleic Acid Res.* 24,1314) cannot be mutated without significant loss of catalytic activity. In contrast, a selection strategy that simultaneously surveys a large pool of mutagenized ribozymes for the ones that retain catalytic activity could be used more efficiently to define immutable sequences and to identify new ribozyme variants (Breaker, 1997, supra). For example, Joseph and Burke (1993; *J. Biol. Chem.,* 268, 24515) have used an in vitro selection approach to rapidly survey for sequence variants of the 'hairpin' self-cleaving RNA that show improved catalytic activity. This approach was successful in identifying two mutations in the hairpin ribozyme that together give a 10-fold improvement in catalytic rate. Although similar in vitro selection experiments have been conducted with the hammerhead ribozyme (Nakamaye & Eckstein, 1994, supra; Long & Uhlenbeck, 1994, supra; Ishizaka et al., 1995, supra), none of these efforts have successfully screened full-sized hammerhead ribozymes for all possible combinations of sequence variants that encompass the entire catalytic core.

Example 1
Optimizing Loop II Sequence of a Hammerhead Ribozyme (HH-B) for Enhanced Catalytic Rates To test the feasibility of the combinatorial approach described in FIG. 6 approach, Applicant chose to optimize the sequence of loop-II of a hammerhead ribozyme (HH-B) (see FIG. 13). Previous studies had demonstrated that a variety of chemical modifications and different sequences within loop-II may have significant effects on the rate of cleavage in vitro, despite the fact that this sequence is not phylogenetically conserved and can in fact be deleted completely. According to the standard numbering system for the hammerhead ribozyme, the four positions within loop II are numbered I2.1, I2.2, I2.3, and I2.4. The Starting Ribozyme (HH-B) contained the sequence $G_{I2.1} A_{I2.2} A_{I2.3} A_{I2.4}$. For simplicity, the four positions will be numbered 5' to 3': $G_{I2.1}=1$; $A_{I2.2}=2$; $A_{I2.3}=3$; $A_{I2.4}=4$. The remainder of the hammerhead ribozyme "template" remained constant and is based on a previously described hammerhead motif (Draper et al., International PCT Publication No. WO 95/13380, incorporated by reference herein).

A strategy for optimizing the four (number of Classes=4) loop-II positions is illustrated in FIG. 14. The four standard ribose nucleotides (A, C, U and G) were chosen to construct the ribozyme pools. (n=4). In the first step, four different pools were synthesized by the nucleotide building block mixing approach described herein. Applicant first chose to "fix" (designated F) position 3 because preliminary experiments indicated that the identity of the base at this position had the most profound effects on activity; positions 1, 2 and 4 are random. The four pools were assayed under stoichiometric conditions (1 µM ribozyme; 1 µM substrate), to help ensure that the entire population of ribozymes in each pool was assayed. Substrate and ribozyme were pre-annealed and the reactions were initiated with the addition of 10 mM $MgCl_2$. The rate of cleavage for each library was derived from plots of fraction of substrate cleaved as a function of time. Reactions were also performed simultaneously with the starting ribozyme (i.e. homogenous, loop-II=GAAA). The relative rate of cleavage for each library ($k_{rel}$) was calculated by dividing the observed rate of the library by the rate of the control/starting ribozyme and is plotted in FIG. 15. The error bars indicate the standard error derived from the curve fits. The results show that all four pools had similar rates ($k_{rel}$); however, the library possessing "U" at position 3 was slightly faster.

Ribozyme pools were again synthesized (Class 2) with position 3 being made constant ($U_3$), position 4 was fixed ($F_4$) and positions 1 and 2 were random (X). The four pools were assayed as before; the pool containing "A" at position 4 was identified as the most desirable pool. Therefore, during the synthesis of the next pool (Class 3), positions 3 and 4 were constant with $U_3$ and $A_4$, position 2 was fixed ($F_2$) and position 1 was random (X). The four pools were again assayed; all four pools showed very similar, but substantially elevated rates of cleavage. The pool containing U at position 2 was identified as the fastest. Therefore, during the synthesis of the final four ribozymes (Class 4), position 3, 4 and 2 were made constant with $U_3$, $A_4$ and $U_2$; position 1 was fixed with A, U, C or G. The final ribozyme containing G at position 4 was clearly identified as the fastest ribozyme, allowing—the identification of $G_{I2.1} U_{I2.2} U_{I2.3} A_{I2.4}$ as the optimized ribozyme motif.

To confirm that the final ribozyme ($G_{I2.1} U_{I2.2} U_{I2.3} A_{I2.4}$) was indeed faster that the starting ribozyme ($G_{I2.1} A_{I2.2} A_{I2.3} A_{I2.4}$) we compared the two ribozymes (illustrated in FIG. 16) under single-turnover conditions at saturating ribozyme concentrations. The observed rates should therefore measure the rate of the chemical step, $k_2$. The fraction of substrate remaining uncleaved as a function of time is shown in FIG. 16 (lower panel), and the derived rate contents are shown. The results show that the optimized ribozyme cleaves >10 times faster (3.7 $min^{-1}$ vs. 0.35 $min^{-1}$) than the starting ribozyme.

Example 2:
Optimizing Core Chemistly of a Hammerhead Ribozyme (HH-A)

To further test the feasibility of the approach described in FIG. 6, we chose to optimize the three pyrimidine residues within the core of a hammerhead ribozyme (HH-A). These three positions (shown in FIG. 7 as U7, U4 and C3) were chosen because previous studies indicated that these positions are critical for both stability (Beigelman et al., 1995, supra) and activity (Ruffner et al., 1990, supra; Burgin et al., 1996, supra) of the ribozyme. According to the standard numbering system for the hammerhead ribozyme, the three pyrimidine positions are 7, 4 and 3. For construction of the libraries, the ribozyme positions are numbered 3' to 5': position 24=7, position 27=4, and position 28=3 (see FIG. 7). The remainder of the hammerhead ribozyme "templates" remained constant and is based on a previously described hammerhead motif (Thompson et al., U.S. Pat. No. 5,610, 052, incorporated by reference herein). The starting ribozyme template is targeted against nucleotide position 823 of k-ras mRNA (Site A). Down regulation of this message, as a result of ribozyme action, results in the inability of the cells to proliferate. Therefore in order to optimize a ribozyme, we chose to identify "variants" which were successful in inhibiting cell proliferation.

Cell Culture Assay
Ribozyme:Lipid Complex formation

Ribozymes and LipofectAMINE were combined DMEM at final concentrations of 100 nM and 3.6 µM, respectively. Complexes were allowed to form for 15 min at 37° C. in the absence of serum and antibiotics.

Proliferation Assay

Primary rat aortic smooth muscle cells (RASMC) were seeded at a density of 2500 cells/well in 48 well plates. Cells were incubated overnight in DMEM, supplemented with 20% fetal bovine serum (FBS), Na-pyruvate, penicillin (50 U/ml), and streptomycin (50 µg/ml). Subsequently cells were rendered quiescent by a 48 h incubation in DMEM with 0.5% FBS.

Cells were incubated for 1.5 h with serum-free DMEM ribozyme:lipid complexes. The medium was replaced and cells were incubated for 24 h in DMEM with 0.25% FCS.

Cells were then stimulated with 10% FBS for 24 h. $^3$H-thymidine (0.3 µCi//well) was present for the last 12 h of serum stimulation.

At the end of the stimulation period the medium was aspirated and cells were fixed in icecold TCA (10%) for 15 min. The TCA solution was removed and wells were washed once with water. DNA was extracted by incubation with 0.1 N NaOH at RT for 15 min. Solubilized DNA was quantitatively transferred to minivials. Plates were washed once with water. Finally, $^3$H-thymidine incorporation was determined by liquid scintillation counting.

A strategy for optimizing the three (number of Class=3) pyrimidine residues is illustrated in FIG. 8. Ten different nucleotide analogs (illustrated in FIG. 9) were chosen to construct the ribozyme library (n=10). In the first step, ten different pools (Class 1) were synthesized by the mix and split approach described herein. Positions 24 and 27 were random and position 28 was fixed with each of the ten different analogs. The ten different pools were formulated with a cationic lipid (Jarvis et al., 1996, *RNA*, 2,419; incorporated by reference herein), delivered to cells in vitro, and cell proliferation was subsequently assayed (see FIG. 10). A positive control (active ribozyme) inhibited cell proliferation by ~50% and an inactive control (inactive) resulted in a less than 25% reduction in cell proliferation. The ten ribozyme pools resulted in intermediate levels of reduction. However, the best pool could be identified as $X_{24}X_{27}2'$-MTM-$U_{28}$ (positions 24 and 27 random; 2'-O-MTM-U at position 28). Therefore, a second ribozyme library (Class 2) was synthesized with position 28 constant (2'-O-MTM-U); position 24 was random ($X_{24}$) and position 27 was fixed with each of the ten different analogs ($F_{27}$). Again, the ten pools were assayed for their ability to inhibit cell proliferation. Among Class 2, two pools inhibited proliferation equally well: $X_{24}2'$-C-allyl-$U_{27}2'$-O-MTM-$U_{28}$ and $X_{24}2'$-O-MTM-$C_{27}2'$-O-MTM-$U_{28}$. Because a single "winner" could not be identified in Class 2, position 27 was made constant with either 2'-C-allyl-U or with 2'-O-MTM-C and the ten analogs were placed individually at position 24 (Class 3). Therefore in Class 3, twenty different ribozymes were assayed for their ability to inhibit cell proliferation. Because both positions 27 and 28 are constant, the final twenty ribozymes contain no random positions. Thus in the final group (Class 3), pure ribozymes and not pools were assayed. Among the final groups four ribozymes inhibited cell proliferation to a greater extent than the control ribozyme (FIG. 10). These four winners are illustrated in FIG. 11A. FIG. 11B shows general formula for four different motifs. A formula for a novel ribozyme motif is shown in FIG. 12.

Example 3

Identifying Accessible Sites for Ribozyme Action in a Target

In the previous two examples (1 and 2), positions within the catalytic domain of the hammerhead ribozyme were optimized. The number of groups that needed to be tested equals=the total number of positions within the ribozyme that were chosen to be tested. A similar procedure can be used on the binding arms of the ribozyme. The sequence of the binding arms determines the site of action of the ribozyme. The combinatorial approach can be used to identify those sites by essentially testing all possible arm sequences. The difficulty with this approach is that ribozymes require a certain number of base pairs (12–16) in order bind tightly and specifically. According to the procedure outlined above, this would require 12–16 different groups of ribozyme pools; 12–16 positions would have to be optimized which would require 12–16 different groups being synthesized and tested. Each pool would contain the four different nucleotides (A, C, U and G) or nucleotide analogs (n=4). It would be very time consuming to test each group, identify the best pool, synthesize another group of ribozyme pools with one additional position constant, and then repeat the procedure until all 12–16 groups had been tested. However it is possible to decrease the number of groups by testing multiple positions within a single group. In this case, the number of pools within a group equals the number of nucleotides or analogs in the random mixture (i.e. n) to the w power, where w equals the number of positions fixed in each group. The number of groups that need to be synthesized to optimize the final ribozyme equals the total number of positions to be optimized divided by the number of positions (w) tested within each group. The number of pools in each group=$n^w$. The number of groups=total number of positions/w.

For example, FIG. 17 illustrates this concept on a hammerhead ribozyme containing 12 base pair binding arms. Each of the two binding arms form 6 base pairs with ifts corresponding RNA target. It is important to note that for the hammerhead ribozyme one residue (A15.1) must remain constant; A15.1 forms a base pair with a substrate nucleotide (U16.1) but is also absolutely required for ribozyme activity. It is the only residue within the hammerhead ribozyme that is part of both the catalytic domain, and the binding domain (arms). In the example this position is not optimized. In the first Group, three positions are fixed (designated F) with the four different 2'-O-methyl nucleotides (A, C, U and G). The 2'-O-methyl modification stabilizes the ribozyme against nuclease degradation and increases the binding affinity with it's substrate. The total number of pools in each group does not equal n, as in the previous examples. The number of pools in each group equals $4^3$=(four analogs)^(number of positions fixed; 3)=64. in all 64 pools, all other positions in the arm are made random (designated X) by the nucleotide mixing building block approach. The catalytic domain is not considered in this example and therefore remains part of the ribozyme template (i.e. constant).

In the first step, all 64 ribozyme pools are tested. This test may be cleavage in vitro (see Example 1), or efficacy in a cellular (see Example 2) or animal model, or any other assayable end-point. This end-point however, should be specific to a particular RNA target. For example, if one wishes to identify accessible sites within the mRNA of GeneB, a suitable end-point would be to look for decreased levels of GeneB mRNA after ribozyme treatment. After a winning pool is identified, since each pool specifies the identity of three positions (w), three positions can be made constant for the next group (Class 2). Class 2 is synthesized containing 64 different pools; three positions that were fixed in Class 1 are now constant (designated Z), three more positions are fixed (F), and the remaining positions (X) are a random mix of the four nucleotides. The 64 pools are assayed as before, a winning pool is identified, allowing three more positions to be constant in the next Class of ribozyme pools (Class 3) and the process is repeated again. In the final Class of ribozymes (Class 4), only two positions are fixed, all other positions have been previously fixed. The total number of ribozymes is therefore $n^w=4^2=16$; these ribozymes also contain no random positions. In the final step (step 4), the 16 ribozymes are tested; the winning ribozyme defines the sequence of the binding arms for a particular target.

Fixing multiple positions within a single group it is possible to decrease the overall number of groups that need to be tested. As mentioned, this is particularly useful when a large number of different positions need to be optimized. A second advantage to this approach is that it decreases the complexity of molecules in each pool. If one would expect that many combinations within a given pool will be inactive, by decreasing the number of different ribozymes in each pool, it will be easier to identify the "winning" pool. in this approach, a larger number of pools have to be tested in each group, however, the number of groups is smaller and the complexity of each ribozyme pool is smaller. Finally, it should be emphasized there is not a restriction on the number of positions or analogs that can be tested. There is also no restriction on how many positions are tested in each group.

Example 4

Identifying New RNA Targets for Ribozymes

As described above for identifying ribozyme-accessible sites, the assayed used to identify the "winning" pool of ribozymes is not defined and may be cleavage in vitro (see Example 1), or efficacy in a cellular (see Example 2) or animal model, or any other assayable end-point. For identifying accessible sites, this end-point should be specific to a particular RNA target (e.g. mRNA levels). However, the end-point could also be nonspecific. For example, one could choose a disease model and simply identify the winning ribozyme pool based on the ability to provide a desired effect. In this case, it is not even necessary to know what the cellular target that is being acted upon by the ribozyme is. One can simply identify a ribozyme that has a desired effect. The advantage to this approach is that the sequence of the binding arms will be complementary to the RNA target It is therefore possible to identify gene products that are involved in a disease process or any other assayable phenotype. One does not have to know what the target is prior to starting the study. The process of identifying an optimized ribozyme (arm combinatorial) identifies both the drug (ribozyme) and the RNA target, which may be a known RNA sequence or a novel sequence leading to the discovery of new genes.

Example 5

Identifying New Ribozyme Catalytic Domains

In the previous two examples, positions within the binding domain of the hammerhead ribozyme were varied and positions within the catalytic domain were not changed. Conversely, it is possible to vary positions within the catalytic domain, without changing positions within the binding arms, in order to identify new catalytic motifs. An example is illustrated in FIG. 18. The hammerhead ribozyme, for example comprises about 23 residues within the catalytic domain. It is unclear how many of these 23 positions are required to obtain a functional catalytic domain, however it is reasonable to presume that if a large number of functionally diverse nucleotide analogs can be used to construct the pools, a relatively small number of positions could constitute a functional catalytic domain. This may especially be true if analogs are chosen that one would expect to participate in catalysis (e.g. acid/base catalysts, metal binding, etc. ). In the example illustrated in FIG. 18, four positions (designated 1, 2, 3 and 4) are chosen. In the first step, ribozyme libraries (Class 1) are constructed: position 1 is fixed ($F_1$) and positions 2, 3 and 4 are random ($X_2$, $X_3$ and $X_4$, respectively). In step 2, the pools (the number of pools tested depends on the number of analogs used; n) are assayed for activity. This testing may be performed in vitro or in a cellular or animal model. Whatever assay that is used, the pool with the most activity is identified and libraries (class 2) are again synthesized with position 1 now constant ($Z_1$) with the analog that was identified in class 1. In class 2, position 2 is fixed ($F_2$ and positions 3 and 4 are random ($X_3$ and $X_4$). This process is repeated until every position has been made constant, thus identifying the catalytic domain or a new motif.

Example 6

Determination of Coupling Efficiency of the Phosphoramidite Derivatives of 2'-C-allyl-uridine, 1; 4'-thio-cytidine, 2; 2'-methylthiomethyl-uridine, 3; 2'-methylthiomethyl-cytidine, 4; 2'-amino-uridine, 5; N3-methyl-uridine, 6; 1-β-D-(ribofuranosyl)-pyridin-4-one, 7; 1-β-D-(ribofuranosyl)-pyridin-2-one, 8; 1-β-D-(ribofuranosyl)-phenyl, 9; 6-methyl-uridine, 10 to be used in a split and mix approach.

The determination of the coupling efficiency of amidites 1 to 10 was assessed using ten model sequences agacX-GAuGa (where upper case represents ribonucleotide residues, lower case represents 2'-O-methyl ribonucleotide residues and X is amidites 1 to 10, to be used in the construction of a hammerhead ribozyme library wherein the modified amidites 1 to 10 would be incorporated. Ten model sequences were synthesized using ten 0.112 g aliquots of 5'-O-DMT-2'-O-Me-Adenosine Polystyrene (PS) solid-support loaded at 22.3 μmol/g and equivalent to a 2.5 μmol scale synthesis. Synthesis of these ten decamers were performed on ABI 394 DNA synthesizer (Applied Biosystems, Foster City, Calif.) using standard nucleic acid synthesis reagents and synthesis protocols, with the exception of an extended (7.5 min) coupling time for the ribonucleoside phosphoramidites and phosphoramidites 1, 2, 3, 4, 6, 7, 8, 9, 10, 12.5 min coupling time for the 2'-amino-uridine phosphoramidite, amidite 5 and 2.5 min coupling time for the 2'-O-methyl nucleoside phosphoramidites.

Oligomers were cleaved from the solid support by treatment with a 3:1 mixture of ammonium hydroxide:absolute ethanol at 65 degree C. for 4 hrs followed by a desilylation treatment and butanol precipitation as described in Wincott et al. (Wincott et al, *Nucleic Acids Res,* 1995, 23, 2677–2684; incorporated by reference herein). Oligonucleotides were analyzed directly on an anion-exchange HPLC column (Dionex, Nucleopac, PA-100, 4×250 mm) using a gradient of 50% to 80% of B over 12 minutes (A=10 mM sodium perchlorate, 1 mM Tris, pH 9.43; B=300 mM sodium perchlorate, 1 mM Tris, pH 9.36) and a Hewlett-Packard 1090 HPLC system.

The average stepwise yield (ASWY), indicating the coupling efficiency of phosphoramidites, 1 to 10, were calculated from peak-area percentages according to the equation ASWY=(FLP%)$^{1/n}$ where FLP% is the percentage full-length product in the crude chromatogram and n the number of synthesis cycles. ASWY ranging from of 96.5% to 97.5% were obtained for phosphoramidites, 1 to 10. The experimental coupling efficiencies of the phosphoramidites 1 to 10, as determined using a standard spectrophotometric dimethoxytrityl assay were in complete agreement with the ASWY and were judged satisfactory to proceed with the X24, X27, X28 ribozyme library synthesis.

Example 7

Determination of Optimal Relative Concentration of a Mixture of 2'-O-methyl-guanosine, cytidine, uridine and adenosine providing equal representation of the four nucleotides A mixture N, composed of an equimolar mixture of the four 2'-O-Me-nucleoside phosphoramidites (mG=2'-O-methyl guanosine; mA=2'-O-methyl adenosine; mC=2'-O-methyl cytidine; mU=2'-O-methyl uridine) was used in the synthesis of a model sequence TTXXXXTTB, where T is 2'-deoxy-thymidine and B is a 2'-deoxy-inverted abasic polystyrene solid-support as described in Example 6. After standard deprotection (Wincott et al., supra), the crude nonamer was analyzed on an anion-exchange HPLC column (see example 1). From the HPLC analysis, an averaged stepwise yield (ASWY) of 99.3% was calculated (see example 6) indicating that the overall coupling efficiency of the mixture N was comparable to that of 2'-deoxythymidine. To further assess the relative incorporation of each of the components within the mixture, N, the full-length product TTXXXXTTB (over 94.3% at the crude stage) was further purified and subjected to base composition analysis as described herein. Purification of the FLP from the failures is desired to get accurate base composition.

Base Composition Analysis Summary

A standard digestion/HPLC analysis was performed: To a dried sample containing 0.5 A.sub.260 units of TTXXXXTB, 50 μl mixture, containing 1 mg of nuclease P1 (550 units/mg), 2.85 ml of 30 mM sodium acetate and 0.3 ml of 20 mM aqueous zinc chloride, was added. The reaction mixture was incubated at 50 degrees C. overnight. Next, 50 μl of a mixture comprising 500 μl of alkaline phosphatase (1 units/μl), 312 μl of 500 mM Tris pH 7.5 and 2316 μl water was added to the reaction mixture and incubated at 37 degrees C. for 4 hours. After incubation, the samples were centrifuged to remove sediments and the supernatant was analyzed by HPLC on a reversed-phase C18 column equilibrated with 25 mM KH2PO4. Samples were analyzed with a 5% acetonitrile isocratic gradient for 8 min followed by a 5% to 70% acetonitrile gradient over 8 min.

The HPLC percentage areas of the different nucleoside peaks, once corrected for the extinction coefficient of the individual nucleosides, are directly proportional to their molar ratios.

The results of these couplings are shown in Table III.

Example 8

A Non-competitive coupling method for the preparation of the X24. X27 and N28 ribozyme library 5'-a$_s$c$_s$a$_s$a$_s$ag aFX GAX Gag gcg aaa gcc Gaa Agc ccu cB-3' wherein 2'-C-allyl-uridine, 1; 4'-thio-cytidine, 2; 2'-methylthiomethyl-uridine, 3; 2'-methylthiomethyl-cytidine, 4; 2'-amino-uridine, 5; N3-methyl-urdine, 6;1-β-D-(ribofuranosyl)-pyrimidine-4-one, 7; 1-β-D-(ribofuranosyl)-pyrimidine-2-one, 8; 1-β-D-(ribofuranosyl)-phenyl, 9; and/or 6-methyl-uridine, 10 are incorporated at the X24, X27 and F28 positions through the mix and split approach The synthesis of ten different batches of 2.5 μmol scale Gag gcg aaa gcc Gaa Agc ccu cB sequence was performed on 2'-deoxy inverted abasic polystyrene solid support B on a 394 ABI DNA synthesizer (Applied Biosystems, Foster City, Calif.). These ten aliquots were then separately reacted with phosphoramidite building blocks 1 to 10 according to the conditions described in example 6. After completion of the individual incorporation of amidites 1 to 10, their coupling efficiencies were determined to be above 95% as judged by trityl monitoring. The 10 different aliquots bearing the ten different sequences were mixed thoroughly and divided into ten equal subsets. Each of these aliquots were then successively reacted with ribo-A, ribo-G amidites and one of the amidites 1 to 10. The ten aliquots were combined, mixed and split again in 10 subsets. At that point, the 10 different polystyrene aliquots, exhibiting the following sequence: X GAX Gag gcg aaa gcc Gaa Agc ccu cB, were reacted again with amidites 1 to 10 separately. The aliquots

| Nucleoside | dT 0.1M | 2'-OMe-C 0.025M | 2'-OMe-U 0.025M | 2'-OMe-G 0.025M | 2'-OMe-A 0.025M |
|---|---|---|---|---|---|
| % area | 43.81 | 6.04 | 14.07 | 18.54 | 17.54 |
| Epsilon 260 nm | 8800 | 7400 | 10100 | 11800 | 14900 |
| moles | 0.00498 | 0.00082 | 0.00139 | 0.00157 | 0.00118 |
| equivalent | 4 | 0.656 | 1.119 | 1.262 | 0.946 |

As can be seen in Table III, the use of an equimolar mixture of the four 2'-O-methyl phosphoramidites does not provide an equal incorporation of all four amidites, but favors 2'-O-methyl-U and G and incorporates 2'-O-methyl-A and C to a lower efficiency. To alleviate this, the relative concentrations of 2'-O-methyl-A, G, U and C amidite were adjusted using the inverse of the relative incorporation as a guide line. After several fterations, the optimized mixture providing nearly identical incorporation of all four amidites was obtained as shown in Table IV below. The relative representation do not exceed 12% difference between the most and least incorporated residue corresponding to a +/−6% deviation from equimolar incorporation.

were not mixed, but kept separate to obtain a unique residue at the 28th position of each of the ten pools. The ribozyme synthesis was then finished independently to yield ten random ribozymes pools. Each pool comprises a 3'-terminal inverted abasic residue B, followed by the sequence Gag gcg aaa gcc Gaa Agc ccu c, followed with one random position X in the 24th position corresponding to a mixture of amidites 1 to 10, followed by the sequence GA, followed one random position X in the 27th position corresponding to a mixture of amidites 1 to 10, followed by a fixed monomer F (one of the amidites 1 to 10) in the 28th position and finally the 5'-terminal sequence a$_s$c$_s$a$_s$a $_s$a g a. This is represented by the sequence notation 5'-a$_s$c$_s$a$_s$a$_s$ag aFX GAX Gag gcg aaa gcc

| Nucleoside | dT 0.1M | 2'-OMe-C 0.032M | 2'-OMe-U 0.022M | 2'-OMe-G 0.019M | 2'-OMe-A 0.027M |
|---|---|---|---|---|---|
| % area | 44.47 | 8.91 | 11.81 | 15.53 | 19.28 |
| Epsilon 260 nm | 8800 | 7400 | 10100 | 11800 | 14900 |
| moles | 0.00505 | 0.00120 | 0.00117 | 0.00132 | 0.00129 |
| equivalent | 4 | 0.953 | 0.926 | 1.042 | 1.024 |

Gaa Agc ccu cB-3', in which X are random positions and F is a unique fixed position. The total complexity of such a ribozyme library was $10^3$ or 1,000 members separated in 10 pools of 100 different ribozyme sequences each.

Example 9
Competitive Coupling Method (Monomer Mixing Approach) for the Preparation of the $x_{2-6}$ and $X_{30-35}$ "Binding Arms" Ribozyme Library Synthesis of 5'-$x_s x_s x$FF cuG Au G Agg ccg uua ggc cGA AAF xxx xB-3' is described, with F being a defined 2'-O-methyl-ribonucleoside chosen among 2'-O-methyl-ribo-adenosine (mA), -guanosine (mG), -cytidine (mC), -uridine (mU) and x being an equal mixture of 2'-O-methyl-ribo-adenosine, -guanosine, -cytidine, -uridine.

The syntheses of this ribozyme library was perfomfned with an ABI 394 DNA synthesizer (Applied Biosystems, Foster City, Calif.) using standard nucleic acid synthesis reagents and synthesis protocols, with the exception of an extended (7.5 min) coupling time for the ribonucleoside phosphoramidites (upper case) and 2'-amino-uridine phosphoramidite, u, (2.5 min) coupling time for the 2'-O-methyl-ribonucleoside phosphoramidites (lower case) and the 2'-O-methyl-ribonucleoside phosphoramidites mixture, n.

Sixty four (64) batches of 0.086 g aliquots of 3'-O-DMT-2'-deoxy-inverted abasic-Polystyrene (B) solid-support loaded at 29 μmol/g and equivalent to a 2.5 μmol scale synthesis were individually reacted with a 27:32:19:22/v:v:v:v mixture, x, of mA:mC:mG:mU diluted in dry acetonitrile to 0.1 M as described in example 2. This synthesis cycle was repeated for a total of four times. The 64 aliquots were then grouped into four subsets of sixteen aliquots (Class 1) that were reacted with either mA, mG, mC, mU to synthesize the n6 position. This accomplished, the sequence: 5'-cuG Au G Agg ccg uua ggc cGA AA was added onto the 6 position of the 64 aliquots constituting Class 1. Each subset of Class 1 was then divided into four subsets of four aliquots (Class 2) that were reacted with either mA, mG, mC, mU to synthesize the F30 position. Each subset of Class 2 was then divided into four subsets of one aliquot (Class 3) that were reacted with either mA, mG, mC, mU to synthesize the F31 position. Finally, the random sequence 5'-$x_s x_s x x$ was added onto each of the 64 aliquots.

The ribozyme library yielded sixty four random ribozymes pools each having an equal mixture of the four 2'-O-methyl-nucleoside at the position x2 to 6 and x30 to 35, and a defined 2'-O-methyl-nucleoside chosen among mA, mC, mG, mU at the positions F6, F30 and F31. The total complexity of such a "binding arms" ribozyme library was $4^{11}$ or 4,194,304 members separated in 64 pools of 65,536 different ribozyme sequences each.

Example 10
Competitive Coupling Method (Monomer Mixing Approach) for the Preparation of the Position 15 to 18 "Loop II" Ribozyme Library Synthesis of 5' UCU CCA UCU GAU GAG GCC XXF XGG CCG AAA AUC CCU 3' is described, with F being a defined ribonucleoside chosen among adenosine (A), guanosine (G), cytidine (C), undine (U) and X being an equal mixture of adenosine (A), guanosine (G), cytidine (C), uridine (U).

The syntheses of this ribozyme library was performed with an ABI 394 DNA synthesizer (Applied Biosystems, Foster City, Calif.) using standard nucleic acid synthesis reagents and synthesis protocols, with the exception of an extended (7.5 min) coupling time for the ribonucleoside phosphoramidites (A, G, C, U) and the ribonucleoside phosphoramidite mixture, X.

Four batches (4) of 2.5 μmol scale of GG CCG AAA AUC CCU sequence were synthesized on 0.085 g samples of 5'-O-DMT-2'-O-TBDMS-3'-succinyl-uridine-Polystyrene (U) solid-support loaded at 29.8 μmol/g. To synthesize the position X15, the four aliquots of solid-supports were individually reacted with a 30:26:24:20/v:v:v:v mixture, X, of A:C:G:U diluted in dry acetonitrile to 0.1 M according to the optimized conditions for the DNA phosphoramidites mixed-base coupling as described in the DNA Synthesis Course Manual published by Perkin-Elmer-Applied Biosystem Division. (DNA Synthesis Course Manual: Evaluating and isolating synthetic oligonucleotides, the complete guide, p. 2–4, Alex Andrus, August 1995). The four aliquots of solid-supports were then individually reacted with either of the four ribonucleoside phosphoramidites (A, G, C, U) to create the F16 position. The position X17 and X18 were then added onto the F16 (either A, G, C or U) of the four aliquots of solid-supports by repeating twice the same procedure used for the position X15.

The synthesis of the ribozyme library was then. ended by adding the sequence 5'-UCU CCA UCU GAU GAG GCC on the position X18 of each of the four subsets of the ribozyme library. The ribozyme library yielded four random ribozymes pools that each have an equal mixture of the four ribonucleoside (A, G, C and U) at the position X15, X17 and X18, and a discrete ribonucleoside chosen among A, C, G or U at the positions F16. The total complexity of such a loop II ribozyme library was 256 members separated in 4 pools of 64 different ribozyme sequences.

Diagnostic Uses

Enzymatic nucleic acids of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, nbozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by. determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention might have many of the same applications for the study of RNA that DNA restriction endonucleases have for the study of DNA (Nathans et al., 1975 Ann. Rev. Biochem. 44:273). For example, the pattern of restriction fragments could be used to establish sequence relationships between two related RNAs, and large RNAs could be specifically cleaved to fragments of a size more useful for study. The ability to engineer sequence specificity of the ribozyme is Ideal for cleavage of RNAs of unknown sequence.

Other embodiments are within the following claims.

TABLE 1

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.
Additional protein cofactors required in some cases to help folding and maintainance of the active structure [1].
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [2,3].
Complete kinetic framework established for one ribozyme [4,5,6,7].
Studies of ribozyme folding and substrate docking underway [8,9,10].
Chemical modification investigation of important residues well established [11,12].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [13].
RNASe P RNA (M1 RNA)

Size: ~290 to 400 nucleotides.
RNA portion of a ubiquitous ribonucleoprotein enzyme.
Cleaves tRNA precursors to form mature tRNA [14].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [15,16]
Important phosphate and 2' OH contacts recently identified [17,18]
Group II Introns Size: >1000 nucleotides.
Trans cleavage of target RNAs recently demonstrated [19,20].
Sequence requirements not fully determined.
Reaction mechanism: 2'-OH of an internal adenosine generates cleavage products with 3'-OH and a "lariat" RNA containing a 3'-5' and a 2'-5' branch point.
Only natural ribozyme with demonstrated participation in DNA cleavage [21,22] in addition to RNA cleavage and ligation.
Major structural features largely established through phylogenetic comparisons [23].
Important 2' OH contacts beginning to be identified [24]
Kinetic framework under development [25]
Neurospora VS RNA Size: ~144 nucleotides.
Trans cleavage of hairpin target RNAs recently demonstrated [26].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

TABLE 1-continued

Characteristics of naturally occurring ribozymes

Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products
with 2',3'-cyclic phosphate and 5'-OH ends.
14 known members of this class. Found in a number of plant pathogens (virusoids) that
use RNA as the infectious agent.
Essential structural features largely defined, including 2 crystal structures [ ]
Minimal ligation activity demonstrated (for engineering through in vitro selection) [ ]
Complete kinetic framework established for two or more ribozymes [ ].
Chemical modification investigation of important residues well established [ ].
Hairpin Ribozyme Size: ~50 nucleotides.
Requires the target sequence GUC immediately 3' of the cleavage site.
Binds 4–6 nucleotides at the 5'-side of the cleavage site and a variable number to the 3'-
side of the cleavage site.
Reaction mechanism: attack by 2'-OH 5' to the scissile bond to generate cleavage products
with 2',3'-cyclic phosphate and 5'-OH ends.
3 known members of this class. Found in three plant pathogen (satellite RNAs of the
tobacco ringspot virus, arabis mosaic virus and chicory yellow mottle virus) which uses
RNA as the infectious agent.
Essential structural features largely defined [$^{27,28,29,30}$]
Ligation activity (in addition to cleavage activity) makes ribozyme amenable to
engineering through in vitro selection [$^{31}$]
Complete kinetic framework established for one ribozyme [$^{32}$].
Chemical modification investigation of important residues begun [$^{33,34}$].
Hepatitis Delta Virus (HDV) Ribozyme Size: ~60 nucleotides.
Trans cleavage of target RNAs demonstrated [$^{35}$].
Binding sites and structural requirements not fully determined, although no sequences 5' of
cleavage site are required. Folded ribozyme contains a pseudoknot structure [$^{36}$].
Reaction mechanism: attack by 2'-OH 5' to the scissile bond to generate cleavage products
with 2',3'-cyclic phosphate and 5'-OH ends.
Only 2 known members of this class. Found in human HDV.
Circular form of HDV is active and shows increased nuclease stability [$^{37}$]

[1]Mohr, G.; Caprara, M. G.; Guo, Q.; Lambowitz, A. M. Nature, 370, 147–150 (1994).
[2]Michel, Francois; Westhof, Eric. Slippery substrates. Nat. Struct. Biol. (1994), 1(1), 5–7.
[3]Lisacek, Frederique; Diaz, Yolande; Michel, Francois. Automatic identification of group I
intron cores in genomic DNA sequences. J. Mol. Biol. (1994), 235(4), 1206–17.
[4]Herschlag, Daniel; Cech, Thomas R.. Catalysis of RNA cleavage by the *Tetrahymena ther-
mophila* ribozyme. 1. Kinetic description of the reaction of an RNA substrate complementary
to the active site. Biochemistry (1990), 29(44), 1015–71.
[5]Herschlag, Daniel; Cech, Thomas R.. Catalysis of RNA cleavage by the *Tetrahymena ther-
mophila* ribozyme. 2. Kinetic description of the reaction of an RNA substrate that forms a
mismatch at the active site. Biochemistry (1990), 29(44), 10172–80.
[6]Knitt, Deborah S.; Herschlag, Daniel. pH Dependencies of the Tetrahymena Ribozyme
Reveal an Unvonventional Origin of an Apparent pKa. Biochemistry (1996), 35(5), 1560–70.
[7]Bevilacqua, Philip C.; Sugimoto, Naoki; Turner, Douglas H.. A mechanistic framework for
the second step of splicing catalyzed by the Tetrahymena ribozyme. Biochemistry (1996),
35(2), 648–58.
[8]Li, Yi; Bevilacqua, Philip C.; Mathews, David; Turner, Douglas H.. Thermodynamic and
activation parameters for binding of a pyrene-labeled substrate by the Tetrahymena ribozyme:
docking is not diffusion-controlled and is driven by a favorable entropy change. Biochemistry
(1995), 34(44), 14394–9.
[9]Banerjee, Aloke Raj; Turner, Douglas H.. The time dependence of chemical modification
reveals slow steps in the folding of a group I ribozyme. Biochemistry (1995), 34(19),
6504–12.
[10]Zarrinkar, Patrick P.; Williamson, James R. The P9.1–P9.2 peripheral extension helps guide
folding of the Tetrahymena ribozyme. Nucleic Acids Res. (1996), 24(5), 854–8.
[11]Strobel, Scott A.; Cech, Thomas R.. Minor groove recognition of the conserved G.cntdot.U
pair at the Tetrahymena ribozyme reaction site. Science (Washington, D.C.) (1995), 267(5198),
675–9.
[12]Strobel. Scott A.; Cech, Thomas R.. Exocyclic Amine of the Conserved G.cntdot.U Pair at
the Cleavage Site of the Tetrahymena Ribozyme Contributes to 5'-Splice Site Selection and
Transition State Stabilization. Biochemistry (1996), 35(4), 1201–11.
[13]Sullenger, Bruce A.; Cech, Thomas R. Ribozyme mediated repair of defective mRNA by
targeted trans-splicing. Nature (London) (1994), 371(6498), 619–22.
[14]Robertson, H. D.; Altman, S.; Smith, J. D. J. Biol Chem., 247, 5243–5251 (1972).

TABLE 1-continued

Characteristics of naturally occurring ribozymes

[15]Forster, Anthony C.; Altman, Sidney. External guide sequences for an RNA enzyme. Science (Washington, D.D., 1883–) (1990), 249(4970), 783–6.
[16]Yuan, Y.; Hwang, E. S.; Altman, S. Targeted cleavage of mRNA by human RNase P. Proc. Natl. Acad. Sci. USA (1992) 89, 8006–10.
[17]Harris, Michael E.; Pace, Norman R.. Identification of phosphates involved in catalysis by the ribozyme RNase P RNA. RNA (1995), 1(2), 210–18.
[18]Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
[19]Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.
[20]Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
[21]Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.
[22]Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with intron ribozymes that cleave DNA and RNA linkages with similar efficiency, and lack contacts with substrate 2'-hydroxyl groups. Chem. Biol. (1995), 2(11), 761–70.
[23]Michel, Francois; Ferat, Jean Luc. Structure and activities of group II introns. Annu. Rev. Biochem. (1995), 64, 435–61.
[24]Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
[25]Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.
[26]Guo, Hans C. T.; Collins, Richard A.. Efficient trans-cleavage of a stem-loop RNA substrate by a ribozyme derived from Neurospora VS RNA. EMBO J. (1995), 14(2), 368–76.
[27]Hampe., Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
[28]Chowrira, Bharat M.; Berzal-Herranz, Alfredo; Burke, John M.. Novel guanosine requirement for catalysis by the hairpin ribozyme. Nature (London) (1991), 354(6351), 320–2.
[29]Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
[30]Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
[31]Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
[32]Hegg, Lisa A.; Fedor, Martha J.. Kinetics and Thermodynamics of Intermolecular Catalysis by Hairpin Ribozymes. Biochemistry (1995), 34(48), 15813–28.
[33]Grasby, Jane A.; Mersmann, Karin; Singh, Mohinder; Gait, Michael J.. Purine Functional Groups in Essential Residues of the Hairpin Ribozyme Required for Catalystic Cleavage of RNA. Biochemistry (1995), 34(12), 4068–76.
[34]Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside bases in internal loop B of the hairpin ribozyme: implications for secondary structure. Nucleic Acids Res. (1996), 24(4), 573–81.
[35]Perrotta, Anne T.; Been, Michael D.. Cleavage of oligoribonucleotides by a ribozyme derived from the hepatitis .delta. virus RNA sequence. Biochemistry (1992), 31(1), 16–21.
[36]Perrotta, Anne T.; Been, Michael D.. A pseudoknot-like structure required for efficient self-cleavage of hepatitis delta virus RNA. Nature (London) (1991), 350(6317), 434–6.
[37]Puttaraju, M.; Perrotta, Anne T.; Been, Michael D.. A circular trans-acting hepatitis delta virus ribozyme. Nucleic Acids Res. (1993), 21(18), 4253–8.

TABLE II

2.5 µmol RNA Synthesis Cycle

| Reagent | Equivalents | Amount | Wait Time* |
|---|---|---|---|
| Phosphoramidites | 6.5 | 163 µL | 25 |
| S-Ethyl Tetrazole | 23.8 | 238 µL | 25 |
| Acetic Anhydride | 100 | 233 µL | 5 sec |
| N-Methyl Imidazole | 186 | 233 µL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

What is claimed is:

1. A nucleic acid molecule in a purified form with an endonuclease activity, comprising ribonucleotides and having the formula I:

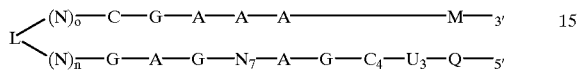

wherein, N is independently a nucleotide or a non-nucleotide linker, which may be same or different; M and Q are independently oligonucleotides of length sufficient to stably interact with a target nucleic acid molecule; o and n are integers greater than or equal to 1, wherein if $(N)_o$ and $(N)_n$ are nucleotides, (N)o and (N)n are optionally able to interact by hydrogen bond interaction; L is a linker which may be present or absent, but when present, is a nucleotide and/or a non-nucleotide linker, which may be a single-stranded and/or double-stranded region; represents a chemical linkage; U3, C4 and N7 indicate the relative position of each said nucleotide in the nucleic acid molecule, and A, C, U and G represent adenosine, cytidine, uridine and guanosine nucleotides, respectively.

2. A nucleic acid molecule with catalytic activity, comprising ribonucleotides having the formula II:

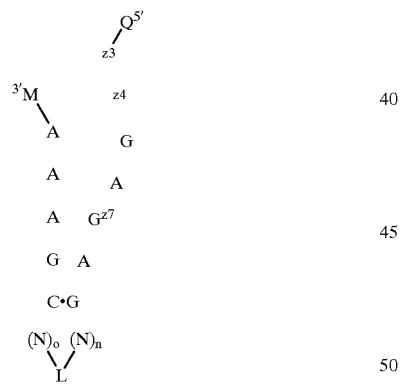

wherein, N is independently a nucleotide or a non-nucleotide linker, which may be same or different; M and Q are independently oligonucleotides of length sufficient to stably interact with a target nucleic acid molecule; o and n are integers greater than or equal to 1, wherein if $(N)_o$ and $(N)_n$ are nucleotides, (N)o and (N)n are optionally able to interact by hydrogen bond interaction; L is a linker which may be present or absent, but when present, is a nucleotide and/or a non-nucleotide linker, which may be a single-stranded and/or double-stranded region; Z3 is 2'-methylthiomethyl uridine; Z4 is 2'-C-allyl uridine; Z7 is 6-methyl uridine; represents a chemical linkage; and A, and G represent adenosine and guanosine nucleotides, respectively.

3. A nucleic acid molecule with catalytic activity, comprising ribonucleotides and having the formula III:

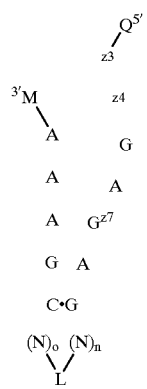

wherein, N is independently a nucleotide or a non-nucleotide linker, which may be same or different; M and Q are independently oligonucleotides of length sufficient to stably interact with a target nucleic acid molecule; o and n are integers greater than or equal to 1, wherein if $(N)_o$ and $(N)_n$ are nucleotides, (N)o and (N)n are optionally able to interact by hydrogen bond interaction; L is a linker which may be present or absent, but when present, is a nucleotide and/or a non-nucleotide linker, which may be a single-stranded and/or double-stranded region; Z3 is 2'-methylthiomethyl uridine; Z4 is 2'-methylthiomethyl cytidine; Z7 is 6-methyl uridine; represents a chemical linkage; and A, and G represent adenosine and guanosine nucleotides, respectively.

4. A nucleic acid molecule with catalytic activity, comprising ribonucleotides and having the formula IV:

wherein, N is independently a nucleotide or a non-nucleotide linker, which may be same or different; M and Q are independently oligonucleotides of length sufficient to stably interact with a target nucleic acid molecule; o and n are integers greater than or equal to 1, wherein if $(N)_o$ and $(N)_n$ are nucleotides, (N)o and (N)n are optionally able to interact by hydrogen bond interaction; L is a linker which may be present or absent, but when present, is a nucleotide and/or a non-nucleotide linker, which may be a single-stranded and/or double-stranded region; Z3 is 2'-methylthiomethyl uridine; Z4 is 2'-methylthiomethyl cytidine; Z7 is 2'-C-allyl uridine; represents a chemical linkage; and A, anq G represent adenosine and guanosine nucleotides, respectively.

5. A nucleic acid molecule with catalytic activity, comprising ribonucleotides and having the formula V:

```
           Q5'
          /
        z3
   3'M       z4
      \
       A
            G
       A  A
       A  G^z7
       G  A
       C•G
      (N)o (N)n
        \ /
         L
``` wherein, N is independently a nucleotide or a non-nucleotide linker, which may be same or different; M and Q are independently oligonucleotides of length sufficient to stably interact with a target nucleic acid molecule; o and n are integers greater than or equal to 1, wherein if $(N)_o$ and $(N)_n$ are nucleotides, (N)o and (N)n are optionally able to interact by hydrogen bond interaction; L is a linker which may be present or absent, but when present, is a nucleotide and/or a non-nucleotide linker, which may be a single-stranded and/or double-stranded region; Z3 is 2'-methylthiomethyl uridine; Z4 is 2'-methylthiomethyl cytidine; Z7 is pyridine-4-one; and represents a chemical linkage; and A, and G represent adenosine and guanosine nucleotides, respectively.

6. The nucleic acid molecules of any of claims 1–5, wherein said $(N)_o$ and $(N)_n$ are nucleotides and said o and n are integers greater than or equal to 3.

7. The nucleic acid molecules of any of claims 1–5, wherein said L is nucleotide linker.

8. The nucleic acid molecule of any of claims 1–5, wherein said nucleic acid cleaves a separate nucleic acid molecule.

9. The nucleic acid molecule of claim 8, wherein said separate nucleic acid molecule is RNA.

10. The nucleic acid molecule of claim 8, wherein said nucleic acid comprises between 12 and 100 bases complementary to said separate nucleic acid molecule.

11. The nucleic acid molecule of claim 8, wherein said nucleic acid comprises between 14 and 24 bases complementary to said separate nucleic acid molecule.

12. A cell including the nucleic acid molecule of any of claims 1–5.

13. The cell of claim 12, wherein said cell is a mammalian cell.

14. The cell of claim 13, wherein said mammalian cell is a human cell.

15. An expression vector comprising nucleic acid sequence encoding at least one of the nucleic acid molecule of claim 1, in a manner which allows expression of that nucleic acid molecule.

16. A cell including the expression vector of claim 15.

17. The cell of claim 16, wherein said cell is a mammalian cell.

18. The cell of claim 16, wherein said cell is a human cell.

19. A pharmaceutical composition comprising the nucleic acid molecule of any of claims 1–5.

20. The nucleic acid molecule of claims 1–5, wherein said nucleic acid is chemically synthesized.

21. The expression vector of claim 15, wherein said vector comprises:
   a) a transcription initiation region;
   b) a transcription termination region;
   c) a gene encoding at least one said nucleic acid molecule; and
   wherein said gene is operably linked to said initiation region and said termination region, in a manner which allows expression and/or delivery of said nucleic acid molecule.

22. The expression vector of claim 15, wherein said vector comprises:
   a) a transcription initiation region;
   b) a transcription termination region;
   c) an open reading frame;
   d) a gene encoding at least one said nucleic acid molecule, wherein said gene is operably linked to the 3'-end of said open reading frame; and
   wherein said gene is operably linked to said initiation region, said open reading frame and said termination region, in a manner which allows expression and/or delivery of said nucleic acid molecule.

23. The expression vector of claim 15, wherein said vector comprises:
   a) a transcription initiation region;
   b) a transcription termination region;
   c) an intron;
   d) a gene encoding at least one said nucleic acid molecule; and
   wherein said gene is operably linked to said initiation region, said intron and said termination region, in a manner which allows expression and/or delivery of said nucleic acid molecule.

24. The expression vector of claim 15, wherein said vector comprises:
   a) a transcription initiation region;
   b) a transcription termination region;
   c) an intron;
   d) an open reading frame;
   e) a gene encoding at least one said nucleic acid molecule, wherein said gene is operably linked to the 3'-end of said open reading frame; and
   wherein said gene is operably linked to said initiation region, said intron, said open reading frame and said termination region, in a manner which allows expression and/or delivery of said nucleic acid molecule.

* * * * *

SEQUENCE LISTING

<160> NUMBER OF SEQ ID NOS: 35

<210> SEQ ID NO 1
<211> LENGTH: 313
<212> TYPE: RNA
<213> ORGANISM: Artificial Sequence
<220> FEATURE:
<223> OTHER INFORMATION: Description of Artificial Sequence: Nucleic
    acid molecule with catalytic activity.
<221> NAME/KEY: misc_feature
<222> LOCATION: (5)
<223> OTHER INFORMATION: n can represent any one of a, c, g, or u;
<221> NAME/KEY: misc_feature
<222> LOCATION: (9)..(308)
<223> OTHER INFORMATION: all n's can represent any one of a, c, g, or u,
    or may be optionally absent;

<400> SEQUENCE: 1
ucgangagnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnncg aaa                                                        313

<210> SEQ ID NO 2
<211> LENGTH: 313
<212> TYPE: RNA
<213> ORGANISM: Artificial Sequence
<220> FEATURE:
<223> OTHER INFORMATION: Description of Artificial Sequence: Nucleic
    acid molecule with catalytic activity.
<221> NAME/KEY: misc_feature
<222> LOCATION: (1)
<223> OTHER INFORMATION: "n" stands for 2'-O-methylthiomethyl uridine;
<221> NAME/KEY: misc_feature
<222> LOCATION: (2)
<223> OTHER INFORMATION: "n" stands for 2'-C-Allyl-U;
<221> NAME/KEY: misc_feature
<222> LOCATION: (5)
<223> OTHER INFORMATION: "n" stands for 6-Methyl-U;
<221> NAME/KEY: misc_feature
<222> LOCATION: (9)..(308)
<223> OTHER INFORMATION: all n's can represent any one of a, c, g, or u,
    or may be optionally absent;

<400> SEQUENCE: 2
nngangagnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnncg aaa                                                        313

<210> SEQ ID NO 3
<211> LENGTH: 313
<212> TYPE: RNA
<213> ORGANISM: Artificial Sequence
<220> FEATURE:
<223> OTHER INFORMATION: Description of Artificial Sequence: Nucleic
    acid molecule with catalytic activity.
<221> NAME/KEY: misc_feature

```
<222> LOCATION: (1)
<223> OTHER INFORMATION: "n" stands for 2'-O-methylthiomethyl uridine;
<221> NAME/KEY: misc_feature
<222> LOCATION: (2)
<223> OTHER INFORMATION: "n" stands for 2'-O-methylthiomethyl cytidine;
<221> NAME/KEY: misc_feature
<222> LOCATION: (5)
<223> OTHER INFORMATION: "n" stands for 6-Methyl-U;
<221> NAME/KEY: misc_feature
<222> LOCATION: (9)..(308)
<223> OTHER INFORMATION: all n's can represent any one of a, c, g, or u,
      or may be optionally absent;

<400> SEQUENCE: 3
nngangagnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnncg aaa                                                        313

<210> SEQ ID NO 4
<211> LENGTH: 313
<212> TYPE: RNA
<213> ORGANISM: Artificial Sequence
<220> FEATURE:
<223> OTHER INFORMATION: Description of Artificial Sequence: Nucleic
      acid molecule with catalytic activity.
<221> NAME/KEY: misc_feature
<222> LOCATION: (1)
<223> OTHER INFORMATION: n stands for 2'-O-MTM-U;
<221> NAME/KEY: misc_feature
<222> LOCATION: (2)
<223> OTHER INFORMATION: n stands for 2'-O-MTM-C;
<221> NAME/KEY: misc_feature
<222> LOCATION: (5)
<223> OTHER INFORMATION: n stands for 2'-C-Allyl-U;
<221> NAME/KEY: misc_feature
<222> LOCATION: (9)..(308)
<223> OTHER INFORMATION: all n's can represent any one of a, c, g, or u,
      or may be optionally absent;

<400> SEQUENCE: 4
nngangagnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnncg aaa                                                        313

<210> SEQ ID NO 5
<211> LENGTH: 313
<212> TYPE: RNA
<213> ORGANISM: Artificial Sequence
<220> FEATURE:
<223> OTHER INFORMATION: Description of Artificial Sequence: Nucleic
      acid molecule with catalytic activity.
<221> NAME/KEY: misc_feature
<222> LOCATION: (1)
<223> OTHER INFORMATION: n stands for 2'-O-MTM-U;
<221> NAME/KEY: misc_feature
<222> LOCATION: (2)
<223> OTHER INFORMATION: n stands for 2'-O-MTM-C;
<221> NAME/KEY: misc_feature
<222> LOCATION: (5)
```

<223> OTHER INFORMATION: n stands for Pyridin-4-One;
<221> NAME/KEY: misc_feature
<222> LOCATION: (9)..(308)
<223> OTHER INFORMATION: all n's can represent any one of a, c, g, or u,
       or may be optionally absent;

<400> SEQUENCE: 5
nngangagnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnncg aaa                                                        313

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Nucleic
       acid molecule for synthesis of X24, X27, and N28
       Ribozyme library.

<400> SEQUENCE: 6
gaggcgaaag ccgaaagccc uc                                               22

<210> SEQ ID NO 7
<211> LENGTH: 26
<212> TYPE: RNA
<213> ORGANISM: Artificial Sequence
<220> FEATURE:
<223> OTHER INFORMATION: Description of Artificial Sequence: Nucleic
       acid molecule for synthesis of X24, X27, and N28 Ribozyme library.
<221> NAME/KEY: misc_feature
<222> LOCATION: (1)
<223> OTHER INFORMATION: n represents a  modified pyrimidine
       ribonucleotide;
<221> NAME/KEY: misc_feature
<222> LOCATION: (4)
<223> OTHER INFORMATION: n represents a modified pyrimidine
       ribonucleotide.

<400> SEQUENCE: 7
ngangaggcg aaagccgaaa gcccuc                                           26

<210> SEQ ID NO 8
<211> LENGTH: 34
<212> TYPE: RNA
<213> ORGANISM: Artificial Sequence
<220> FEATURE:
<223> OTHER INFORMATION: Description of Artificial Sequence: Nucleic
       acid molecule for synthesis of X24, X27, and N28
       Ribozyme library.
<221> NAME/KEY: misc_feature
<222> LOCATION: (8)..(9)
<223> OTHER INFORMATION: n represents a  modified pyrimidine
       ribonucleotide;
<221> NAME/KEY: misc_feature
<222> LOCATION: (12)
<223> OTHER INFORMATION: n represents a  modified pyrimidine
       ribonucleotide.

<400> SEQUENCE: 8
acaaaganng angaggcgaa agccgaaagc ccuc                                  34

<210> SEQ ID NO 9

```
<211> LENGTH: 34
<212> TYPE: RNA
<213> ORGANISM: Artificial Sequence
<220> FEATURE:
<223> OTHER INFORMATION: Description of Artificial Sequence: Nucleic
      acid for preparation of "binding arms" ribozyme library.
<221> NAME/KEY: misc_feature
<222> LOCATION: (1)..(34)
<223> OTHER INFORMATION: all n's can represent any one of
      2'-O-methyl- a, c, g, or u.

<400> SEQUENCE: 9
nnnnnncuga ugaggccguu aggccgaaan nnnn                           4

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Nucleic
      acid for preparation of "binding arms" ribozyme library.

<400> SEQUENCE: 10
cugaugaggc cguuaggccg aaa                                      23

<210> SEQ ID NO 11
<211> LENGTH: 36
<212> TYPE: RNA
<213> ORGANISM: Artificial Sequence
<220> FEATURE:
<223> OTHER INFORMATION: Description of Artificial Sequence: Nucleic
      acid for preparation of "Loop II" Ribozyme library.
<221> NAME/KEY: misc_feature
<222> LOCATION: (19)..(22)
<223> OTHER INFORMATION: all n's can represent any one of a, c, g, or u.

<400> SEQUENCE: 11
ucuccaucug augaggccnn nnggccgaaa aucccu                        36

<210> SEQ ID NO 12
<211> LENGTH: 14
<212> TYPE: RNA
<213> ORGANISM: Artificial Sequence
<220> FEATURE:
<223> OTHER INFORMATION: Description of Artificial Sequence: Nucleic
      acid for preparation of "Loop II" Ribozyme library.

<400> SEQUENCE: 12
ggccgaaaau cccu                                                14

<210> SEQ ID NO 13
<211> LENGTH: 18
<212> TYPE: RNA
<213> ORGANISM: Artificial Sequence
<220> FEATURE:
<223> OTHER INFORMATION: Description of Artificial Sequence: Nucleic
      acid for preparation of "Loop II" Ribozyme library.

<400> SEQUENCE: 13
ucuccaucug augaggcc                                            18

<210> SEQ ID NO 14
<211> LENGTH: 11
<212> TYPE: RNA
<213> ORGANISM: Artificial Sequence
<220> FEATURE:
<223> OTHER INFORMATION: Description of Artificial Sequence: Synthesized
      Hammerhead Target.
<221> NAME/KEY: misc_feature
```

<222> LOCATION: (1)..(11)
<223> OTHER INFORMATION: all n's can represent any one of a, c, g, or u.

<400> SEQUENCE: 14
nnnnuhnnnn n                                                              11

<210> SEQ ID NO 15
<211> LENGTH: 28
<212> TYPE: RNA
<213> ORGANISM: Artificial Sequence
<220> FEATURE:
<223> OTHER INFORMATION: Description of Artificial Sequence: Synthesized
      Hammerhead Ribozyme.
<221> NAME/KEY: misc_feature
<222> LOCATION: (1)..(28)
<223> OTHER INFORMATION: all n's can represent any one of a, c, g, or u.

<400> SEQUENCE: 15
nnnnncugan gagnnnnnnc gaaannnn                                            28

<210> SEQ ID NO 16
<211> LENGTH: 15
<212> TYPE: RNA
<213> ORGANISM: Artificial Sequence
<220> FEATURE:
<223> OTHER INFORMATION: Description of Artificial Sequence: Synthesized
      Hairpin Target.
<221> NAME/KEY: misc_feature
<222> LOCATION: (1)..(15)
<223> OTHER INFORMATION: all n's can represent any one of a, c, g, or u.

<400> SEQUENCE: 16
nnnnnnnyng hynnn                                                          15

<210> SEQ ID NO 17
<211> LENGTH: 47
<212> TYPE: RNA
<213> ORGANISM: Artificial Sequence
<220> FEATURE:
<223> OTHER INFORMATION: Description of Artificial Sequence: Synthesized
      Hairpin Ribozyme.
<221> NAME/KEY: misc_feature
<222> LOCATION: (1)..(47)
<223> OTHER INFORMATION: all n's can represent any one of a, c, g, or u.

<400> SEQUENCE: 17
nnnngaagnn nnnnnnnna aahannnnnn nacauuacnn nnnnnnn                        47

<210> SEQ ID NO 18
<211> LENGTH: 49
<212> TYPE: RNA
<213> ORGANISM: Artificial Sequence
<220> FEATURE:
<223> OTHER INFORMATION: Description of Artificial Sequence: Hepatitis
      Delta Virus (HDV) Ribozyme.
<221> NAME/KEY: misc_feature
<222> LOCATION: (18)..(24)
<223> OTHER INFORMATION: all n's can represent any one of a, c, g, or u.

<400> SEQUENCE: 18
cuccaccucc ucgcggunnn nnnngggcua cuucgguagg cuaagggag                     49

<210> SEQ ID NO 19
<211> LENGTH: 176
<212> TYPE: RNA
<213> ORGANISM: Artificial Sequence
<220> FEATURE:
<223> OTHER INFORMATION: Description of Artificial Sequence: Neurospora
      VS Ribozyme.

```
<400> SEQUENCE: 19
gggaaagcuu gcgaagggcg ucgucgcccc gagcgguagu aagcagggaa cucaccucca      60
auuucaguac ugaaauuguc guagcaguug acuacuguua ugugauuggu agaggcuaag     120
ugacgguauu ggcguaaguc aguauugcag cacagcacaa gcccgcuugc gagaau        176

<210> SEQ ID NO 20
<211> LENGTH: 36
<212> TYPE: RNA
<213> ORGANISM: Artificial Sequence
<220> FEATURE:
<223> OTHER INFORMATION: Description of Artificial Sequence: Synthesized
      Hammerhead Motif/HH-A Motif.

<400> SEQUENCE: 20
acaaagacug augaggccga aaggccgaaa gcccuc                                36

<210> SEQ ID NO 21
<211> LENGTH: 36
<212> TYPE: RNA
<213> ORGANISM: Artificial Sequence
<220> FEATURE:
<223> OTHER INFORMATION: Description of Artificial Sequence:
      Synthesized Ribozyme HH-A variant.
<221> NAME/KEY: misc_feature
<222> LOCATION: (8)
<223> OTHER INFORMATION: n in position 8 stands for
      2'-O-methylthiomethyl uridine;
<221> NAME/KEY: misc_feature
<222> LOCATION: (9)
<223> OTHER INFORMATION: n in position 9 stands for 2'-C-Allyl-U;
<221> NAME/KEY: misc_feature
<222> LOCATION: (12)
<223> OTHER INFORMATION: n in position 12 stands for 6-Methyl-U;

<400> SEQUENCE: 21 acaaagannq angaggccga aaggccgaaa gcccuc                                36

<210> SEQ ID NO 22
<211> LENGTH: 36
<212> TYPE: RNA
<213> ORGANISM: Artificial Sequence
<220> FEATURE:
<223> OTHER INFORMATION: Description of Artificial Sequence:
      Synthesized Ribozyme HH-A variant.
<221> NAME/KEY: misc_feature
<222> LOCATION: (8)
<223> OTHER INFORMATION: n in position 8 stands for
      2'-O-methylthiomethyl uridine;
<221> NAME/KEY: misc_feature
<222> LOCATION: (9)
<223> OTHER INFORMATION: n in position 9 stands for
      2'-O-methylthiomethyl cytidine;
<221> NAME/KEY: misc_feature
<222> LOCATION: (12)
<223> OTHER INFORMATION: n in position 12 stands for 6-Methyl-U;

<400> SEQUENCE: 22 acaaagannq angaggccga aaggccgaaa gcccuc                                36

<210> SEQ ID NO 23
<211> LENGTH: 36
<212> TYPE: RNA
<213> ORGANISM: Artificial Sequence
<220> FEATURE:
<223> OTHER INFORMATION: Description of Artificial Sequence:
      Synthesized Ribozyme HH-A variant.
<221> NAME/KEY: misc_feature
<222> LOCATION: (8)
```

```
<223> OTHER INFORMATION: n in position 8 stands for
      2'-O-methylthiomethyl uridine;
<221> NAME/KEY: misc_feature
<222> LOCATION: (9)
<223> OTHER INFORMATION: n in position 9 stands for
      2'-O-methylthiomethyl cytidine;
<221> NAME/KEY: misc_feature
<222> LOCATION: (12)
<223> OTHER INFORMATION: n in position 12 stands for 2'-C-Allyl-U;

<400> SEQUENCE: 23
acaaaganng angaggccga aaggccgaaa gcccuc                              36

<210> SEQ ID NO 24
<211> LENGTH: 36
<212> TYPE: RNA
<213> ORGANISM: Artificial Sequence
<220> FEATURE:
<223> OTHER INFORMATION: Description of Artificial Sequence:
      Synthesized Ribozyme HH-A variant.
<221> NAME/KEY: misc_feature
<222> LOCATION: (8)
<223> OTHER INFORMATION: n in position 8 stands for
      2'-O-methylthiomethyl uridine;
<221> NAME/KEY: misc_feature
<222> LOCATION: (9)
<223> OTHER INFORMATION: n in position 9 stands for
      2'-O-methylthiomethyl-cytidine;
<221> NAME/KEY: misc_feature
<222> LOCATION: (12)
<223> OTHER INFORMATION: n in position 12 stands for Pyridin-4-one;

<400> SEQUENCE: 24
acaaaganng angaggccga aaggccgaaa gcccuc                              36

<210> SEQ ID NO 25
<211> LENGTH: 321
<212> TYPE: RNA
<213> ORGANISM: Artificial Sequence
<220> FEATURE:
<223> OTHER INFORMATION: Description of Artificial Sequence: Synthesized
      novel ribozyme.
<221> NAME/KEY: misc_feature
<222> LOCATION: (1)..(321)
<223> OTHER INFORMATION: all n's can represent any one of a, c, g, or u;
      positions 9-308 may be optionally absent;

<400> SEQUENCE: 25
nnnucganga gnnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn ncgaaannnn n                                              321

<210> SEQ ID NO 26
<211> LENGTH: 321
<212> TYPE: RNA
<213> ORGANISM: Artificial Sequence
<220> FEATURE:
<223> OTHER INFORMATION: Description of Artificial Sequence: Synthesized
      novel ribozyme.
<221> NAME/KEY: misc_feature
<222> LOCATION: (1)..(3)
<223> OTHER INFORMATION: all n's can represent any one of a, c, g, or u;
<221> NAME/KEY: misc_feature
<222> LOCATION: (4)
<223> OTHER INFORMATION: n stands for 2'-O-methylthiomethyl uridine;
```

<221> NAME/KEY: misc_feature
<222> LOCATION: (5)
<223> OTHER INFORMATION: n stands for 2'-C-Allyl-U;
<221> NAME/KEY: misc_feature
<222> LOCATION: (8)
<223> OTHER INFORMATION: n stands for 6-Methyl-U;
<221> NAME/KEY: misc_feature
<222> LOCATION: (12)..(311)
<223> OTHER INFORMATION: all n's can represent any one of a, c, g, or u,
    or may be optionally absent;
<221> NAME/KEY: misc_feature
<222> LOCATION: (317)..(321)
<223> OTHER INFORMATION: all n's can represent any one of a, c, g, or u;

<400> SEQUENCE: 26

```
nnnnnganga gnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn ncgaaannnn n                                                321
```

<210> SEQ ID NO 27
<211> LENGTH: 321
<212> TYPE: RNA
<213> ORGANISM: Artificial Sequence
<220> FEATURE:
<223> OTHER INFORMATION: Description of Artificial Sequence: Synthesized
    novel ribozyme.
<221> NAME/KEY: misc_feature
<222> LOCATION: (1)..(3)
<223> OTHER INFORMATION: all n's can represent any one of a, c, g, or u;
<221> NAME/KEY: misc_feature
<222> LOCATION: (4)
<223> OTHER INFORMATION: n stands for 2'-O-methylthiomethyl uridine;
<221> NAME/KEY: misc_feature
<222> LOCATION: (5)
<223> OTHER INFORMATION: n stands for 2'-O-methylthiomethyl cytidine;
<221> NAME/KEY: misc_feature
<222> LOCATION: (8)
<223> OTHER INFORMATION: n stands for 6-Methyl-U;
<221> NAME/KEY: misc_feature
<222> LOCATION: (12)..(311)
<223> OTHER INFORMATION: all n's can represent any one of a, c, g, or u,
    or may be optionally absent;
<221> NAME/KEY: misc_feature
<222> LOCATION: (317)..(321)
<223> OTHER INFORMATION: all n's can represent any one of a, c, g, or u;

<400> SEQUENCE: 27

```
nnnnnganga gnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn ncgaaannnn n                                                321
```

<210> SEQ ID NO 28
<211> LENGTH: 321
<212> TYPE: RNA
<213> ORGANISM: Artificial Sequence
<220> FEATURE:
<223> OTHER INFORMATION: Description of Artificial Sequence: Synthesized
    novel ribozyme.
<221> NAME/KEY: misc_feature

```
<222> LOCATION: (1)..(3)
<223> OTHER INFORMATION: all n's can represent any one of a, c, g, or u;
<221> NAME/KEY: misc_feature
<222> LOCATION: (4)
<223> OTHER INFORMATION: n stands for 2'-O-methylthiomethyl uridine;
<221> NAME/KEY: misc_feature
<222> LOCATION: (5)
<223> OTHER INFORMATION: n stands for 2'-O-methylthiomethyl cytidine;
<221> NAME/KEY: misc_feature
<222> LOCATION: (8)
<223> OTHER INFORMATION: n stands for 2'-C-Allyl-U;
<221> NAME/KEY: misc_feature
<222> LOCATION: (12)..(311)
<223> OTHER INFORMATION: all n's can represent any one of a, c, g, or u,
      or may be optionally absent;
<221> NAME/KEY: misc_feature
<222> LOCATION: (317)..(321)
<223> OTHER INFORMATION: all n's can represent any one of a, c, g, or u;

<400> SEQUENCE: 28
nnnnnganga gnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn ncgaaannnn n                                                321

<210> SEQ ID NO 29
<211> LENGTH: 321
<212> TYPE: RNA
<213> ORGANISM: Artificial Sequence
<220> FEATURE:
<223> OTHER INFORMATION: Description of Artificial Sequence: Synthesized
      novel ribozyme.
<221> NAME/KEY: misc_feature
<222> LOCATION: (1)..(3)
<223> OTHER INFORMATION: all n's can represent any one of a, c, g, or u;
<221> NAME/KEY: misc_feature
<222> LOCATION: (4)
<223> OTHER INFORMATION: n stands for 2'-O-methylthiomethyl uridine;
<221> NAME/KEY: misc_feature
<222> LOCATION: (5)
<223> OTHER INFORMATION: n stands for 2'-O-methylthiomethyl cytidine;
<221> NAME/KEY: misc_feature
<222> LOCATION: (12)..(311)
<223> OTHER INFORMATION: all n's can represent any one of a, c, g, or u,
      or may be optionally absent;
<221> NAME/KEY: misc_feature
<222> LOCATION: (12)..(311)
<223> OTHER INFORMATION: all n's can represent any one from a, c, g, or
      u, or may be optionally absent;
<221> NAME/KEY: misc_feature
<222> LOCATION: (317)..(321)
<223> OTHER INFORMATION: all n's can represent any one of a, c, g, or u;

<400> SEQUENCE: 29
nnnnnganga gnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn ncgaaannnn n                                                321

<210> SEQ ID NO 30
<211> LENGTH: 36
```

```
<212> TYPE: RNA
<213> ORGANISM: Artificial Sequence
<220> FEATURE:
<223> OTHER INFORMATION: Description of Artificial Sequence: Hammerhead
      Ribozyme B.

<400> SEQUENCE: 30
ucuccaucug augaggccga aaggccgaaa aucccu                              36

<210> SEQ ID NO 31
<211> LENGTH: 37
<212> TYPE: RNA
<213> ORGANISM: Artificial Sequence
<220> FEATURE:
<223> OTHER INFORMATION: Description of Artificial Sequence:
      Synthesized HH-B Ribozyme.

<400> SEQUENCE: 31
ucuccaucug augaggccga aaggccgaaa aucccuu                             37

<210> SEQ ID NO 32
<211> LENGTH: 37
<212> TYPE: RNA
<213> ORGANISM: Artificial Sequence
<220> FEATURE:
<223> OTHER INFORMATION: Description of Artificial Sequence:
      Synthesized HH-B Ribozyme.

<400> SEQUENCE: 32
ucuccaucug augaggccgu uaggccgaaa aucccuu                             37

<210> SEQ ID NO 33
<211> LENGTH: 17
<212> TYPE: RNA
<213> ORGANISM: Artificial Sequence
<220> FEATURE:
<223> OTHER INFORMATION: Description of Artificial Sequence:
      Synthesized nucleic acid molecule.

<400> SEQUENCE: 33
cagggauuaa uggagau                                                  17

<210> SEQ ID NO 34
<211> LENGTH: 34
<212> TYPE: RNA
<213> ORGANISM: Artificial Sequence
<220> FEATURE:
<223> OTHER INFORMATION: Description of Artificial Sequence:
      Synthesized HH Ribozyme.

<400> SEQUENCE: 34
caaagacuga ugaggccgaa aggccgaaag cccu                               34

<210> SEQ ID NO 35
<211> LENGTH: 34
<212> TYPE: RNA
<213> ORGANISM: Artificial Sequence
<220> FEATURE:
<223> OTHER INFORMATION: Description of Artificial Sequence:
      Synthesized HH Ribozyme Binding Arm Variant.
<221> NAME/KEY: misc_feature
<222> LOCATION: (1)..(6)
<223> OTHER INFORMATION: all n's can represent any one of a, c, g, or u;
<221> NAME/KEY: misc_feature
<222> LOCATION: (30)..(34)
```

-continued

```
<223> OTHER INFORMATION: all n's can represent any one of a, c, g, or u;

<400> SEQUENCE: 35
nnnnnncuga ugaggccgaa aggccgaaan nnnn                                34
```